US007585526B2

(12) United States Patent
Hamann

(10) Patent No.: US 7,585,526 B2
(45) Date of Patent: *Sep. 8, 2009

(54) FLEXIBLE ELASTOMER ARTICLES AND METHODS OF MANUFACTURING

(75) Inventor: Curtis P. Hamann, Paradise Valley, AZ (US)

(73) Assignee: Smarthealth, Inc., Phoenix, AZ (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/373,985

(22) Filed: Feb. 25, 2003

(65) Prior Publication Data
US 2004/0091504 A1 May 13, 2004

Related U.S. Application Data

(60) Provisional application No. 60/425,075, filed on Nov. 7, 2002.

(51) Int. Cl.
A61K 36/33 (2006.01)
(52) U.S. Cl. .................................. 424/757; 2/161.7
(58) Field of Classification Search ................ None
See application file for complete search history.

(56) References Cited

U.S. PATENT DOCUMENTS

| | | |
|---|---|---|
| 3,025,403 A | 3/1962 | Belknap et al. |
| 3,059,241 A | 10/1962 | O'Brien et al. |
| 3,225,360 A | 12/1965 | Keilen, Jr. et al. |
| 3,286,011 A | 11/1966 | Kavalir et al. |
| 3,397,265 A | 8/1968 | Ansell |
| 3,813,695 A | 6/1974 | Podell, Jr. et al. |
| 3,933,723 A | 1/1976 | Grenness |
| 3,942,193 A | 3/1976 | Pugh |
| 4,061,709 A | 12/1977 | Miller et al. |
| 4,070,713 A | 1/1978 | Stockum |
| 4,185,330 A | 1/1980 | Stager |
| 4,186,445 A | 2/1980 | Stager |
| 4,251,574 A | 2/1981 | Berend |
| 4,302,852 A | 12/1981 | Joung |
| 4,340,348 A | 7/1982 | Kurtz |
| 4,371,988 A | 2/1983 | Berend |
| 4,390,492 A | 6/1983 | Kurtz |
| 4,463,156 A | 7/1984 | McGary, Jr. et al. |
| 4,482,577 A | 11/1984 | Goldstein et al. |
| 4,499,154 A | 2/1985 | James et al. |
| 4,548,844 A | 10/1985 | Podell et al. |
| 4,575,476 A | 3/1986 | Podell et al. |
| 4,696,065 A | 9/1987 | Elenteny |
| 4,917,850 A | 4/1990 | Gray |
| 4,954,309 A | 9/1990 | McGlothlin et al. |
| 5,001,354 A | 3/1991 | Gould et al. |
| 5,014,361 A | 5/1991 | Gray |
| 5,020,162 A | 6/1991 | Kersten et al. |
| 5,088,125 A | 2/1992 | Ansell et al. |
| 5,112,900 A | 5/1992 | Buddenhagen et al. |
| 5,215,701 A | 6/1993 | Gould et al. |
| 5,272,771 A | 12/1993 | Ansell et al. |
| 5,284,607 A | 2/1994 | Chen |
| 5,370,915 A | 12/1994 | Hirakawa |
| 5,395,666 A | 3/1995 | Brindle |
| 5,405,666 A | 4/1995 | Brindle |
| 5,405,690 A | 4/1995 | Hirakawa |
| 5,407,715 A | 4/1995 | Buddenhagen et al. |
| 5,444,121 A | 8/1995 | Grennes et al. |
| 5,458,936 A | 10/1995 | Miller et al. |
| 5,459,879 A | 10/1995 | Fuchs |
| 5,483,697 A | 1/1996 | Fuchs |
| 5,568,657 A | 10/1996 | Cordova et al. |
| 5,570,475 A | 11/1996 | Nile et al. |
| 5,598,850 A | 2/1997 | Miller et al. |
| 5,601,092 A | 2/1997 | Miller et al. |
| 5,612,083 A | 3/1997 | Haung et al. |
| 5,614,202 A | 3/1997 | DeFina |
| 5,620,773 A | 4/1997 | Nash |
| 5,644,798 A | 7/1997 | Shah |
| 5,651,995 A | 7/1997 | Oyama et al. |
| RE35,616 E | 9/1997 | Tillotson et al. |
| 5,682,613 A | 11/1997 | Dinatale |

(Continued)

FOREIGN PATENT DOCUMENTS

| | | |
|---|---|---|
| CN | ZL 95 2 22651.0 | 6/1996 |
| JP | 11229211 | 8/1999 |

OTHER PUBLICATIONS

Mardon, P.; The Products; www.mardons.demon.co.ud/products.htm;2002—pp. 1-10.

Galati, E.M., et al.; Biological Effect of *Opuntia ficus indica* (L.) Mill. (Cactaceae) Waste Matter Note I: Diuretic Activity; Journal of Ethnopharmacology, (2002), pp. 17-21, vol. 79, Elsevier Science Ireland Ltd.

Lahsasni, S.; et al.; Experimental Study and Modeling of Adsorption and Desorption Isotherms of Prickly Pear Peel (*Opuntia ficus indica*); Jounal of Food Engineering, 2002, pp. 201-207, vol. 55, Elsevier Science Ltd.

Lee, E., et al.; Effects of *Opuntia ficus-indica* var. *saboten* Stem on Gastric Damages in Rats; Archives of Pharmacal Research, (2002), vol. 25, Issue 1, Abstract-Medline.

(Continued)

*Primary Examiner*—Susan C Hoffman
(74) *Attorney, Agent, or Firm*—Reinhart Boerner Van Deuren P.C.

(57) ABSTRACT

Flexible elastomer articles and methods of making the same are disclosed in which a material, a botanical extract, is incorporated into an elastomer emulsion, solution and/or plastisol in order to enhance the physical and therapeutic properties of articles made from these materials. In another aspect, the invention relates to coating surfaces of flexible elastomer articles with a non-Aloe vera mucinous botanical or laboratory produced polysaccharide which is fortified by additives known to protect, restore and moisturize mammalian skin or mucosa and to enhance ease of application or donnability of the article. Flexible elastomer articles include gloves and other single layer or multi-layer flexible elastomer articles.

12 Claims, 22 Drawing Sheets

U.S. PATENT DOCUMENTS

| | | | |
|---|---|---|---|
| 5,691,069 | A | 11/1997 | Lee |
| 5,691,446 | A | 11/1997 | Dove |
| 5,700,585 | A | 12/1997 | Lee |
| 5,708,132 | A | 1/1998 | Grimm |
| 5,712,346 | A | 1/1998 | Lee |
| 5,741,885 | A | 4/1998 | Dove |
| 5,742,943 | A | 4/1998 | Chen |
| 5,800,818 | A | 9/1998 | Prugnaud et al. |
| 5,807,941 | A | 9/1998 | Tsuji et al. |
| 5,833,915 | A | 11/1998 | Shah |
| 5,851,683 | A | 12/1998 | Plamthottam et al. |
| 5,869,072 | A | 2/1999 | Berry |
| 5,877,244 | A | 3/1999 | Hoover et al. |
| 5,881,386 | A | 3/1999 | Horwege et al. |
| 5,881,387 | A | 3/1999 | Merovitz et al. |
| 5,900,452 | A | 5/1999 | Plamthottam |
| 5,910,533 | A | 6/1999 | Ghosal et al. |
| 5,965,276 | A | 10/1999 | Shlenker et al. |
| 5,974,589 | A | 11/1999 | Pugh et al. |
| 5,985,955 | A | 11/1999 | Bechara et al. |
| 5,993,923 | A | 11/1999 | Lee |
| 5,997,969 | A | 12/1999 | Gardon |
| 6,000,061 | A | 12/1999 | Taneja et al. |
| 6,016,570 | A | 1/2000 | Vande Pol et al. |
| 6,017,997 | A | 1/2000 | Snow et al. |
| 6,019,922 | A | 2/2000 | Hassan et al. |
| 6,031,042 | A | 2/2000 | Lipinski |
| 6,066,697 | A | 5/2000 | Coran et al. |
| 6,099,866 | A | 8/2000 | Slimak |
| 6,121,366 | A | 9/2000 | Sharma |
| 6,213,123 | B1 | 4/2001 | Miller et al. |
| 6,221,447 | B1 | 4/2001 | Munn et al. |
| 6,242,042 | B1 | 6/2001 | Goldstein et al. |
| 6,254,947 | B1 | 7/2001 | Schaller |
| 6,274,154 | B1 | 8/2001 | Chou |
| 6,280,673 | B1 | 8/2001 | Green et al. |
| 6,284,856 | B1 | 9/2001 | Lee |
| 6,288,159 | B1 | 9/2001 | Plamthottam |
| 6,306,514 | B1 | 10/2001 | Weikel et al. |
| 6,345,394 | B1 | 2/2002 | Nakamura et al. |
| 6,347,408 | B1 | 2/2002 | Yeh |
| 6,369,154 | B1 | 4/2002 | Suddaby |
| 6,380,283 | B1 | 4/2002 | Perrella et al. |
| 6,391,409 | B1 | 5/2002 | Yeh et al. |
| 6,414,083 | B2 | 7/2002 | Plamthottam |
| 6,423,328 | B2 | 7/2002 | Chou |
| 6,440,498 | B2 | 8/2002 | Schaller |
| 6,447,820 | B1 | 9/2002 | Niaz |
| 6,465,591 | B1 | 10/2002 | Lee |
| 6,488,948 | B1 * | 12/2002 | Danieli ............... 424/404 |
| 6,589,544 | B2 | 7/2003 | Leong |
| 6,630,152 | B2 | 10/2003 | Chou |
| 7,455,863 | B2 * | 11/2008 | Hamann ............... 424/767 |
| 2001/0048937 | A1 | 12/2001 | Chou |
| 2002/0025335 | A1 | 2/2002 | Chou |
| 2002/0102317 | A1 | 8/2002 | Gutterrez et al. |
| 2002/0110584 | A1 | 8/2002 | Chou |
| 2002/0114825 | A1 | 8/2002 | Leong |
| 2002/0132021 | A1 | 9/2002 | Raskin et al. |
| 2003/0017193 | A1 | 1/2003 | Chou |
| 2003/0204893 | A1 | 11/2003 | Chou |
| 2004/0091557 | A1 | 5/2004 | Hamann |

OTHER PUBLICATIONS

Carrillo-Lopez, A., et al.; Hydrolytic Activity and Ultrastructural Changes in Fruit Skins from Two Prickly Pear (*Opuntia* sp.) Varieties During Storage; Journal of Agricultural and Food Chemistry, (2002), vol. 50, Issue 6, Abstract-Medline.

Monje, P., et al.; Characterization of Calcium Oxalates Generated as Biominerals in Cacti; Plant Physiology, (2002), vol. 128, Issue 2, Abstract-Medline.

Lahsasni, S., et al.; Moisture Adsorption-Desorption Isotherms of Prickly Pear Cladode (*Opuntia ficus indica*) at Different Temperatures; Energy Conversion and Management, 2002, pp. 1-14, Elsevier Science Ltd.

Vande Water, P.; The Effect of Chemical Processing on the $\delta^{13}$ C Value of Plant Tissue; Geochimica et Cosmochimica Acta, (2002), pp. 1211-1219, vol. 66, No. 7, Elsevier Science Ltd, USA.

Nyffeler, R.; Phylogenetic Relationships in the Cactus Family (Cactaceae) Based on Evidence from TrnKl MatK and TmL-TrnF Sequences; American Journal of Botany, (2002), pp. 312,326, vol. 89(2).

The Nopal; http://www.elbalero.gob.mx/kids/about/did/nopal.html Oct. 8, 2002—pp. 1-2.

The Nopal Trade Products; http://www.thenopaltrade.com/nopal-plants.html Oct. 9, 2002—pp. 1-3.

Nopal (definition of); Merriam-Webster's Collegiate Dictionary; 2002—pp. 1-2.

Prickly Pear (definition of); Merriam-Webster's Collegiate Dictionary; 2002—pp. 1-3.

Budinsky, A., et al.; Regular Ingestion of *Opuntia robusta* Lowers Oxidation Injury; Prostaglandins, Leukotrienes and Essential Fatty Acids, (2001), pp. 45-50, vol. 65(1), Harcourt Publishers Ltd.

Galati, E.M., et al.; Antiulcer Activity of *Opuntia ficus indica* (L.) Mill. (Cactaceae): Ultrastructural Study; Journal of Ethnopharmacology, (2001), pp. 1-9, vol. 7, Elsevier Science Ireland Ltd.

Fernandez-Lopez, J., et al.; Application of High-Performance Liquid Chromatography to the Characterization of Betalain Pigments in Prickly Pear Fruits; Journal of Chromatography A, (2001), pp. 415-420, vol. 913, Elsevier Science B.V.

Majdoub, H., et al.; Prickly Pear Nopals Pecting from *Opuntia ficus-indica* Physico-Chemical Study in Dilute and Semi-Dilute Solutions; Carbohydrate Polymers, (2001), pp. 69-79, vol. 46, Elsevier Science Ltd.

Park, et al.; An Anti-Inflammatory Principle from Cactus; Filoterapia, (2001), pp. 288-290, 72, Elsevier Science B.V.

Park, et al.; Wound Healing Activity of *Opuntia ficus;indica*; Filoterapia, (2001), pp. 165-167, 72, Elsevier Science B.V.

Bwititi, P., et al.; Effects of *Opuntia megacantha* on Blood Glucose and Kidney Function in Streptozotocin Diabetic Rats; Journal of Ethnopharmacology, (2000), pp. 247-252, vol. 69, Elsevier Science Ireland Ltd.

Piga, A., et al.; Influence of Storage Temperature on Shelflife of Minimally Processed Cactus Pear Fruits; Lebensm.-Wiss. U.-Technol., (2000) pp. 15-20, vol. 33, Academic Press.

Veronin, M.A., et al.; The Validity of Health Claims on the World Wide Web: a Systematic Survey of the Herbal Remedy *Opuntia*; American Journal of Health Promotion, (2000), vol. 15, Issue 1, Abstract-Medline.

Ram, M., et al.; Wound Response and Regeneration in *Coelarthrum opuntia*; Aquatic Botany, (2000), pp. 345-351, vol. 68, Elsevier Science B.V.

North, G., et al.; Heterogeneity in Water Availability Alters Cellular Development and Hydraulic Conductivity along Roots of a Desert Succulent; Annals of Botany, (2000), pp. 247-255 vol. 85, Annals of Botany Company.

Saenz, C.; Processing Technologies: an Alternative for Cactus Pear (*Opuntia* spp.) Fruits and Cladodes; Journal of Arid Environments, (2000), pp. 209-225 vol. 46, Academic Press.

Loro, J.F., et al.; Preliminary Studies of Analgesic and Anti-Inflammatory Properties of *Opuntia dillenii* Aqueous Extract; Journal of Ethnopharmacology, (1999), pp. 213-218, vol. 67, Elsevier Science Ireland Ltd.

Contreras-Esquivel, J.C., et al.; Pectinesterase Extraction from Mexican Lime (*Citrus aurantifolia* Swingle) and Prickly Pear (*Opuntia ficus indica* L.) Peels; Food Chemistry, (1999) pp. 153-156, vol. 65, Elsevier Science Ltd.

Cardenas, A., et al.; Rheology and Aggregation of Cactus (*Opuntia ficus-indica*) Mucilage in Solution; Journal of the Professional Association of Cactus Development,, (1998), pp. 152-159, vol. 2.

Park, et al.; Studies on the pharmacological action of cactus; indentification of its anti-inflammatory effect; Archives of Pharmacal Research, Feb. 1998, vol. 21, Issue 1, Abstract-Medline.

Trejo-Gonzalez, A., et al.; A Purified Extract from Prickly Pear Cactus (*Opuntia fuliginosa*) Controls Experimentally Induced Diabetes in Rats; Journal of Ethnopharmacology ,(1996), pp. 27-33, vol. 55, Elsevier Science Ireland Ltd.

Ahmad, A., et al.; Antiviral Properties of Extract of *Opuntia streptacantha*; Antiviral Research, (1996), pp. 75-85, vol. 30, Elsevier Science B.V.

Palermo, J., et al.; Short Side Chain Sterols from the Tunicate Polizoa *Opuntia*; Steroids, (1996), pp. 2-6, vol. 61, Elsevier Science, Inc., New York, USA.

Mohamed-Yasseen, Y., et al.; A Note on the Uses of *Opuntia* spp. In Central/North America; Journal of Arid Environments, (1996), pp. 347-353, vol. 32, Academic Press Limited.

Roman-Ramos, R., et al.; Anti-Hyperglycemic Effect of Some Edible Plants; Journal of Ethnopharmacology, (1995), pp. 25-32, vol. 48, Elsevier Science Ireland Ltd.

Padiglia, A., et al.; Purification and Characterization of *Opuntia* Peroxidase; Phytochemistry, (1995), pp. 295-297, vol. 39, No. 2, Elsevier Science Ltd, Great Britain.

North, G. et al.; Cladode Development for *Opuntia ficus-indica* (Cactaceae) Under Current and Doubled $CO_2$ Concentrations; American Journal of Botany, (1995), pp. 159-166, vol. 82(2).

Wang, N., et al.; Phloem Exudate Collected via Scale Insect Stylets for the CAM Species *Opuntia ficus-indica* under Current and Doubled $CO_2$ Concentrations; Annals of Botany, (1995), pp. 525-532, vol. 75, Annals of Botany Company.

Nobel, P., et al.; Light, Chlorophyll, Carboxylase Activity and $CO_2$ Fixation at Various Depths in the Chlorenchyma of *Opuntia ficus-indica* (L.) Miller Under Current and Elevated $CO_2$ ; New Phytol, (1994), pp. 315-322, vol. 128.

Hamann, et al.; Allergies Associated with Medical Gloves—Manufacturing Issues; Occupational Dermatoses, (1994), pp. 547-559, vol. 12, No. 3.

Saenz, C., et al.; Colour Changes in Concentrated Juices of Prickly Pear (*Opuntia ficus indica*) During Storage at Different Temperatures; Lebensmittel-Wissenschaft und-Technologie, (1993) , vol. 26, Issue 5, Abstract-Science Direct.

Savio, Y; Nopal Facts, University of California, Davis, (Jun. 1989), USA.

Prickly Pear Cactus; Small Farm Center, Cooperative Extension, University of California, Davis, CA, (Jul. 1989), USA.

Mauseth, J.; Introduction to Cactus Anatomy, Part 5. Secretory Cells; Cactus & Succulent Journal, (1983), pp. 171-175, vol. 55, USA.

Nobel, P.; Nutrient Levels in Cacti—Relation to Nocturnal Acid Accumulation and Growth; Amer. J. Bot., (1983), pp. 1244-1253, vol. 70(8).

Pinkava, D., et al.; Chromosome Numbers in Some Cacti of Western North America, IV; Bulletin of the Torrey Botanical Club, (1982), pp. 121-128, vol. 109, No. 2.

Breckenridge, et al.; Echinocereus; Systematic Botany, (1982), pp. 370-378, vol. 7.

Trachtenberg, S., et al.; The Mucilage Cells of *Opuntia ficus-indica* (L.) Mill.—Development, Ultrastructure, and Mucilage Secretion; Bot. Gaz., (1981), pp. 206-213, vol. 142(2).

Mauseth, J.; A Stereological Morphometric Study of the Ultrastructure of Mucilage Cells in *Opuntia polyacantha* (Cactaceae)—Bol. Gaz., (1980), pp. 374-378, vol. 141(4).

Parfitt, B.; Origin of *Opuntia curvospina* (Cactaceae); Systematic Botany, (1980), pp. 408-418, vol. 5(4).

Mauseth, J.; Release of Whole Cells of *Nopalea* (Cactaceae) into Secretory Canals; Bot. Gaz., (1980), pp. 15-18, vol. 141(1).

Conde, L.; Anatomical Comparisons of Five Species of *Opuntia* (Cactaceae); Ann. Missouri Bot. Gard., (1975), pp. 425-473, vol. 62.

Thomson, W.W., et al.; Studies on the Ultrastructure of the Guard Cells of *Opuntia*; Amer. J. Bot., (1970), pp. 309-316, vol. 57(3).

Cabrera, L.; Propiedades Medicinales de las Mas Conocidas Plantas de Mexico; Plantas Curativas de Mexico, (1943), Second Ed.; pp. 163-164.

Malainine, M., et al., Structure and Morphology of Cladodes and Spines of *Opuntia ficus-indica*. Celulose Extraction and Characterization; Carbohydrate Polymers, (2003), pp. 77-83, vol. 51, Elsevier Science Ltd.

ASTM—Designation D412-98a—Standard Test Methods for Vulcanized Rubber and Thermoplastic Elastomers-Tension, (Aug. 1998), pp. 1-13.

ASTM—Designation D573-99—Standard Test Method for Rubber-Deterioration in an Air Oven, (Dec. 1999), pp. 1-6.

ASTM—Designation-D3577-01$^{t2}$a—Standard Specification for Rubber Surgical Gloves, (Jan. 2002), pp. 1-4.

ASTM—Designation D3578-01a$^{t2}$ —Standard Specification for Rubber Examination Gloves, (Jan. 2002), pp. 1-5.

ASTM—Designation D3767-01—Standard Practice for Rubber—Measurement of Dimensions, (Mar. 2001), pp. 1-7.

ASTM—Designation D4679-02—Standard Specification for Rubber General Purpose, Household or Beautician Gloves, (Mar. 2002), pp. 1-3.

ASTM—Designation-D5151-99—Standard Test Method for Detection of Holes in Medical Gloves, (Jun. 1999), pp. 1-2.

ASTM—Designation-D5250-00$^{t4}$ —Standard Specification for Poly(vinyl chloride) Gloves for Medical Application, (Feb. 2000), pp. 1-3.

ASTM—Designation-D5712-99—Standard Test Method for The Analysis of Aqueous Extractable Protein in Natural Rubber and Its Products Using the Modified Lowry Method, (Sep. 1999), pp. 1-4.

ASTM—Designation-D6124-01—Standard Test Method for Residual Powder on Medical Gloves, (Sep. 2001), pp. 1-4.

ASTM—Designation-D6319-00a$^{t3}$ —Standard Specification for Nitrile Examination Gloves for Medical Application, (Jan. 2001), pp. 1-4.

ASTM—Designation-D6355-98—Standard Test Method for Human Repeat Insult Patch Testing of Medical Gloves, (Feb. 1999), pp. 1-9.

ASTM—Designation-D6466-00—Standard Test Method for The Immunological Measurement of Antigenic Protein in Natural Rubber and its Product, (Mar. 2000), pp. 1-6.

ASTM—Designation-F1671-97b—Standard Test Method for Resistance of Materials Used in Protective Clothing to Penetration by Blood-Borne Pathogens Using Phi-X174 Bacteriophage Penetration as a Test System, (Feb. 1998), pp. 1-10.

ISO-10282—Single-use sterile surgical rubber gloves, Specification, Second edition, (Sep. 15, 2002), pp. 1-16.

ISO-11193-1—Single-use medical examination gloves—Part 1: Specification for gloves made from rubber latex or rubber solution, First edition, (Nov. 1, 2002), pp. 1-14.

S. Côté, et al., Ease of Donning Commercially Available Latex Examination Gloves, (1998), pp. 331-337, John Wiley & Sons, Inc. CCC 0021-9304/98/03033/07.

http://www.nhklabs.com/live/botanicals_extracts01.htm, NHK Laboratories, (Dec. 16, 2002), pp. 1-5.

http://www.aloecorp.com/products.html—Aloecorp List of Products, (Dec. 16, 2002), pp. 1-2.

T. T. Manson, et al., The Journal of Emergency Medicine, "A New Glove Puncture Detection System", (1995), pp. 357-364, vol. 13 No. 3, Elsevier Science Ltd.

Medina-Torres, et al., Rheological properties of the mucilage gum (*Opuntia ficus indica*), (Jan. 14, 2000), Food Hydrocolloids 14 (2000) 417-424, Elsevier Science Ltd., USA.

Fisher, M.D. et al., Ease of Donning Commercially Available Powder-Free Surgical Gloves—(Accepted Jul. 30, 1996), pp. 291-295, John Wiley & Sons, Inc.

Paulsen et al., Water-Soluble Polysaccharides of *Opuntia ficus-indica* CV "Burbank's Spineless", Phytochemistry (1979), pp. 569-571, vol. 18, Pergamon Press, England.

D. McGarvie et al., The Acid-Labile, Peripheral Chains of the Micilage of *Opuntia ficus-indica*, Carbohydrate Research (1981), pp. 57-65, vol. 94, Elsevier Scientific Publishing Company, Amsterdam, Netherlands.

Saag et al., Cactaceae Micilage Composition, J. Sci. Fd. Agric., (1975), pp. 993-1000, vol. 26.

Amin et al., The mucilage of *Opuntia ficus-indica* Mill., Carbohyd. Res. (1970) pp. 159-161, 15, Elsevier Publishing Company, Amsterdam Netherlands.

Parikh et al., Cholla Gum, I. Structure of the Degraded Cholla Gum, Canadian Journal of Chemistry (1966), pp. 327-333, vol. 44.

Parikh et al., Cholla Gum, II. Structure of the Undergraded Cholla Gum, Canadian Journal of Chemistry (1966), pp. 1531-1539, vol. 44.

www.NHKlabs.com, (Jan. 27, 2003), pp. 1-5, NHK Laboratories Ingredient Marketplace.

www.sardagum,com, (Jan. 27, 2003), pp. 1-2, Sarda Gums & Chemicals.

www.plthomas.com, (Jan. 27, 2003), pp. 1-22, P.L. Thomas & Co., Inc.

http://my.ecplaza.net/xingdachem, (Jan. 27, 2003), pp. 1-3, Xiamen Xing Da Chemicals.

www.pangaeasciences.com, (Jan. 27, 2003), pp. 1-10, Pangaea Sciences.

www.glucomannan.com, (Jan. 28, 2003), Glucomannan Natural Soluble Fiber, pp. 1-2.

www.cognis.com, (Jan. 27, 2003), pp. 1-8, Cognis Homepage.

http://www.voigtglobal.com/index.html, Voigt Global Distribution, (Feb. 19, 2003), pp. 1-3.

Lahsasni et al., Moisture adsorption-desorption isotherms of prickly pear cladode (*Opuntia ficus indica*) at different temperatures, Energy Conversion and Management (2003), pp. 923-936, vol. 44, Elsevier Science Ltd.

Quantachrome Hydrosorb™ 1000—Water Vapor Sorption Analyzer—www.quantachrome.com/Hydrosorb.b1, (Feb. 3, 2003), Quantachrome Instruments, Boynton Beach, FL, USA.

http://www.ifi-online.com/preview/hi_preview.html, (Feb. 14, 2003), Hi Europe Preview, Adumin Food Ingredients, pp. 1.

http://www.adumim.co.il/, (Feb. 14, 2003), "Fenu Pure", pp. 1-3, Israel.

http://www.matimop.org.il/newrdinf/company/c111.htm, (Feb. 14, 2003), pp. 1-3, Adumin Food Ingredients (Chemicals) Ltd.

http://www.herbamed.co.il/prostl.html 1997.

http:\\www.natunola.com/extracts.htm; (Mar. 25, 2003).

* cited by examiner

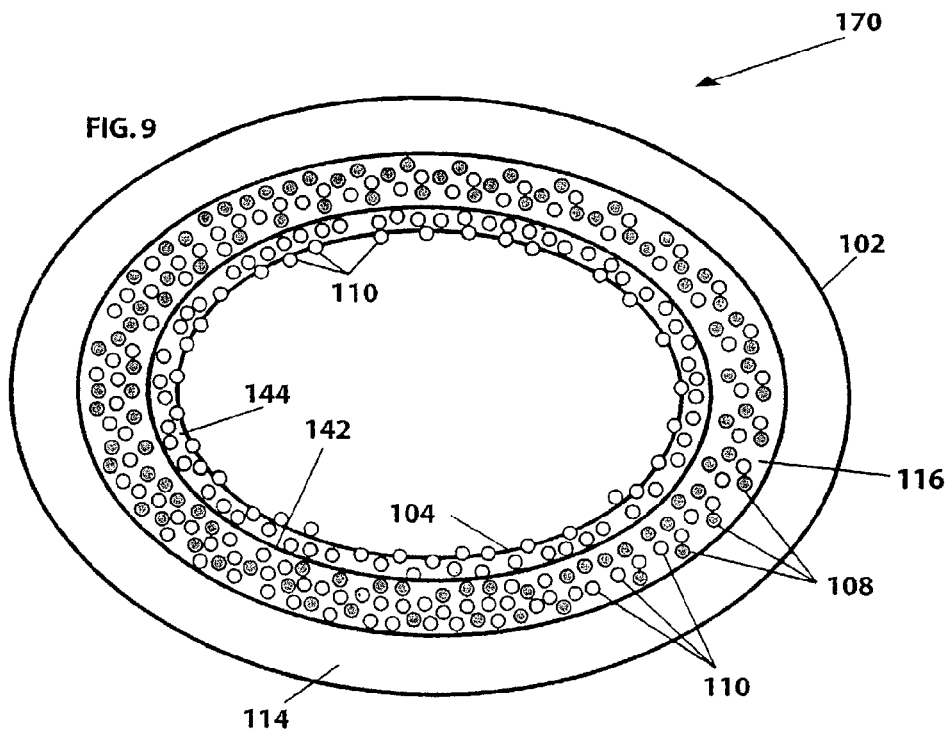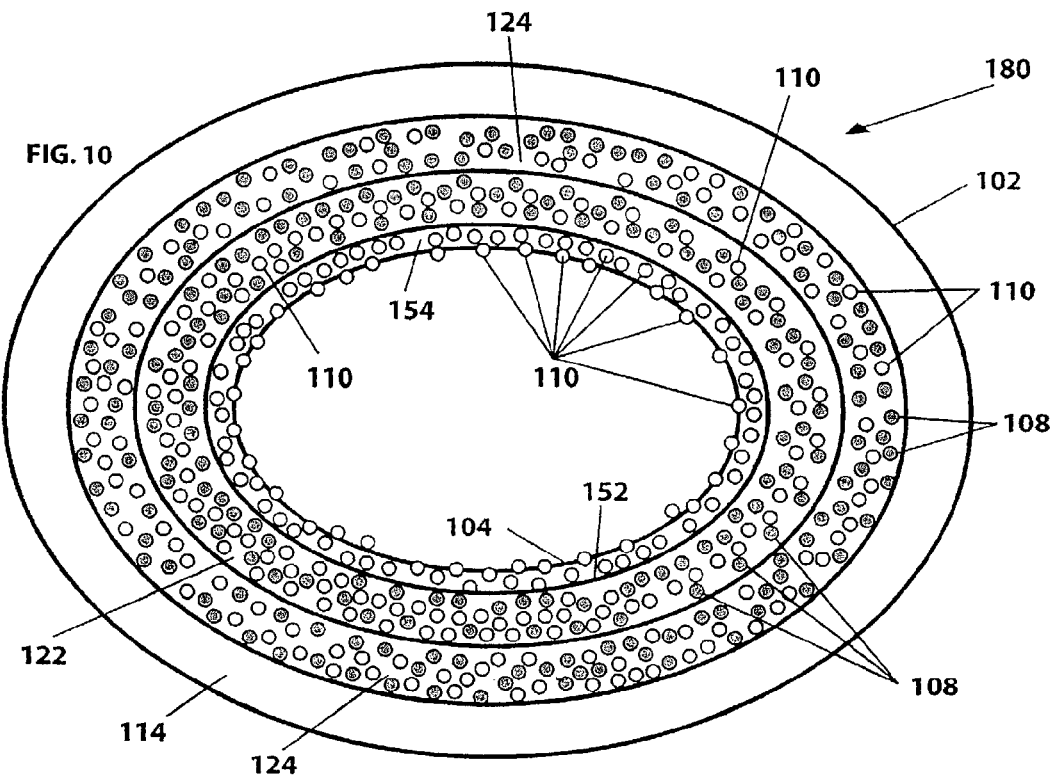

DIPPING OPERATION

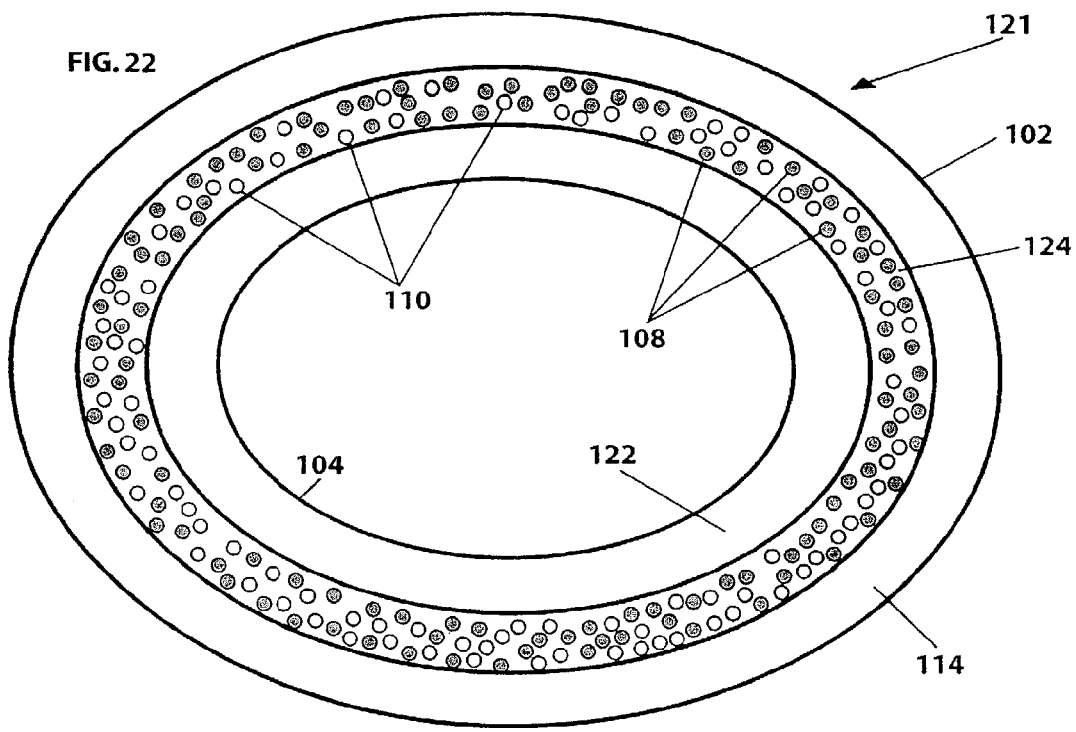
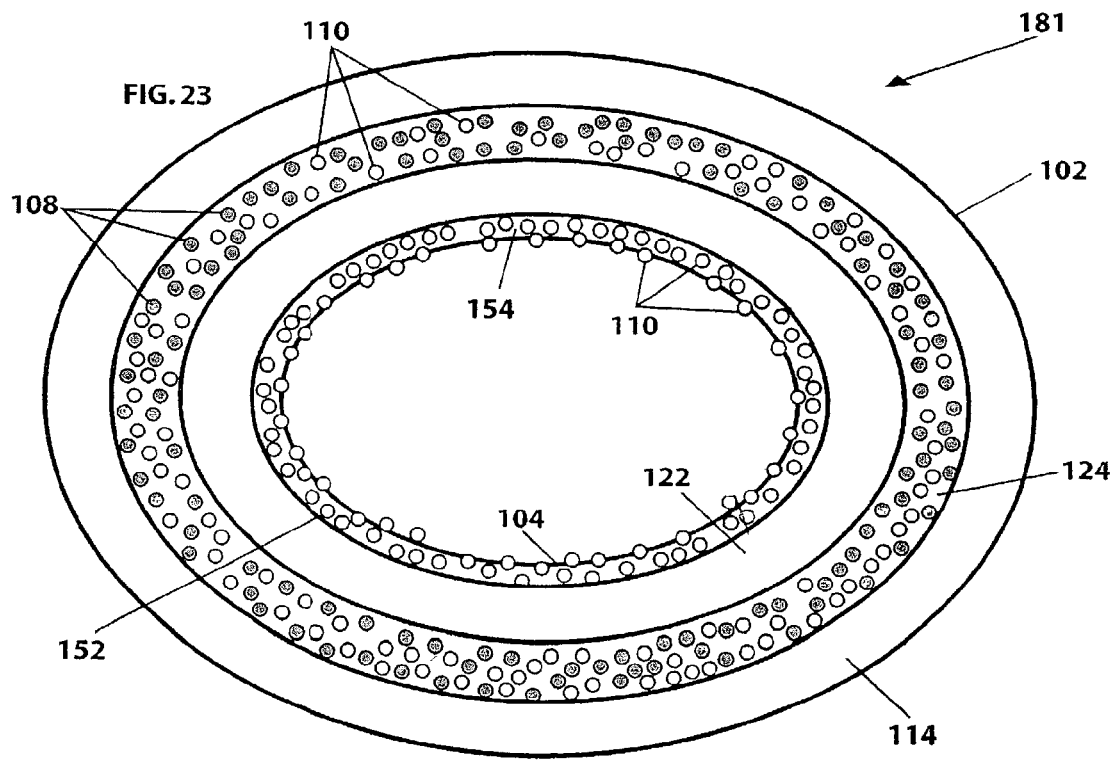

FLEXIBLE ELASTOMER ARTICLES AND METHODS OF MANUFACTURING

This application claims benefit of U.S. Provisional Application No. 60/425,075 filed on Nov. 7, 2002, the disclosure of which is hereby incorporated by reference.

BACKGROUND OF THE INVENTION

1. Field of the Invention

The present invention relates generally to flexible elastomer articles and methods of making the same in which the articles contain a moisturizing and/or therapeutic material or materials incorporated into an elastomer(s) from which the article is made or coated on the wearer contacting surface of the article, or both. More particularly, the invention relates to, in one aspect, elastomer(s) modified with the addition of botanical extracts in order to enhance the physical and therapeutic properties of articles made from these materials. In a second aspect, the invention relates to coating surfaces of flexible elastomer articles to improve skin or mucosa moisturizing properties and donnability with a non-Aloe vera coating material of a mucinous botanical or laboratory produced polysaccharide which is fortified by additives known to protect and restore mammalian skin. A third aspect of the invention combines the first and second aspects. Flexible elastomer articles include gloves and other single layer or multi-layer flexible elastomer articles, e.g., catheters, stents, incontinence devices having a sheath or sheath type construction, condoms, cervical caps, diaphragms, dental dams, elastomer sheets, balloons for use in medical devices, sheaths or tubes used for medical devices, and finger cots.

Disposable gloves are widely used by members of the medical community, the scientific community, and the industrial community to protect the wearer from chemical exposure, mechanical abrasion, environmental hazards, biohazard contamination and to prevent transmission of disease or contaminants. Health care providers frequently wear disposable gloves while performing surgery or other medical or dental procedures such as patient examinations; thus, the gloves are often also referred to as disposable examination gloves or disposable surgical gloves. The disposable gloves are impermeable to biological fluids, tissues and solids produced by the body or other contaminants (human or animal) advantageously protecting the wearer from fomitic (transmission by objects that harbor pathogenic organisms) transmission of pathogens and disease.

Also, disposable gloves are worn by individuals who wish to protect their hands from various chemicals, materials and objects which may irritate, damage or dry out the users skin and which may be harmful or potentially harmful if allowed to contact or permeate the dermal barrier. These gloves may be worn in the occupational setting by scientists, cleaning service workers, food handlers, law enforcement workers, beauticians or other workers having special protection needs. Thus, disposable gloves may also be referred to as protective gloves or industrial gloves. Also some disposable gloves are considered reusable gloves because they can be used multiple times prior to disposal. For example, homemakers may reuse the same pair of household gloves to protect their hands from harsh cleaning solutions or just while doing dishes. Likewise, gardeners or plant service workers may reuse gloves when spraying plants with fungicides or other garden chemicals.

It is desirable that the gloves (disposable and/or reusable) provide the necessary protection, are durable, flexible, do not cause irritation or allergy problems to those in contact with the article, are not tacky, are easy to don, and are comfortable to wear. Unfortunately, sometimes the desirable characteristics are not achieved.

As is known in the art, disposable gloves (and reusable gloves as well as other flexible elastomer articles) are thin and flexible and are manufactured from a variety of polymeric materials herein throughout referred to as "elastomer(s)" or "elastomer material(s)" or "raw material(s)". These elastomers may be considered a natural rubber as with natural rubber latex (NRL) or a synthetic rubber, or a plastic and include, but are not limited to, a synthetic polyisoprene, a chloroprene (including Neoprene-homopolymer of the conjugated diene chloroprene), a polyurethane (PU), a polyvinyl chloride (PVC), a styrene butadiene styrene (SBS), a styrene isoprene styrene (SIS), a silicone, a butadiene methylmethacrylate, an acrylonitrile, a styrene ethylene butylene styrene (SEBS), an acrylate-based hydrogel, any other elastomer that can be suspended into an emulsion, any other elastomer that is suspendable, soluble or miscible in a solution or plastisol, and combinations thereof.

As is known in the art, disposable gloves (and reusable gloves) are manufactured of elastomer(s) as single layer gloves or multi-layer gloves. A single layer glove has one layer having a single or blended (or mixture of) elastomer material therein. The one layer has an outer surface (or distal surface) and an opposite wearer-contacting surface. The wearer-contacting surface may have a material coated, dusted, sprayed or otherwise adhered thereon which functions to detackify the article during processing preventing sticking together in storage and/or to facilitate donning of the gloves by serving as a donning agent and providing enhanced lubricity on the wearer contacting surface thereby reducing frictional forces.

The multi-layer glove has more than one layer. One type of multi-layer glove is a bilaminar glove, which has two layers, namely a first layer and a second layer. The two layers are of similar or dissimilar elastomer(s). The first layer is a substrate layer having an elastomeric material and a distal surface and the second layer is a layer having a wearer-contacting surface. The bilaminar glove is commonly manufactured to have the thickness and the flexibility of the single layer glove. The materials used in the flexible disposable gloves or reusable gloves (collectively "gloves") and other flexible articles are elastomers compoundable as emulsions, solutions or plastisols wherein the elastomers are suspendable, soluble or miscible. For example, the materials used in the second layer of the bilaminar gloves are known in the art. See U.S. Pat. No. 3,286,011 to Kavalir et al., which discloses a mixture of an elastomer latex and a latex of a resin dipped on an elastomer latex to form an adherent elastomer-resin film on the elastomer article.

Other types of multi-layer gloves may have three or more layers, with one layer bearing the wearer contacting surface, and another layer bearing the distal surface with one or more intervening layers between the two layers having the wearer contacting surface and distal surface. Similarly, other flexible elastomer articles may have one or more layers of elastomer (or mixtures of elastomers) with one layer having the wearer-contacting surface and the same layer (if a single layer) or another layer having the distal surface (if a multi-layer article).

Some known in the art methods of making flexible elastomer gloves and glove materials are for example, U.S. Pat. No. 6,465,591, to Lee; U.S. Pat. No. 6,440,498, to Scholar; U.S. Pat. No. 6,423,328, to Chou; U.S. Pat. No. 6,414,083, to Plamthottam; U.S. Pat. No. 6,391,409, to Yeh et al.; U.S. Pat. No. 6,380,283, to Perella, et al.; U.S. Pat. No. 6,369,154, to Suddaby; U.S. Pat. No. 6,347,408, to Yeh; U.S. Pat. No. 6,345,394, to Nakamura, et al.; U.S. Pat. No. 6,306,514, to Weikel, et al.; U.S. Pat. No. 6,288,159, to Plamthottam; U.S. Pat. No. 6,284,856, to Lee; U.S. Pat. No. 6,280,673, to Green, et al.; U.S. Pat. No. 6,274,154, to Chou; U.S. Pat. No. 6,254,947, to Schaller; U.S. Pat. No. 6,242,042, to Goldstein, et al.; U.S. Pat. No. 6,221,447, to Munn, et al.; U.S. Pat. No. 6,213,123, to Miller, et al.; U.S. Pat. No. 6,121,366, to Sharma; U.S. Pat. No. 6,066,697, to Coran, et al.; U.S. Pat. No. 6,031,042, to Lipinski; U.S. Pat. No. 6,019,922, to Hassan, et al.; U.S. Pat. No. 6,017,997, to Snow, et al.; U.S. Pat. No. 6,016,570, to Vande Pol et al.; U.S. Pat. No. 6,000,061, to Taneja, et al.; U.S. Pat. No. 5,997,969, to Gardon; U.S. Pat. No. 5,993,923, to Lee; U.S. Pat. No. 5,985,955, to Bechara, et al.; U.S. Pat. No. 5,974,589, to Pugh et al.; U.S. Pat. No. 5,965,276, to Shlenker, et al.; U.S. Pat. No. 5,910,533, to Ghosal, et al.; U.S. Pat. No. 5,900,452, to Plamthottam; U.S. Pat. No. 5,881,387, to Merovitz, et al.; U.S. Pat. No. 5,881,386, to Horwege et al.; U.S. Pat. No. 5,877,244, to Hoover, et al.; U.S. Pat. No. 5,869,072, to Berry; U.S. Pat. No. 5,851,683, to Plamthottam, et al.; U.S. Pat. No. 5,833,915, to Shah; U.S. Pat. No. 5,807,941, to Tsuji et al.; U.S. Pat. No. 5,742,943, to Chen; U.S. Pat. No. 5,741,885, to Dove; U.S. Pat. No. 5,712,346, to Lee; U.S. Pat. No. 5,708,132, to Grimm; U.S. Pat. No. 5,700,585, to Lee; U.S. Pat. No. 5,691,446, to Dove; U.S. Pat. No. 5,691,069, to Lee; U.S. Pat. No. 5,682,613, to Dinatale; U.S. Pat. No. Re. 35,616, to Tillotson, et al.; U.S. Pat. No. 5,651,995, to Oyama et al.; U.S. Pat. No. 5,644,798, to Shah; U.S. Pat. No. 5,620,773, to Nash; U.S. Pat. No. 5,614,202, to DeFina; U.S. Pat. No. 5,612,083, to Haung et al.; U.S. Pat. No. 5,601,092, to Miller, et al.; U.S. Pat. No. 5,598,850, to Miller, et al.; U.S. Pat. No. 5,570,475, to Nile et al.; U.S. Pat. No. 5,568,657, to Cordova, et al.; U.S. Pat. No. 5,483,697, to Fuchs; U.S. Pat. No. 5,459,879, to Fuchs; U.S. Pat. No. 5,458,936, to Miller, et al.; U.S. Pat. No. 5,444,121, to Grennes, et al.; U.S. Pat. No. 5,407,715, to Buddenhagen, et al.; U.S. Pat. No. 5,405,690, to Hirakawa; U.S. Pat. No. 5,405,666, to Brindle; U.S. Pat. No. 5,395,666, to Brindle; U.S. Pat. No. 5,370,915, to Hirakawa; U.S. Pat. No. 5,284,607, to Chen; U.S. Pat. No. 5,272,771, to Ansell, et al.; U.S. Pat. No. 5,215,701, to Gould, et al.; U.S. Pat. No. 5,112,900, to Buddenhagen, et al.; U.S. Pat. No. 5,088,125, to Ansell, et al.; U.S. Pat. No. 5,020,162, to Kersten, et al.; U.S. Pat. No. 5,014,361, to Gray; U.S. Pat. No. 5,001,354, to Gould et al.; U.S. Pat. No. 4,954,309, to McGlothlin, et al.; U.S. Pat. No. 4,917,850, to Gray; U.S. Pat. No. 4,696,065, to Elenteny; U.S. Pat. No. 4,575,476, to Podell, et al.; U.S. Pat. No. 4,548,844, to Podell et al.; U.S. Pat. No. 4,499,154, to James, et al.; U.S. Pat. No. 4,482,577, to Goldstein, et al.; U.S. Pat. No. 4,463,156, to McGary, Jr., et al.; U.S. Pat. No. 4,390,492, to Kurtz; U.S. Pat. No. 4,371,988, to Berend; U.S. Pat. No. 4,340,348, to Kurtz; U.S. Pat. No. 4,302,852, to Joung; U.S. Pat. No. 4,251,574, to Berend; U.S. Pat. No. 4,186,445, to Stager; U.S. Pat. No. 4,185,330, to Stager; U.S. Pat. No. 4,070,713, to Stockum; U.S. Pat. No. 4,061,709, to Miller et al.; U.S. Pat. No. 3,942,193, to Pugh; U.S. Pat. No. 3,933,723, to Grenness; U.S. Pat. No. 3,813,695, to Podell, Jr. et al.; U.S. Pat. No. 3,397,265, to H. N. Ansell; U.S. Pat. No. 3,286,011, to Kavalir et al.; U.S. Pat. No. 3,225,360, to Keilen, Jr., et al.; U.S. Pat. No. 3,059,241, to O'Brien, et al.; U.S. Pat. No. 3,025,403, to Belknap, et al.; U.S. Patent Application Publication No. 2002/0110584, to Chou; U.S. Patent Application Publication No. 2002/0025335, to Chou; and U.S. Patent Application Publication No. 2001/0048937 A1, to Chou; PRC (Peoples Republic of China) ZL 95 2 22651.0 (Applicant: Gin Bao Shan enterprises Co. Ltd.), all of which are hereby incorporated herein by reference.

As is known in the art, the ASTM, (American Society for Testing and Materials, ASTM International, West Conshohocken, Pa., USA) and ISO (International Organization for Standardization, Geneva, Switzerland) provide standard specifications for disposable and reusable gloves. The standard specifications include performance requirements such as, but not limited to, freedom from holes, physical dimensions, physical properties, and total and/or antigen protein content. The standards include, but are not limited to, ASTM D 3577-01a$^{e2}$ "Standard Specification for Rubber Surgical Gloves", ASTM D 3578-01a$^{e2}$ "Standard Specification for Rubber Examination Gloves", ASTM D $_{5250}$-00$^{e4}$ "Standard Specification for Poly(vinyl chloride) Gloves for Medical Application" and ASTM D 6319-00a$^{e3}$ "Standard Specification for Nitrile Examination Gloves for Medical Application", ISO 10282:2002(E) "Single-use sterile rubber surgical gloves-Specification", ISO 11193:2002(E) "Single-use medical examination gloves-Part 1: Specification for gloves made from rubber latex or rubber solution", ASTM F 1671-97b "Standard Test Method for Resistance of Materials Used in Protective Clothing to Penetration by Blood-Borne Pathogens Using Phi-X174 Bacteriophage Penetration as a Test System", ASTM D 5151-99 "Standard Test Method for Detection of Holes in Medical Gloves", ASTM D 6499-00 "Standard Test Method for The Immunological Measurement of Antigenic Protein in Natural Rubber and its Products", ASTM D 412-98a "Standard Test Methods for Vulcanized Rubber and Thermoplastic Elastomers—Tension", ASTM D 4679-02 "Standard Specification for Rubber General Purpose, Household or Beautician Gloves", ASTM D 5712-99 "Standard Test Method for The Analysis of Aqueous Extractable Protein in Natural Rubber and Its Products Using the Modified Lowry Method", ASTM D 573-99 "Standard Test Method for Rubber—Deterioration in an Air Oven", ASTM D 6124-01 "Standard Test Method for Residual Powder on Medical Gloves", ASTM D 6355-98 "Standard Test Method for Human Repeat Insult Patch Testing of Medical Gloves", and ASTM D 3767-01 "Standard Practice for Rubber—Measurement of Dimensions", all of which are hereby incorporated herein by reference.

The gold standard elastomer for flexibility and comfort in disposable medical and industrial gloves (reusable gloves and other flexible articles) since the turn of the last century has been NRL which is harvested from the rubber tree Hevea brasiliensis. The NRL is synthesized within the cytoplasm of the laticifer cell of the rubber tree by a series of enzymes bathed in a complex milieu of minerals, amino acids, proteins, lipids, polysaccharides, etc., e.g., collectively referred to herein as "botanical contents". The liquid NRL harvested from the tree including the aforementioned botanical contents from the laticifer cells is then compounded or blended with a variety of processing chemicals. It is this blended NRL emulsion that is coagulated on the surface of a hand shaped former (in the case of glove manufacture) by a process known in the art as "dipping" (other flexible articles may be produced by dipping, molding or extrusion). Depositing the NRL emulsion evenly on the surface of the former is accomplished by pre-treating the former with a chemical anticoagulant (typically calcium nitrate or similar salt). The anticoagulant is applied to the former by dipping and is then oven dried.

The result is a fine salt crystal layer over the surface of the former. The salt layer thickness and composition together with the emulsion viscosity, NRL particle concentration, and dwell time in the NRL emulsion tank determine the thickness of the finished glove. This salt pretreated former then dips into the liquid NRL emulsion tank. The presence of the anticoagulant on the surface initiates coagulation of the NRL emulsion. As the former is removed from the NRL dip tank emulsion, the coagulation is not 100% complete. The non coagulated NRL begins to flow due to gravitational forces.

For this reason most machines are designed so the former immediately begins rotating on an axis parallel to the length of the former and completes a 90 to 180 degree rotation from the base of the former before entering the vulcanization ovens. The former rotation is trying to manage the unwanted flow of the yet uncoagulated NRL emulsion in order to minimize thickness variability in the finished product. Poor coordination of coagulation chemistry, emulsion viscosity, NRL density and rotation patterns of the formers produces a glove which when blown up shows a river like pattern where thicker rubber tributaries can be seen migrating from areas where there was pooled uncoagulated NRL which flowed randomly before coagulating. This uncontrolled flow produces finished products with thin and thick spots (non-uniformity of article layer, e.g., here the glove layer) which have increased vulnerability to breakage in use, greater susceptibility to oxidative damage in storage and are cosmetically less pleasing to the user. Even with optimal coordination of the variables some flow of the NRL occurs prior to coagulation producing variability of thickness of the finished product particularly at the finger tips.

Accordingly if a material could be selected that imparted thixotropic properties which could minimize this unwanted gravitational flow of the uncoagulated NRL without compromising the other variables of the process, an advantageous result of providing a more consistent thickness could be achieved with the finished product. The aforementioned methods of depositing a NRL emulsion on a former and the problem associated with production of a uniform article layer are also associated with other elastomers which can be suspended into an emulsion. In addition to NRL, such elastomers include a synthetic polyisoprene, a chloroprene, a PU, an acrylonitrile, a butadiene methylmethacrylate, an SBS, an SIS, an SEBS, a silicone, an acrylate-based hydrogel, any other elastomer that can be suspended into an emulsion, and mixtures thereof (all of which are currently commercially available as an emulsion with the exception of SBS, SIS, SEBS). If said material could be added to other elastomers, unwanted flow of the uncoagulated, unpolymerized or undried emulsions would result in a finished article (e.g. glove or other flexible elastomer article) with a more uniform thickness.

In 1986, OSHA published the Universal Bloodborne Pathogen Guideline for the specific purpose of minimizing the risk of the transmission of infection from patient to employee in the context of delivering healthcare. AIDS and Hepatitis B were of particular concern. The wearing of single use disposable gloves was a key part of this guideline and resulted in an exponential increase in both the frequency and duration of use of NRL gloves. An unfortunate consequence was a significant increase in the incidence of glove allergies (for a discussion of allergy problems, see, Hamann et al. "Allergies Associated with Medical Gloves—Manufacturing Issues" (1994) Occupational Dermatoses, Vol. 12, No. 3, pp. 547-599, incorporated by reference herein). Prior to glove users developing particular life threatening IgE specific antibodies against antigenic proteins originating from the laticifer cytoplasm of the rubber tree, a significant proportion of the laticifer cell cytoplasmic contents persisted in a finished NRL glove.

In the early nineties, in an effort to reduce the antigenic protein concentration in NRL gloves, processes were developed to remove or reduce the NRL botanical contents within the emulsions used to produce NRL products. Unfortunately, the broad variety of cytoplasmic contents that were now being removed contained natural botanical waxes, lipids and polysaccharides which synergistically functioned as plasticizers. These natural plasticizers affected the modulus (softness) of the finished product and allowed for a strong, yet supple glove. A lower modulus product is preferred by glove users because of its relation to the comfort and fit of the finished article. This user preferred softness of an NRL glove is compromised by the removal of the botanical contents and is impossible to replicate with synthetic elastomers.

Furthermore, the minerals, amino acids, proteins, lipids, waxes, polysaccharides, together with hundreds of additional unique botanical molecules (botanical contents) also function as excellent emulsifiers to assist in the optimal uniform distribution of the NRL particles in a dip tank making the deposition of a uniform film on the porcelain former easier. In addition, numerous naturally occurring antioxidants (amino acids, proteins, etc.) are available in the botanical contents that serve to protect the vulnerable unsaturated carbon bonds of the NRL by scavenging for free radicals throughout the useful life of the product. These molecules bloom to the surface over time and function as competitive inhibitors to the destruction of the NRL unsaturated bonds. Oxidized glove surfaces increase breakage while donning and during use. While removal or inactivation of the antigenic proteins has been necessary, the disadvantage has been the simultaneous elimination of the many benefits the remaining molecules of the botanical extract provide.

Accordingly if the botanical contents of the laticifer cells could be replaced in the NRL emulsion by a material without cross reactive antigenic proteins, the benefits of a more stable dipping emulsion with improved flow properties would be realized and a finished article with lower modulus and improved oxidative protection would be restored. If the material could be chosen which also contained dermatologically therapeutic components, the finished product would be enhanced. Furthermore, if the material could be added to synthetic elastomers used to produce gloves (or other flexible elastomer articles), the physical properties would have the ability to more closely mimic the preferred attributes of NRL.

Flexible elastomer articles, like disposable gloves, are frequently changed by the wearer during the day between patients or between procedures or activities. Allergy and irritation potential of a finished glove has been exacerbated by common glove manufacturing practices of using vulcanizing accelerators, antioxidants, cornstarch powder and other additives as means to speed production, ease donnability, prevent tackiness and enhance durability during the storage and useful life of the glove. In addition, since disposable gloves cover the hand, moisture (perspiration) is trapped beneath the glove, contributing to hand dermatitis. As a result, in excess of 20% of healthcare providers struggle with an allergic or irritant contact dermatitis or the IgE mediated latex antigen hypersensitivity (Type I) thereby making these individuals more susceptible to infection.

Solutions to the tackiness and donning problems are coating the wearer-contacting surface with a powder, halogenation, or other surface treatments. (See U.S. Pat. No. 4,186,445 and U.S. Pat. No. 4,185,330, both to Stager, and U.S. Pat. No. 5,614,202 to DeFina.) Cornstarch is used because most polymers are intrinsically sticky on their surfaces causing a blocking affect which makes it difficult to don the glove without the powder. (Other powders used in the interior of the glove to lubricate the glove, include, but are not limited to, talcum powder, starch dusting powder, polyglycolic acid powder, insoluble sodium metaphosphate powder, magnesium carbonate, oat starch and granular vinyl chloride polymer.) The powder may provide comfort to the wearer's hand as the hand moisture builds up within the glove as the glove is used but conversely may also act to dry, abrade and irritate the user's skin.

Although many glove users apply lotions and creams to moisturize their hands, these emollients frequently are oil-based which deleteriously affects an NRL glove. Further, these creams and lotions often contain similar antigenic chemicals and serve to exacerbate the skin problems.

It has also been shown that the antigenic proteins bloom to the surface of the NRL glove (or other flexible article) and migrate into the powder particles which then serve as vehicles to carry the antigen. This has been shown to be most problematic as an aerosolized particle delivered during breathing to the immunoactive tissue of the nasopharynx and bronchial tree where sensitization and elicitation of Type I NRL reactions can be initiated. In addition, glove powders can cause skin irritation and exacerbate contact allergies, therefore, the reduction or elimination of glove powders help glove users maintain a healthy dermal barrier and assure optimal protection against pathogens and contaminants which is the intended purpose of the glove.

The need to eliminate or minimize residual glove powder has led to the development of various powder removal processes and of alternative glove coatings. To remove unwanted powders, gloves are sometimes treated to a chlorination and neutralization process. Although these processes remove unwanted powder they also halogenate the glove surface and deleteriously affect the physical properties of the glove by accelerating the oxidation process by cleaving the unsaturated carbon bonds of the NRL polyisoprene chain, thus decreasing the shelf life and the softness of the glove.

The chlorination treatment of the glove may be used with or without the additional coating or lubricant composition treatment (see U.S. Pat. No. 5,742,943 to Chen for use of a lubricant composition post chlorination, where the lubricant composition has a first and a second composition, where the first composition comprises an acetylenic diol and at least one compound selected from the group consisting of an organo-modified silicone, an amino-modified silicone, and 1-hexadecylpyridiniuni chloride monohydrate, and the second composition comprises 1-hexadecylpyridium chloride monohydrate and at least one compound selected from the group consisting of an organo-modified silicone, an amino-modified silicone, and an acetylenic diol).

The art has responded to the problems associated with powder by preparing powderless gloves by the use of alternative lubricants, such as, polymeric lubricant coatings which are bonded to the tissue-contacting surface of the glove or are adhered to the elastomer, NRL (natural or synthetic) or plastic itself (See, for example, U.S. Pat. No. 4,548,844 to Podell et al. flexible rubber article with an interior lining of hydrophilic plastic material, preferably a hydrogel plastic material and U.S. Pat. No. 3,813,695 to Podell, Jr. et al. flexible glove with inner layer of a hydrophilic plastic material; U.S. Pat. No. 6,019,922 to Hassan et al. dip coating over an elastomer layer formed of an antiblocking composition comprising a polymer/co-polymer (such as an anionic aliphatic polyether polyurethane, or a co-polymer of vinylidene chloride/methyl acrylate, or natural rubber polymer), a high density polyethylene particle and a wax (such as a mixture of carnuba wax/paraffin wax); U.S. Pat. No. 5,395,666 to Brindle, use of porous, absorbent microparticles, preferably silica, added to a binder material having good adhesion to both an elastomeric substrate and to the microparticles; U.S. Pat. No. 5,881,386 to Horwege et al. a polyester polyurethane having a texturizing agent selected from the group consisting of diatomaceous earth, silica, glass beads and calcium carbonate, is adhered to a plasticized polyvinyl chloride resin film; U.S. Pat. No. 5,974,589 to Pugh et al. use of high density substantially linear hydrocarbon polymer, (such as polyethylene, polypropylene, polymethylene, paraffin, low density polyethylene, or a mixture thereof) to adhere to the surface of a latex article such as a glove; U.S. Pat. No. 5,570,475 to Nile et al., use of polymers on the hand contacting surface (such as, copolymers of a vinyl alkyl ether and a maleic ester or copolymers, of an alkylene and a maleic ester, or of copolymers of vinyl methyl ether and a maleic ester, or polymers of a butyl half ester of polyethylene/maleic acid, or a butyl half ester of polystyrene/maleic acid, of a partly esterified poly(styrene/maleic acid)) or polymers sold under the name SCRIPTSETS (available from Monsanto) to form a polymer layer on a natural or synthetic elastomer surface, with optional use of surfactant (cetyl pyridinium chloride) treatment, with or without use of silicones. Others have used different materials to form the glove, e.g., see U.S. Pat. No. 4,061,709 to Miller et al. for silicone rubber gloves.

Coating the gloves with alternative lubricants (glove coatings) present challenges because coatings are difficult to apply to a glove with a dip, spray, spray and tumble (spray/tumble), or soaking process. Because of the relative hydrophobicity of the surface of most gloves, the coatings tend to bead and concentrate in dependent areas of the glove resulting in uneven application of the coating.

For an example of a spray deposition process to impart an interior texture to the flexible glove see U.S. Pat. No. 6,016,570 to Vande Pol et al. Others have used multiple layers having a first layer of natural rubber or polyurethane, chloroprene, styrene/butadiene copolymer, nitrile latex, a second layer of natural rubber, polyurethane, poly(acrylamide-acrylic acid, sodium salt) and polyethyleneoxide, and a third wearer-contacting layer of acrylic copolymer and flurocarbon telomer resin, or alternatively a first layer of plastisol polyvinyl chloride (PVC) and coating this with the aforementioned wearer contacting layer, e.g., see U.S. Pat. No. 5,612,083 to Haung et al. Other bilaminar (two-layer) glove processes include PRC Patent ZL95 2 22651.0 disclosing a powder free process of manufacturing PVC gloves where a polyvinyl chloride substrate is given a slip surface treatment in a water base process or in an oil-base process. In the water base process, a water based silicone oil and catalyst form a film coating on the PVC substrate. In the oil base process, a polyester having good water solubility is used for the polyurethane epoxy along with a mixture of methy-ethyl-ketone/isobutyl-ketene and isopropyl alcohol to form the film coating on the PVC substrate.

Accordingly if a coating material could be chosen for application to a glove surface (or other flexible article surface) which produces acceptable donning attributes without the need for cornstarch as a donning agent, the transmission of the NRL antigenic protein would be minimized. If the thixotropic properties of the coating material were such that the coating functioned more like a liquid biopolymer, it would reduce the beading and pooling of the coating, and allow a uniform coating to be applied over all the glove (or other flexible article), and the product would be improved. If the coating material uniformly distributed could also simultaneously optimize moisture homeostasis between the glove and epidermis of the wearer to minimize irritant contact dermatitis from the extremes of dryness and wetness, a contribution would be made in reducing the risk of infection of damaged skin. If said uniformly distributed coating material also partially solubilizes during use and delivers therapeutically important molecules to mitigate the risks of irritant and contact dermatitis, the user will benefit from added protection. If the coating material also functions as a microbicide, an additional important level of protection could be provided if the glove were to fail and skin exposure to a pathogen occurred.

Furthermore, if said coating material could be applied to the surface of synthetic gloves and act as a donning agent by improving donning without powder, and decrease irritant and allergic contact dermatitis, and provide a microbicide in the case of glove (or other flexible article) failure, a contribution will be made. Also, if said coating material could balance moisture under the surface of the glove, a further contribution will be made.

U.S. Pat. No. 6,274,154 and U.S. Pat. No. 6,423,328, both to Chou and both incorporated herein by reference, U.S. Patent Application Publication No. 2001/0048937 A1, U.S. Patent Application Publication No. 2002/0025335 A1, and U.S. Patent Application Publication No. 2002/0110584 A1, all to Chou and all three of which are incorporated herein by reference, disclose a flexible single layer disposable glove containing dehydrated Aloe vera on the wearer contacting surface and a method of manufacturing the glove. The method of manufacturing the gloves discloses the steps of: forming an NRL glove, turning the glove inside out, applying an aqueous solution of Aloe vera to the surface facing out, removing the liquid by a controlled dehydration process with heat tumble drying of the gloves and/or the use of forced heated air to provide a partially and preferably full or at least substantial dehydration of the Aloe vera solution in the gloves, and turning the glove right side out so the dehydrated coating of Aloe vera contacts the hand of the glove wearer.

When the gloves are worn, the dehydrated Aloe vera is dissolved by the moisture from the wearer's hand. Aloe vera is a plant, long looked to in folk medicine for skin care and has been used in skin care products for moisturizing the upper layers of the epidermis of the skin. (See U.S. Pat. No. 5,800,818 to Prugnaud et al.) Despite the advantages of using Aloe vera as a coating material, for glove manufacturers competing in the international glove industry, the cost of the Aloe vera becomes an important consideration in competing globally.

What is needed is a flexible elastomer article, such as a disposable or reusable glove, having materials incorporated within its elastomer matrix that serve as a stabilizer, a flow modifier, an emulsifier, a plasticizer, a humectant, and an antioxidant. As a stabilizer, the material should stabilize the emulsion of the elastomer(s) by maintaining dispersions of otherwise imiscible phases and inhibiting physical processes (e.g., sedimentation, trapping gas bubbles and the non-uniform dispersion of rubber particles) within the emulsion of the elastomer(s), allowing for a more uniform film deposition during the dipping process. Additionally, the material should function as a flow modifier by providing selected thixotropic properties that modify the rheology of the elastomer emulsion thereby decreasing unwanted flow of the emulsion when forming the article. The material should also serve as an emulsifier by actively reducing surface tension thereby improving film deposition at the time of dipping. The material should act as a plasticizer by lowering the modulus of the finished article resulting in a softer glove (or other article) with retained strength and improved wearer comfort. The material should act as a humectant by balancing moisture homeostasis thereby enhancing skin moisturizing properties, lubricity and donning characteristics of the flexible article. The material should act as an antioxidant preventing unwanted oxidation during manufacturing and improving the shelf life of the finished article by protecting the vulnerable unsaturated carbon bonds of the elastomer.

A need exists to provide a flexible elastomer article with improved shelf life having a wearer contacting surface with improved moisturizing properties, lubricity and donning characteristics, and which provides comfort to the wearer.

A need also exists to provide a more economical method of fabricating a flexible elastomer article with improved lubricity and donning characteristics, with improved shelf life and which provides comfort to the wearer.

Yet another need exists to provide a flexible elastomer article utilizing raw materials which yield cost saving to the manufacturer without compromising the attributes of the finished product and which provide decreased bioburden in the finished product.

SUMMARY OF THE INVENTION

The needs, disadvantages and limitations of the background art discussed above are overcome by the present invention. The present invention in one of its aspects provides a flexible elastomer article (herein also "article" or "flexible article") in which a material, preferably, a biopolymer additive, most preferably a botanical extract(s), having a polysaccharide therein, is incorporated into an elastomer matrix of a layer of the article, preferably the layer having a wearer-contacting surface. The botanical extract serves as a stabilizer, a flow modifier, an emulsifier, an antioxidant, a plasticizer, a humectant, a moisture regulator and a moisturizer. It is an advantage of the present invention that the botanical extract when added to an elastomer emulsion is characterized by stabilizing the emulsion of the elastomer(s) by maintaining dispersions of otherwise imiscible phases and inhibiting physical processes (e.g., sedimentation, trapping gas bubbles and the non-uniform dispersion of rubber particles) within the emulsion of the elastomer(s), thereby allowing for a more uniform film deposition during the dipping process. It is another advantage that the botanical extract acts as a flow modifier and provides thixotropic properties that modify the rheology of the elastomer emulsion thereby decreasing unwanted flow of the emulsion when forming the article. It is another advantage that the botanical extract functions as an emulsifier that actively reduces surface tension which improves film deposition at the time of dipping. It is another advantage that the botanical extract acts as a plasticizer that lowers the modulus of the finished article resulting in a softer glove with retained strength and improved wearer comfort. It is another advantage that the botanical extract acts as an antioxidant that prevents unwanted oxidation during manufacturing and improves the shelf life of the finished article by protecting the vulnerable unsaturated carbon bonds of the elastomer. It is another advantage that the botanical extract acts as a humectant which balances moisture homeostasis which enhances skin moisturizing properties. The botanical extract also serves to enhance lubricity and donning characteristics of the flexible article.

Another aspect of the present invention provides a non-Aloe vera coating material having a polysaccharide therein, that when applied as a coating of an elastomer article, is characterized by acting as a moisture regulator whereby adsorption and desorption isotherms of the polysaccharide optimize moisture homeostasis beneath a glove or other flexible elastomer article. It is an advantage of the present invention that the non-Aloe vera coating material when applied as a coating act as a lubricant to improve user comfort, application, utility and donning characteristics of the article. It is a another advantage that the non-Aloe vera coating material when applied as a coating function as a flow modifier that imparts thixotropic properties of a liquid biopolymer facilitating uniform distribution of the coating over the entire article delivering therapeutic molecules to the entire hand or other part of the user's anatomy to which the flexible article is applied. It is a another advantage of the present invention that the non-Aloe vera coating material impart a range of therapeutically relevant physiologic benefits including anti-microbial, wound healing, anti-inflammatory, analgesic and anti-aging (oxidation injury) properties.

In another aspect of the present invention, the article, having the botanical extract incorporated therein and/or having the non-Aloe vera coating applied thereon, may be either a single layer flexible elastomer article or a multi-layer flexible elastomer article. The article may be a glove, such as a single layer glove, or a multi-layer glove, including a bilaminar glove. The article may be a catheter, a stent, an incontinence device having a sheath or sheath type construction, a condom, a cervical cap, a diaphragm, a dental dam, an elastomer sheet, a balloon for use in a medical device, a sheath or a tube used for a medical device, or a finger cot.

Another aspect of the present invention provides a method of fabricating or making a low cost flexible elastomer article in which a botanical extract is incorporated into an elastomer emulsion and serves as a stabilizer, flow modifier, emulsifier, plasticizer, humectant and anti-oxidant. The botanical extract is compounded with one or more selected elastomers in an emulsion, solution or plastisol prior to vulcanization, polymerization, solution evaporation and/or fusing (depending on the selected elastomer(s)).

Yet another aspect of the present invention provides a method of applying, to a wearer-contacting surface of a flexible elastomer article, a non-Aloe vera coating material having a non-Aloe vera botanical extract, having a polysaccharide therein. The non-Aloe vera botanical extract serves as a moisture regulator, a lubricant, a donning agent, a flow modifier, and imparts a range of therapeutic benefits and comfort to the wearer. The non-Aloe vera botanical extract is applied post vulcanization, post polymerization, post evaporation of solution or post fusing.

For the aforementioned aspects of the present invention, the botanical extract has a polysaccharide therein. The polysaccharide may be derived from a natural plant material having a mucinous plant (or botanical) polysaccharide(s), and/or a laboratory produced polysaccharide. Botanical extracts derived from natural plant materials include one or more extracts of Aloe vera, Nopal, okra, kelp, tamarind, psyllium, carrageenan, chia, flax, carob, guar, xanthan, konjac, cassia, tara, karaya, ghatti, glucomannan, galactomannan or tragacanth.

The botanical extract is incorporated within the elastomer layer of the aforementioned flexible article. Preferably the botanical extract is incorporated within the elastomer layer forming the wearer-contacting surface.

The non-Aloe vera botanical extract includes a non-Aloe vera plant material having a mucinous plant (or botanical) polysaccharide and/or a non-Aloe vera laboratory produced polysaccharide. Non-Aloe vera botanical extracts are derived from non-Aloe vera plant materials and include one or more of an extract of Nopal, okra, kelp, tamarind, psyllium, carrageenan, chia, flax, carob, guar, xanthan, konjac, cassia, tara, karaya, ghatti, tragacanth, glucomannan, galactomannan, or a non-Aloe vera laboratory produced polysaccharide.

Finally, it is an objective that all of the aforesaid advantages be achieved without incurring any substantial relative disadvantage and with achieving cost savings.

Other advantages and features of the invention, together with the organization and manner of operation thereof, will become apparent from the following detailed description when taken in conjunction with the accompanying drawings wherein like elements have like numerals throughout the drawings. It is expressly understood that the drawings are for the purpose of illustration and description only, and are not intended as a definition of the limits of the invention.

DESCRIPTION OF THE DRAWINGS

These and other advantages of the present invention are best understood with reference to the drawings, in which:

FIG. 9 is a cross sectional view of a portion of a bilaminar glove with an interior surface coating and in which the material that the interior layer of the glove is made from includes at least one botanical extract;

FIG. 10 is a cross sectional view of a portion of a multi-layer glove with an interior surface coating and in which the materials that two layers of the glove are made from includes at least one botanical extract;

FIG. 22 is a cross section view of a portion of a multi-layer glove in which the material that a layer of the glove is made from includes at least one botanical extract;

FIG. 23 is a cross section view of a portion of a multi-layer glove with an interior surface coating and with the material that a layer of the glove is made from including at least one botanical extract;

DETAILED DESCRIPTION OF THE PREFERRED EMBODIMENT

Figure 1:
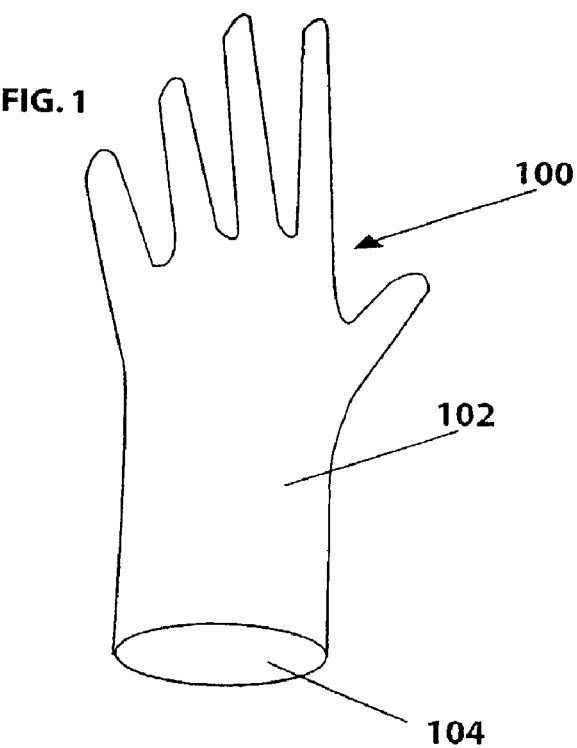
FIG. 1 is a perspective view of a glove showing an outer surface thereof and an inner or wearer contacting surface thereof.

This invention relates to the flexible elastomer articles and methods of making the same. More particularly, the present invention discloses two aspects which may be used in the manufacture of flexible elastomer articles, either separately or preferably, together (to form a third aspect). In a first aspect, the present invention discloses a material, preferably a biopolymer additive, most preferably a botanical extract(s) incorporated into an elastomer(s) emulsion, solution and/or plastisol in order to enhance the physical and therapeutic properties of a flexible elastomer article made from the elastomer(s) emulsions, solutions, and/or plastisol. In the second aspect, the invention relates to coating surfaces of a flexible elastomer article with a non-Aloe vera coating material which is fortified by additives known to protect, restore and moisturize mammalian skin or mucosa and to enhance ease of application or donnability of the article. A third aspect combines the first and second aspects of the present invention to produce an article having the botanical extract(s) incorporated into one or more layers of the article and having the non-Aloe vera coating material of the present invention on a surface of the article.

A flexible elastomer article (herein also "article" or "articles" or "flexible articles" or "flexible article" or flexible (articles)) of the present invention has at least one layer of an elastomer or blend (mixture) of elastomers therein. The article has a wearer contacting surface and an opposite distal surface. The distal surface is disposed as the most opposite surface to the wearer contacting surface. (The distal surface is disposed distal to the wearer contacting surface.) In some instances for certain articles, the distal surface is referred to as the outer surface or outer distal surface. However, for some articles, such as catheters, the distal surface may be the innermost surface.

The flexible article(s) of the present invention include, but are not limited to, a glove (reusable or disposable), a catheter, a stent or an incontinence device having a sheath or sheath type construction, a condom, a cervical cap, a diaphragm, a dental dam, an elastomer sheet, a sheath or tube for use with a medical device, a finger cot, or a balloon for use in a medical device (such as, but not limited to, a balloon used with a balloon catheter, a urinary catheter, a rectal catheter, an endotracheal tube, a feeding tube, or a cardiac catheter).

The flexible articles of the present invention are made from one or more elastomers (hereinalso "elastomer", "elastomers", "elastomer(s)", or "selected elastomer").

The botanical extract (hereinalso "botanical extract(s)" or "botanical extract") has a polysaccharide therein and is derived from a plant and/or is a laboratory produced polysaccharide. The botanical extract whether plant derived or laboratory produced share certain properties which will be discussed later. Suitable examples of botanical extracts of the present invention include extracts of the following materials: Nopal and/or Aloe vera, and/or kelp, and/or okra, and/or tamarind, and/or psyllium, and/or carrageenan, and/or chia, and/or flax, and/or carob, and/or guar, and/or xanthan, and/or konjac, and/or cassia, and/or tara, and/or karaya, and/or ghatti, and/or tragacanth, and/or glucomannan, and/or galactomannan, and/or a laboratory produced polysaccharide. The aforementioned botanical extracts may be combined or used individually in the present invention. The botanical extract may be referred to as a "mucilage" or a "gum" or a "mucinous polysaccharide". The botanical extract may exist commercially as an extract, a powder, a gel, or in other ways known in the industry.

In the first aspect, an elastomer raw material, e.g., an elastomer emulsion, solution, or plastisol is compounded with the addition of one or more of the aforementioned botanical extracts. The botanical extract is added to the elastomer raw material in a compounding process prior to vulcanization, solvent (or solution) evaporation, fusing or polymerization. The emulsion, solution or plastisol of the elastomer compounded with the botanical extract is subsequently vulcanized, evaporated/dried, fused or polymerized to incorporate the botanical extract into one or more layers of the finished flexible article. This is also referred to as incorporating the botanical extract into a matrix of the elastomer (hereinalso, "the elastomer matrix"). The botanical extract is incorporated into the elastomer making one or more layers of the flexible article. If the flexible elastomer article is of a single layer construction, or if the article is of multi-layer construction, the botanical extract preferably is disposed within the layer having a wearer contacting surface, but may be disposed within a layer having a non-wearer contacting surface in a multi-layer flexible article. The botanical extract enhances the physical and therapeutic properties of flexible elastomer article(s) made from the elastomer. For NRL, the botanical extract is selected to replace the NRL laticifer cell contents.

The selection of the elastomer(s), the selection of the botanical extract and concentration of the botanical extract to elastomer(s) will be discussed next. Where the elastomer is an elastomer that is suspended into an emulsion, specific examples of suitable elastomers include an NRL, a synthetic polyisoprene, a chloroprene (Neoprene), a PU, an acrylonitrile, a butadiene methylmethacrylate, an SBS, an SIS, SEBS, a silicone, and an acrylate-based hydrogel, any other elastomer that can be suspended into an emulsion, and mixtures thereof. Where the elastomer is an elastomer that is suspendable, soluble or miscible in a solvent (hereinalso, "solution") or a plastisol, specific examples of suitable elastomers include a silicone, a PU, an SIS, an SBS, an SEBS, a PVC, an acrylate-based hydroge, any other elastomer that is suspendable, soluble or miscible in the solution or the plastisol, and mixtures thereof.

The elastomers are so selected that the botanical extract is miscible or soluble in the emulsion of the elastomer and any mixtures thereof, or the botanical extract is suspendable, miscible or soluble in the solution or plastisol of the elastomer, and any mixtures thereof. The botanical extract selected is always suspendable, miscible or soluble in the elastomer, e.g., emulsion, solution or plastisol compounded with the botanical extract.

Where the elastomer is suspended into an emulsion, the botanical extract is characterized by stabilizing the emulsion of the elastomer(s) and maintaining dispersions of otherwise imiscible phases and inhibiting physical processes (e.g., sedimentation, trapping of gas bubbles and the non-uniform dispersion of rubber particles) within the emulsion of the elastomer(s). This allows for a more uniform film deposition during the dipping process. Further, the botanical extract is characterized by acting as a flow modifier, providing thixotropic properties that modify the rheology of the elastomer emulsion thereby decreasing unwanted flow of the emulsion when forming the article. The botanical extract is also characterized by its function as an emulsifier, actively reducing surface tension and improving film deposition at the time of dipping. The botanical extract is further characterized by functioning as a plasticizer that lowers the modulus of the finished article resulting in a softer glove with retained strength and improved wearer comfort and as a humectant, providing moisture homeostasis which enhances skin moisturizing properties, lubricity and donning characteristics of the flexible article. The botanical extract is also characterized by its antioxidant properties preventing unwanted oxidation during manufacturing and improving shelf life of the finished article by protecting the vulnerable unsaturated carbon bonds of the elastomer.

Preferred botanical extracts are Aloe vera extract and/or Nopal extract. These extracts are derived from the Aloe vera plant and the Nopal plant respectively. Both Aloe vera and Nopal are xerophytic plants which absorb and fix carbon dioxide at night requiring the use of a crassulacean acid metabolism (CAM). Unlike most plants which absorb carbon dioxide during the day in the chloroplast to make sugars through photosynthesis, the water conservation and homeostasis of Aloe vera and Nopal enables them to absorb and fix carbon dioxide in its cytosol at night and convert the carbon dioxide to malate. The malate is stored along with water and polysaccharides in special centralized vacuoles which make up 95% of the plant. During daylight the malate migrates from the vacuole back to the cytosol where it is decarboxylated into carbon dioxide and pyruvate. The carbon dioxide diffuses back into chloroplasts and together with light photons make sugars through photosynthesis (see, Wang et al., "Phloem Exudate Collected via Scale Insect Stylets for the CAM Species *Opuntia ficus-indica* under Current and doubled $CO_2$ Concentrations", Annals of Botany 75: 525-532, (1995), Table 3, p. 529). The majority of the sugars are polymerized into water soluble polysaccharides which are stored in the plant's vacuoles, cytosol and apoplast. Some of these polysaccharides are used for the conversion of carbon dioxide into malate. A proportion of these polysaccharides are synthesized into very large molecular weight molecules (up to 30 million daltons) in specialized mucilage cells. The large molecular weight polysaccharides have very unique water binding capacity and have a very important role in water conservation and storage for these plants. Unlike starch or cellulose which are found in plants, these polysaccharides are water soluble sugar biopolymers and are referred to as mucinous polysaccharides.

As discussed previously, the botanical extract selected for compounding with the selected elastomer has mucinous polysaccharides (hereinalso "polysaccharide" or "polysaccharides" or "polysaccharide(s) or "polysaccharide chain(s)" or "polysaccharide biopolymer") therein. Mucinous polysaccharides are large molecular weight polysaccharides without a protein attached thereto. For example, Nopal extract contains a high molecular weight fraction that include a molecular structure of up to 30,000 sugars and a molecular weight range of $2.3 \times 10^4$ to $1.5 \times 10^8$ daltons. The Nopal polysaccharide preferably contains varying proportions of L-arabinose (pyranose and furanose forms), D-galactose, L-rhamnose and D-xylose as the major neutral sugar units and also galactouronic acid. The primary structure is a molecule with a linear repeating core chain of $(1 \rightarrow 4)$ linked beta-D-galacturonic acid and alpha$(1 \rightarrow 2)$ linked L-rhamnose with trisaccharide side chains of Beta$(1 \rightarrow 6)$ linked D-galactose attached at O(4) of L-rhamnose residues. The galactose side residues present further branching in either O(3) or both O(3) and O(4) positions. For a Nopal extract, the composition of these polysaccharide chains is complex with at least 20 different types of oligosaccharides which have been identified.

Mucinous polysaccharides have polysaccharide chains. The chains of the mucinous polysaccharides of the botanical extracts are coiled and intertwined while yet a liquid. The tensile properties created by the unwinding and untangling of the intertwined polysaccharide slows the flow or migration of the elastomer emulsion giving additional time for coagulation, polymerization or drying further minimizing the thickness disuniformity of the elastomer film (see Paulsen et al. "Water soluble polysaccharides of *opuntia ficus-indica* CV "Burbanks Spineless", Phytochemistry 18 (1979) 569-571, Wang et al., "Phloem Exudaite Collected via Scale Insect Stylets for the CAM Species *Opuntia ficus-indica* under Current and doubled $CO_2$ Concentrations", Annals of Botany 75: 525-532, (1995); McGarvie et al. "The acid-labile, peripheral chains of the mucilage of the *Opuntia ficus-indica*", Carbohydrate Research, 94 (1981) 57-65; Mindt et al., "Cactaceae mucilage composition", Journal of Science and Food Agriculture, 1975, 26, 993-1000; Amin et al., "The mucilage of *opuntia ficus-indica* mill.", Carbohydrate research 15 (1970) 159-161; Parikh et al. "Cholla Gum I. Structure of the degraded cholla gum", Canadian Journal of Chemistry, Volume 44 (1966) 327-333; Parikh et al. "Cholla Gum II. Structure of the undegraded cholla gum", Canadian Journal of Chemistry, Volume 44 (1966) 1531-1539; Medina-Torres et al. "Rhelogical properties of the mucilage gum (*Opuntia ficus indica*)" Food Hydrocolloids 14 (2000) 417-424; Cardenas et al. "Rheology and Aggregation of Cactus (*Opuntia ficus-indica*) Mucilage in Solution", Journal of the Professional Association of Cactus Development, 2, 152-159 (1998); Saenz, "Processing technologies: an alternative for cactus pear (*Opuntia* spp.) fruits and cladodes", Journal of Arid Environments (2000) 46: 209-225; which disclosures are hereby incorporated herein by reference). These thixotropic properties are uniquely provided by a botanical extract of Aloe vera and/or Nopal, and/or okra, and/or kelp, and/or tamarind, and/or psyllium, and/or carrageenan, and/or chia, and/or flax, and/or carob, and/or guar, and/or xanthan, and/or konjac, and/or cassia, and/or tara, and/or karaya, and/or ghatti, and/or tragacanth, and/or glucomannan, and/or galactomannan.

Alternatively, the botanical extract is a laboratory produced polysaccharide(s) having the aforementioned properties, and may be used alone or in combination with one or more of the aforementioned plant derived botanical extracts. The laboratory produced botanical extracts of polysaccharides are manufactured by known in the art techniques, such as, but not limited to, refining, extraction, plant gene insertion into bacteria or other biotechnology processes, etc.

As previously mentioned, preferably the botanical extract for incorporation within a layer of elastomer of the article is Nopal extract and/or Aloe vera extract. In addition to the polysaccharides, Nopal extracts and certain other botanical extracts are known to contain waxes, amino acids and proteins. Furthermore, Nopal extracts are known to contain alkaloids, phenols, saponins, flavonoids, ascorbic acid, carotene, alpha amyrin, citric acid, maleic acidmethyl ester, glycoproteins, acetylsalicylic acid, sucrose and Beta sitosterol. The Beta sitosterol has demonstrated antihistiminic and anti-inflammatory properties, which assist in wound healing. The acetylsalicylic acid has known analgesic properties and the ascorbic acid has known anti-aging properties.

The botanical sources of Aloe vera are typically from, but are not limited to, the Aloe vera and Aloe barbadensis and other species of the Aloe plant. Hereinthroughout, the term "Aloe vera" includes the named species Aloe vera and Aloe barbadensis and other species of the Aloe plant, as is known in the art. The source of the Nopal (a.k.a. Cholla and Prickly Pear Cacti) extracts are obtained from any species of the *Opuntia, Nopalea* and *Consolea* genera (subfamily Opuntioideae), for example, but not limited to, *Opuntia ficus indica, Opuntia dillenii, Opuntia streptacantha, Opuntia engelmanii, Opuntia fulgida, Opuntia fulginosa, Nopalea auberi, Nopalea karwinskiana, Consolea rubescens* and *Consolea monoliformis*. The Nopal extract and the Aloe vera extract are commercially available from suppliers in liquids, gels, and powders. Preferably, the Nopal extract is made from the cladodes (pads) of the Opuntioideae plant(s).

The use of Nopal advantageously provides a substantial cost saving in the international glove industry. Extensive commercial cultivation of Nopal for food applications combined with a significantly greater yield per acre per year over Aloe vera combine to make it possible for commercial suppliers to offer water soluble Nopal extracts for less than half the cost of the commercial Aloe vera extracts. The use of Nopal in the present invention creates a competitive advantage in the international glove industry (and other flexible elastomer article industries) because of this substantial savings over Aloe vera. Other of the botanical extracts are commercially available as will be discussed later. As is known in the art, the polysaccharide compositions of the plant based botanical extracts (also the plant based non-Aloe vera botanical extracts) may vary due to growing condition, e.g., ambient $CO_2$, moisture, temperature, etc., and processing and storage conditions.

To prepare the elastomer compounded with the botanical extract for an elastomer where the raw material(s) is an elastomer emulsion, the botanical extract is added to the elastomer emulsion, in a quantity sufficient to serve as a stabilizer, a flow modifier, an emulsifier, a plasticizer, a humectant and an anti-oxidant. An example of an elastomer emulsion is NRL.

Where NRL is the elastomer selected for compounding, addition of the botanical extract(s) pre-vulcanization allows the botanical extract to be incorporated into the NRL matrix of the finished article during vulcanization, thereby protecting the unsaturated carbon bonds of the NRL. The addition of the water soluble botanical extracts of the preferred botanical extracts of Nopal and/or Aloe vera (and/or kelp, and/or okra, and/or tamarind, and/or psyllium, and/or carrageenan, and/or chia, and/or flax, and/or carob, and/or guar, and/or xanthan, and/or konjac, and/or cassia, and/or tara, and or karaya, and/or ghatti, and/or tragacanth and/or glucomannan and/or galactomannan) simultaneously replaces the waxes, lipids, amino acid and protein contents which function as a stabilizer, a flow modifier, an emulsifier, a plasticizer, a humectant and an anti-oxidant.

Furthermore, the aforementioned selected botanical extract(s) replace the broad spectrum of laticifer cell botanical contents in the NRL emulsion which were removed because of the NRL protein allergy epidemic (NRL antigen content). Replacing the laticifer cell contents in NRL with a botanical extract without cross-reactive antigenic proteins has a number of additional benefits. One benefit is the return of the benefits of colloidal stabilization of the NRL emulsion, thereby improving the dipping of a uniform NRL film thickness. Another benefit is the return of the antioxidant properties provided by a diverse range of amino acids and proteins, thereby protecting the vulnerable unsaturated carbon bonds of the NRL polyisoprene. Yet another benefit is the return of a lower modulus of the glove thereby providing a softer more comfortable glove with retained strength, resulting from the plasticizing of the NRL by the diverse plant molecules in the selected botanical extract including the waxes, lipids and polysaccharides. For non-NRL emulsions, the benefits provided by the botanical extract include the aforementioned functions of a flow modifier, an emulsifier, a plasticizer, a humectant, an antioxidant and/or therapeutic properties.

Alternatively, to prepare the elastomers compounded with the botanical extract for the elastomer where the elastomer raw material is made from a solution or plastisol, the botanical extract is required to be suspendable, soluble or miscible in the solution or plastisol and is added to the solution or plastisol. In this instance, specific examples of suitable elastomers include a silicone, a PU, a PVC, an SIS, an SEBS, an SBS, an acrylate-based hydrogel, any other elastomer wherein the botanical extract is suspendable, soluble or miscible in the solution or plastisol, and mixtures thereof. The introduction of the aforementioned selected botanical extract(s) to make the elastomer compounded with the botanical extract for a non-NRL elastomer provides the benefits of antioxidant and therapeutic properties as described above.

In the compounding process, the botanical extract is added to the elastomer raw materials in concentrations which preferably result in a glove or other flexible article which complies with and does not fall outside of the physical attributes called out in applicable ASTM and ISO specifications, for gloves (see standards supra) for the particular elastomer material and the target physical properties for the flexible articles (other ASTM, ISO, industry and/or regulatory standards, as is known in the art).

Thus, in making the flexible elastomer article of the present invention, the use of the aforementioned botanical extracts advantageously provides an optimal polysaccharide biopolymer addition to the elastomer, by stabilizing and maintaining dispersions within the emulsion of the elastomer, modifying flow through thixotropic properties that prevent unwanted flow of the emulsion, acting to emulsify or reducing surface tension allowing for a more uniform deposition of the elastomer film, by serving as an antioxidant that increases shelf-life of the finished article, by acting as a plasticizer and lowering the modulus of the finished article and improving wearer comfort, and by providing moisture homeostasis properties that enhance moisturizing properties, lubricity and donning characteristics of the flexible article thereby, producing a glove (or other flexible elastomer article) with a more uniform thickness and enhanced durability, functionality and comfort. In addition, the botanical extract advantageously contains therapeutic components having one or more of the qualities of wound healing, anti-inflammatory properties, anti-microbial properties, analgesic properties, and anti-aging properties. In the preferred embodiment, the botanical extract selected is an Aloe vera extract. Alternatively, the botanical extract selected is also preferably a Nopal extract. Alternatively, the botanical extract is preferably a mixture of an Aloe vera extract and a Nopal extract. Alternatively, the botanical extract is selected from the group of extracts of Aloe vera, Nopal, okra, kelp, tamarind, psyllium, carrageenan, chia, flax, carob, guar, xanthan, konjac, cassia, tara, karaya, ghatti, tragacanth, glucomannan, galactomannan, a laboratory produced polysaccharide, and mixtures thereof. The botanical extract is preferably water soluble.

As previously discussed, the elastomer compounded with the botanical extract may be formulated in a number of ways, e.g., via emulsion, solution or plastisol. In the preparation of the present invention for incorporating the botanical extract into the elastomer, the units of phr are used. Phr measures the concentration of the botanical extract in a finished article. (Also, see Table A1.2 of ASTM D 573-99 illustrating use of standard formulations of rubber compounds based on phr.) Phr is parts per hundred weight of rubber or in this invention, phr also means parts per hundred weight of elastomer. Phr is a measure of dry weight, used to reflect the botanical extract concentration in the finished article, e.g., weight of material, in this instance, botanical extract, per one hundred weight of elastomer. A concentration of botanical extract to elastomer ranges from about 0.2 to 5.0 phr but, preferably ranges from about 0.2 to 2.5 phr. Concentrated solutions of one or more of the water soluble botanical extracts of the present invention, are made and added to the elastomer emulsion, plastisol or solution during the well known compounding steps of flexible article (for example, glove) production. The elastomer that is prepared according to the compounding step is referred to as an elastomer compounded with the botanical extract.

The use of the phr unit rather than percent of botanical extract by volume is preferred because of the significant variability in the concentration of elastomer-to-water/solvent/plastisol in the raw materials from which the elastomer is produced. For example, for NRL, the rubber-to-water concentration per volume may vary by batch of raw material and by weather conditions, e.g. rain, drought, etc. Some shipments of liquid NRL (pre-compounding) may have high rubber to water ratios and others have low rubber-to-water content. For example, some elastomers may be shipped in concentrated solutions, e.g. 70% wt/volume to avoid shipping excess water that may be added back during the elastomer compounding phase of production. The addition of the botanical extract is tied to the total rubber (or other elastomer) concentration in the liquid emulsion, and not the volume of the water. In this way, one can assure a constant quantity of botanical extract in the finished flexible elastomer article. By using the phr designation of concentration, it makes it also possible to have variability in the process of adding the botanical extract to the elastomer emulsion, solution, or plastisol.

For example, for NRL, a density measurement may be made of an elastomer raw material to determine the density "d" (or specific gravity) of the elastomer in terms of gm/ml of elastomer (or other units of density). Knowing the volume "V" of the raw material one can easily calculate the weight $W_E$ of elastomer.

$$V \div d = W_E$$

Knowing the weight $W_E$ of the elastomer in the volume of elastomer, one can calculate the amount (weight) of the botanical extract ($W_{BE}$) needed for a specified phr.

Once the $W_{BE}$ (amount of botanical extract) is determined, a weight/volume percentage solution of botanical extract can be formulated, depending on the elastomer, the flexible article to be made and the process used. $W_{BE}$ is added to the elastomer raw material in a quantity sufficient to produce the specified phr in the finished flexible elastomer article. Where multi-layer flexible articles are made, the $W_E$ is based on the total weight of elastomers used in the different layers of the finished article and the above formulas can be easily modified. For other non-NRL (non-botanical source) elastomers where the weight of the elastomer is known, the weight of the botanical extract can be calculated by ratio to achieve the specified phr.

The botanical extract is typically prepared in water solution to be added to the elastomer. For example, a ten percent (10%) water solution of the botanical extract may be mixed as a practical concentration for rehydration of a powdered botanical extract. Each time a batch of elastomer is compounded, there could be variability in the rubber content (or other elastomer content or elastomer mixture content) of the inbound liquid raw materials which would make the volume of a ten percent (10%) concentration added to achieve a 1phr change. It could also happen that a more concentrated solution of the botanical extract would be prepared in order to achieve the target phr without a viscosity change of the emulsion, solution or plastisol exceeding or not being in conformance with the proprietary manufacturing parameters for making flexible elastomer articles of the type being produced.

Typically, in the present invention, the preferred range of the phr is about 0.2 to 2.5 for weight of botanical extract per hundred weight of elastomer. It is possible for the range to extend from about 0.2 to 5.0 phr, depending upon the article to be made and the proprietary process nuances. A higher phr may be necessary in certain processes where a post cure leach is performed to reduce the antigenic protein which concomitantly reduces too much of the botanical extract. Preferably, the range of phr of botanical extract to elastomer in the finished flexible article may differ from the stated ranges, but in any case, is in a quantity sufficient that the physical performance standards of the article, e.g., those designated in the ASTM and ISO standards (above) or equivalent standards or other allowable pre-market certification requirements, such as, but not limited to, FDA requirements, for gloves or other flexible articles are met. For example, an instance of exceeding the ASTM, ISO or other standards occurs where a phr is used which may produce a softer feeling product, but where the product fails a tensile strength standard of the ASTM, ISO, or other standard.

The performance standards, for example, for gloves, are physical requirements (also called "tensile properties" in the ISO Standards) and performance requirements, such as, freedom from holes, physical dimensions and tolerances, physical properties, powder-free residue, protein content, powder amount, etc. The performance requirements and physical requirements from the aforementioned ASTM and ISO specifications supra are herein incorporated by reference. Test methods for the physical requirement tests and performance requirements are conducted according to the appropriate ASTM, ISO, or other, known in the art, testing standards (see ASTM Standards supra) or other regulatory standards or other pre-market certification requirements. The physical requirements pertain to parameters before aging, such as, tensile strength and an ultimate elongation, stress at 500% elongation, and parameters after accelerated aging, such as, tensile strength and ultimate elongation. The botanical extract selected and used in the present invention is in a quantity sufficient in the finished article for the finished article to maintain, and to not fall outside the physical requirements of the ASTM, ISO and/or other known standards for the particular flexible article made. For gloves, ASTM and ISO physical requirements include, but are not limited to, physical requirements in physical requirement tables of the following publications: ASTM D 3577-01a$^{\epsilon 2}$—Table 3, ASTM D $_{5250}$-00$^{\epsilon 4}$—Table 3, ASTM D 6319-00a$^{\epsilon 3}$—Table 3, ISO 11193-

1:2002(E)—Table 3, ISO 10282: 2002(E)—Table 3, ASTM D 3578-01a$^{e2}$—Table 1, and ASTM D 4679-02—Table 3, all the disclosures of which are hereby herein incorporated by reference. Thus, a concentration of botanical extract in the flexible article of the present invention is an amount sufficient to optimize benefits without compromising the physical requirements and performance requirements-required by the applicable ASTM and/or ISO specifications, and/or other known standards and/or other known pre-market certification requirements for tensile strength, modulus, ultimate elongation, and aging, and/or for freedom from holes, physical dimensions, physical properties, powder-free residue, protein content and powder amount.

Where the article is a glove, the types of gloves include disposable gloves or reusable gloves, the glove may be an examination glove, a surgical glove, an industrial glove, a protective glove or a household glove. Flexible articles of the present invention include articles having a single or multiple layers of elastomer. Where the glove is the article, a single layer glove or a bilaminar glove (two layers) or a multi-layer glove is comprehended by the present invention. Where the glove is a single layer glove (or other single layer article), specific examples of the suitable elastomers include a NRL, a synthetic polyisoprene, a chloroprene, PU, an acrylonitrile, a butadiene methylmethacrylate, an SBS, an SIS, an SEBS, a silicone, an acrylate-based hydrogel, any other elastomer that could be suspended into an emulsion, and mixtures thereof. Thus, the single layer article (or glove) could be made of one or more of the aforementioned elastomers. The botanical extract for the single layer glove may be any one of or any mixture of the aforementioned botanical extracts. Preferably the botanical extract is an Aloe vera extract or a Nopal extract or both. A single layer of an elastomer may be achieved by multiple dipping of an article former into the same elastomer. In other words, a single elastomer (or mixture of elastomers) which is multi-dipped is considered herein to form a single layer elastomer article or one layer of a multi-layer elastomer article.

Where the glove is the bilaminar glove (or other two layer article) having a first layer having the distal (or outer surface) and a second layer having the wearer contacting surface, the first layer and the second layer may be made of a similar or a dissimilar elastomer(s) and the botanical extract is incorporated into at least one layer of the glove. For the layer of the glove into which the botanical extract is incorporated, the elastomer is any elastomer or combination of elastomers that can be suspended into an emulsion or any elastomer or combination of elastomers that is suspendable, soluble or miscible in a solution or a plastisol and wherein the botanical extract is soluble or miscible in the same emulsion, solution, or plastisol.

Specific examples of suitable elastomer(s) used for either the first layer or the second layer of a bilaminar glove include an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer or combination of elastomers that could be suspended into an emulsion, or any elastomer or combination of elastomers that is suspendable, soluble or miscible in a solution or a plastisol, and mixtures thereof. Thus, each layer of the two layer article could be made of a single elastomer or a mixture of the aforementioned elastomers. The botanical extract is soluble or miscible in the emulsion, solution, or plastisol of the elastomer for the layer of the glove into which the botanical extract is incorporated and the botanical extract is preferably any one of or a mixture of any of the aforementioned botanical extracts. The botanical extract is most preferably an Aloe vera extract or a Nopal extract or a combination of both Nopal extract and Aloe vera extract. In the most preferred embodiment, the bilaminar glove has a first layer of PVC and the elastomer selected for the second layer is PU and/or silicone. In the preferred embodiment the botanical extract is incorporated into the second layer of the glove.

Where the glove is a multi-layer glove (or other multi-layer article) the glove has a first layer having an outer surface, a layer having the wearer contacting surface and one or more layers disposed between the first layer and the layer having the wearer contacting surface. The botanical extract is in at least one layer of the glove (or article). Specific examples of suitable elastomers selected for each layer of the glove include an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer or combination of elastomers that could be suspended into an emulsion, any other elastomer or combination of elastomers that is suspendable, soluble or miscible in a solution or plastisol, and mixtures thereof. Thus, each layer of the multi-layered article could be made of a single elastomer or of a mixture (combination) of the aforementioned elastomers. The botanical extract is soluble or miscible in the emulsion, solution, or plastisol of the elastomer for the layer of the glove into which the botanical extract is incorporated and the botanical extract is preferably any one of or a mixture of any of the aforementioned botanical extracts. In the preferred embodiment, the botanical extract is an Aloe vera extract or a Nopal extract or both.

In the flexible article of the present invention and for the gloves of the present invention, the preferred botanical extract is derived from plant material and is one or more extracts of Aloe Vera, Nopal, okra, kelp, tamarind, psyllium, carrageenan, chia, flax, carob, guar, xanthan, konjac, cassia, tara, karaya, ghatti, glucomannan, galactomannan, or tragacanth. Yet alternatively, the botanical extract is a laboratory produced polysaccharide. Yet alternatively, the botanical extract is one or more of the aforementioned extracts derived from plant material and the laboratory produced polysaccharide.

In the second aspect of the present invention, a wearer contacting surface of the flexible elastomer article is coated to improve moisturizing characteristics and donnability with a non-Aloe vera coating material which is fortified by additives known to protect and restore mammalian skin. Hand sweating beneath a glove (or other flexible elastomer article) with chronic use is known to be a contributor to irritant contact dermatitis, see supra. The ability to reversibly absorb the perspiration without the abrasive properties of cornstarch is an advantage over the prior art. The improvement of moisturizing characteristics is a function of the water homeostasis after the flexible article is donned.

With regard to the second aspect, the non-Aloe vera coating material is placed upon a surface of the flexible elastomer article, preferably a wearer contacting surface, such as the inside of an article, most preferably the inside of a glove. The non-Aloe vera coating material is a non-Aloe vera mucinous botanical polysaccharide and/or a non-Aloe vera laboratory produced polysaccharide, (both polysaccharides collectively herein also referred to as "a non-Aloe vera botanical extract") having the aforementioned properties of the botanical extracts and preferable polysaccharides, and having a water weight gain of at least 110% determined by an adsorption isotherm performed at 35° C., thus, excluding Aloe vera extract. The non-Aloe vera laboratory produced polysaccharide is manufactured by known in the art techniques, such as, but not limited to, refining, extraction, plant gene insertion into bacteria or other biotechnology processes, etc. The non-Aloe vera coating material for coating the wearer contacting surface of the article is preferably a non-Aloe vera botanical extract that serves as a moisture regulator, a moisturizer, a lubricant/donning agent, a flow modifier and imparts a range of therapeutically relevant physiologic benefits including anti-microbial, wound healing, anti-inflammatory, analgesic and anti-aging (oxidation injury) properties.

In the preferred embodiment, the non-Aloe vera coating material is a non-Aloe vera botanical extract which is preferably fortified with one or more additives. In the preferred embodiment, the non-Aloe vera botanical extract used for the non-Aloe vera coating material on the inside of the glove or on a surface of the flexible article is Nopal extract. In the most preferred embodiment Nopal is used to make a solution of the non-Aloe vera coating material. The non-Aloe vera botanical extracts, e.g., polysaccharide sources include, but are not limited to Nopal extract, and/or okra extract, and/or kelp extract, and/or tamarind extract, and/or psyllium extract, and/or carrageenan extract, and/or chia extract, and/or flax extract, and/or carob extract, and/or guar extract, and/or xanthan extract, and/or konjac extract, and/or cassia extract, and/or tara extract, and/or karaya extract, and/or ghatti extract, and/or tragacanth extract, and/or glucomannan, and/or galactomannan, and/or laboratory produced non-Aloe vera polysaccharides. Specific examples of suitable additives to the botanical extract include one or more of Vitamin A, Vitamin E, Vitamin C, Vitamin $B_3$, Vitamin $B_5$, jojoba, rose hips, tea tree oil, flax seed oil, palm oil, and acetylsalicylic acid. (It is to be noted that flax extract is made from the hull of the flax seed and is not identical to flax seed oil which is made from the inside of the flax seed.)

For the non-Aloe vera surface coating material, the concentration range of the non-Aloe vera botanical extract may be a 5% to 20% solution (water and/or ethanol), but may be prepared in a 1% to 50% solution; more preferably an 8% to 12% solution is used; most preferably a 10% solution is used.

The non-Aloe vera coating material may also be expressed in units of phr of the non-Aloe vera botanical extract per hundred weight of elastomer in the finished product. The phr for the coating material may possibly be determined by industry standards or guidelines for a particular non-Aloe vera coating material in the finished flexible elastomer article. To calculate the phr for a surface coating, the density of the elastomer(s) and the elastomer concentration is calculated. Knowing the elastomer concentrations allows the calculation of appropriate quantity of non-Aloe vera botanical extract to be added to yield the prescribed phr. (Alternatively, if the weight of elastomer is known, and a phr selected, the weight of the non-Aloe vera botanical extract is calculated by ratio.)

The amount by weight of non-Aloe vera botanical extract is then suitably mixed into a water and/or ethanol solution and applied as a surface coating to a surface of the flexible article by spraying, tumbling, soaking, dipping and in other ways known in the art for applying a surface coating. The percentage concentration (or phr) of the non-Aloe vera botanical solution depends upon the type of application to the article and/or the drying conditions. The additive(s) may be added in usual amounts to meet content labeling requirements known in the industry.

The thixotropic properties of the polysaccharide biopolymer component of the most preferred Nopal extract (or the other aforementioned non-Aloe vera botanical extracts) makes it function as a liquid biopolymer making it possible to uniformly apply a coating with a dip, spray, tumble and spray, or soaking method and air or oven dry a uniform coating thickness on the surface of a chlorinated or non chlorinated glove, or other flexible article. Nopal has desirable sheer thinning properties providing "peeling" behavior in an increasing Nopal solution concentration (see Cardenas et al. supra). A quantity of Nopal extract (or other non-Aloe vera botanical extract) sufficient to reduce the rubber or plastic blocking and provide adequate lubriciousness when dry donning (not greater than 2500 g frictional donning forces using a load tester; Cote et al., 1998 Journal of Biomedical Materials Research, 43:331-337) is used in the present invention.

There is a distinction in wearer comfort between donnability due to the coating material and wearer comfort due to the moisturizing properties of the coating material, e.g., improvement of the perception of comfort caused by the water homeostasis after the flexible article is donned. The present invention advantageously improves the wearer comfort due to the moisturizing properties. This is best understood by the water sorption isotherms of the present invention. A sorption isotherm of an article (or material) shows the relationship between water activity and moisture content of the article (or material or compound) at equilibrium (or steady state) at constant temperature. The water activity can be expressed as relative humidity (RH) of the surrounding air. Typically the RH ranges from 5% to 95% (or higher, but less than 100% RH). The moisture content at equilibrium can be expressed as percentage weight gain (or loss) of the article (or material) due to picking up moisture or losing moisture to the surrounding air. The sorption isotherm can be expressed as a desorption isotherm or as an adsorption isotherm.

Desorption isotherms show the loss of moisture from the material equilibrating with the surrounding air. Desorption isotherms typically start at 95% RH (or higher, but less than 100% RH) and decrease to 5% RH. Adsorption isotherms illustrate the gain of moisture to the material equilibrating with the surrounding air. Adsorption isotherms typically start at 5% RH and increase to 95% RH (or higher, but less than 100% RH). The difference between the desorption isotherm and the adsorption isotherm is hysteresis. Hysteresis illustrates the phenomena where water is more easily absorbed at a given relative humidity and temperature than released; this is shown by the desorption isotherm being above the adsorption isotherm. This would mean a higher steady state weight for a particular sample at a particular relative humidity if the study began at 95% RH (or higher, but less than 100% RH) versus 5% RH. This is illustrated by silica crystals used as a desiccant to reduce humidity in packaging of small electronics where moisture is easily absorbed and tenaciously retained. The weight gain or weight loss is calculated at a given relative humidity at such time as a steady state (equilibrium) is reached. This means that no additional weight gain or loss occurs at the given relative humidity and temperature.

The adsorption-desorption isotherms of the cladode (whole leaf pad) of *Opuntia ficus* indica have been studied experimentally and compared with predictive mathematical models to study the influence of temperature on equilibrium moisture content. In the reported study, the cladode is dehydrated in a 50° C. drying oven for the adsorption isotherm and a fresh cladode is used for the desorption isotherm. The whole leaf pad is able to absorb up to 100% of its dry weight. (See, Lahsasni, et al., "Moisture adsorption-desorption isotherms of prickly pear cladode (*Opuntia ficus*) at different temperatures", Energy Conversion and Management 44 (2003) 923-936, the disclosure of which is herein incorporated by reference.)

Figure 25:
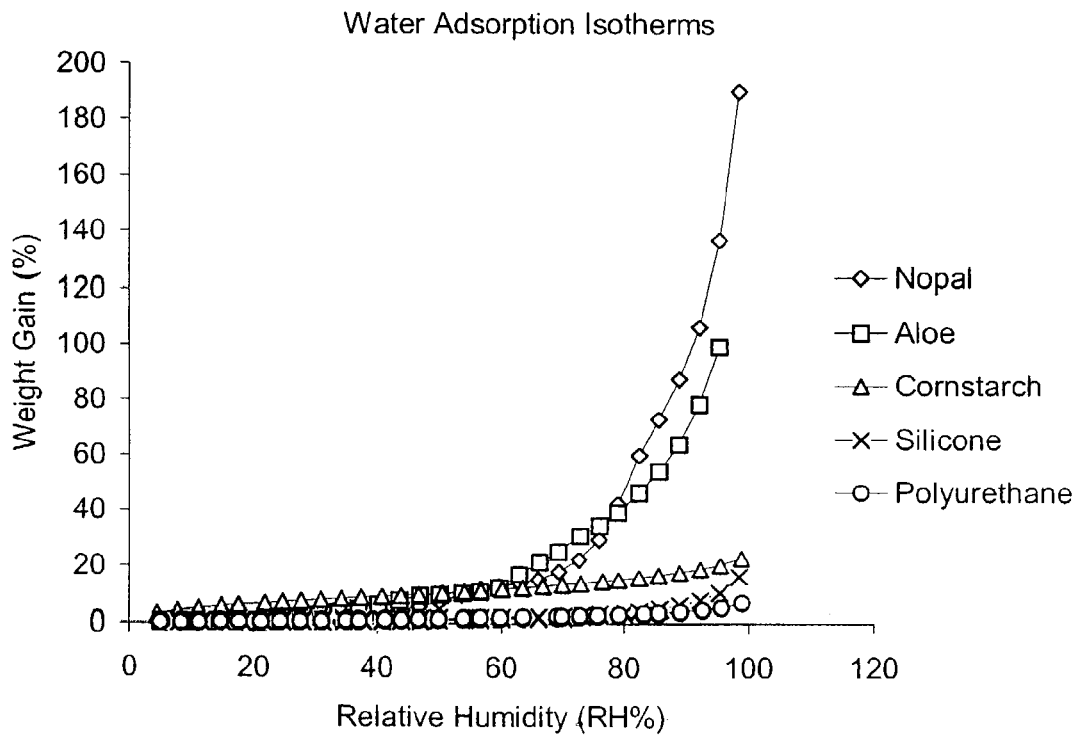
FIG. 25 is a water sorption isotherm overlay comparing adsorption isotherms of materials.

As best shown in FIG. 25, a comparison of the measured adsorption isotherms, an advantageous unexpected result was discovered when fill isotherms were performed on Nopal extract of the present invention and compared with the Aloe vera extract used for coating in the prior art and other known in the art coating materials. It was discovered that Nopal absorbs twice the moisture of Aloe vera at maximum relative humidity thereby illustrating the dramatic improvement of the present invention over the prior art coating materials.

Figure 29:
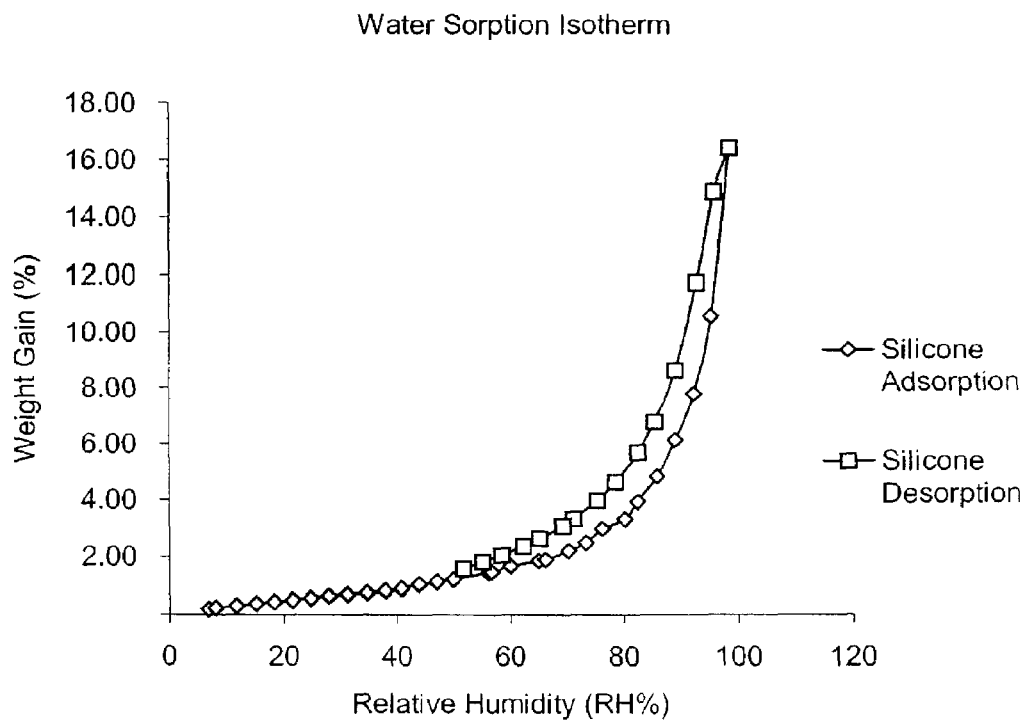
FIG. 29 is a water sorption isotherm of silicone powder.
Figure 30:
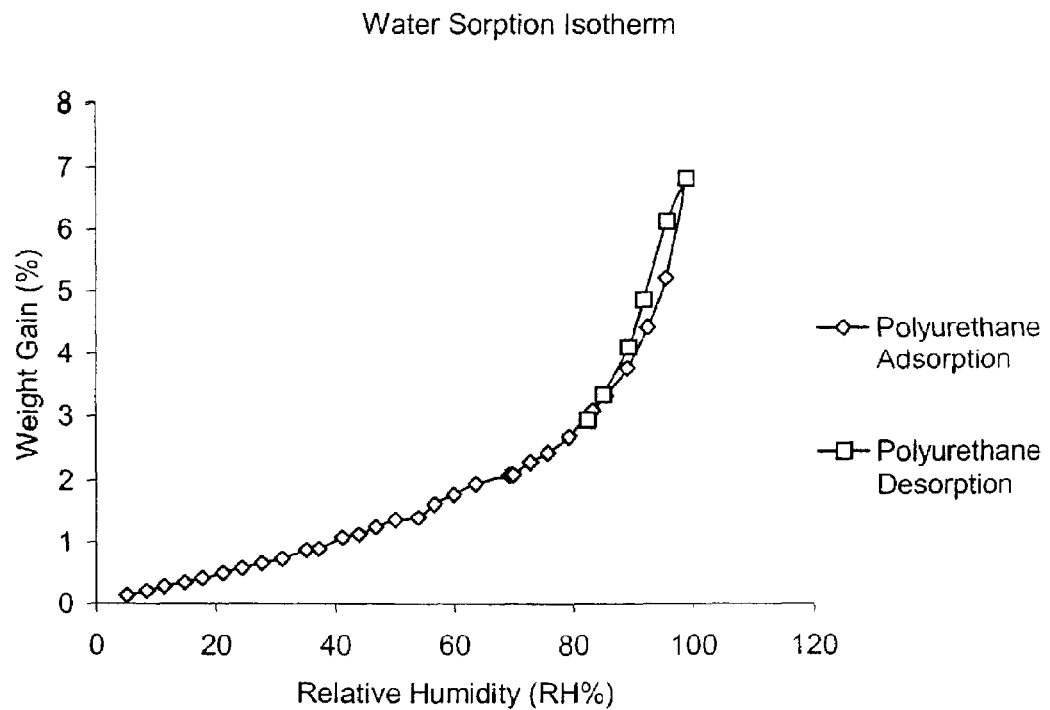
FIG. 30 is a water sorption isotherm of a polyurethane coating material.
Figure 31:
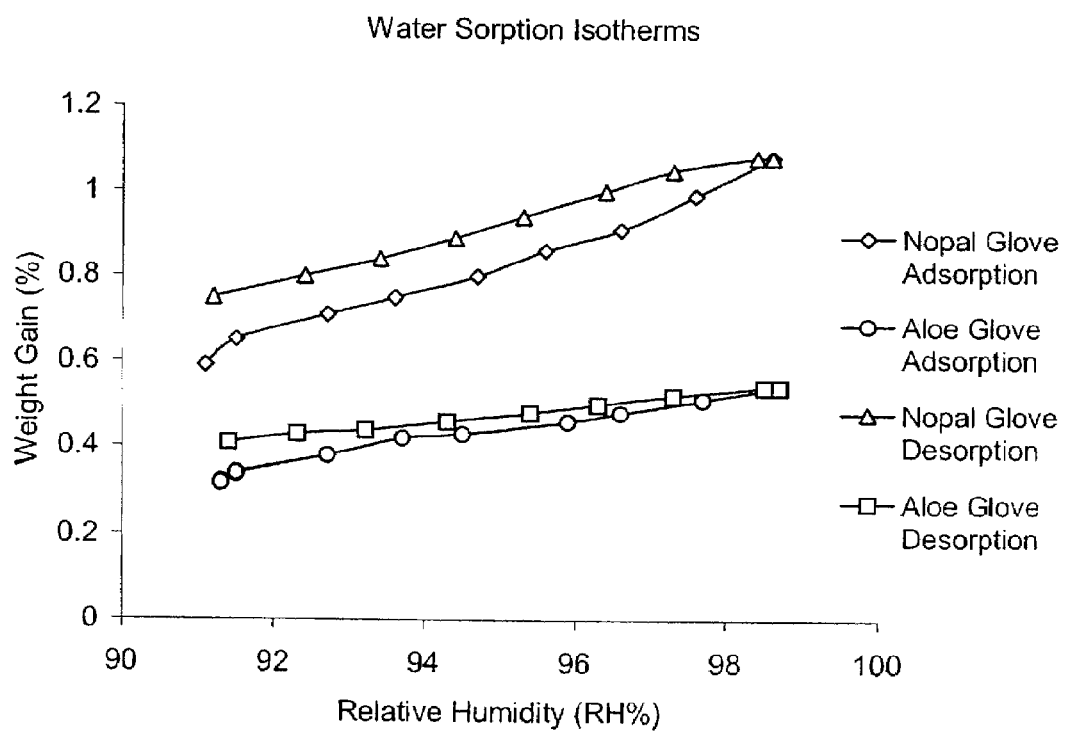
FIG. 31 is a comparison of water sorption isotherms of a vinyl glove coated with a Nopal extract and vitamin E and of a vinyl glove coated with an Aloe vera extract and Vitamin E.

For FIGS. 25-31, water sorption studies were conducted using a water vapor sorption analyzer, HYDROSORB 1000 made by Quantachrome Instruments, Boynton Beach, Fla., USA, using standard techniques for measuring adsorption and desorption isotherms. The isotherm data was collected at 35° C., which approximates human hand (body) temperature under a glove. Sorption isotherms were obtained for samples of Nopal (FIG. 26), Aloe vera (FIG. 27 adsorption only), cornstarch (FIG. 28), silicone powder (FIG. 29) and a polyurethane (FIG. 30) and for vinyl gloves treated with an interior surface coating of Nopal extract and Vitamin E and with Aloe vera extract and Vitamin E (FIG. 31). FIG. 25 is an overlay of the adsorption curves shown in FIGS. 26-30. The absorbate was water with a molecular weight of 18.01, an absorbate cross-section area of 12.5, and absorbate density of 0.997, a gas factor of 3.00E-05. The adsorption isotherms were plotted as % weight gain versus RH %. The Nopal absorbs approximately twice the moisture as the Aloe vera as shown in FIGS. 25 and 31 at maximal absorption, approximately 98%-99% RH.

Figure 28:
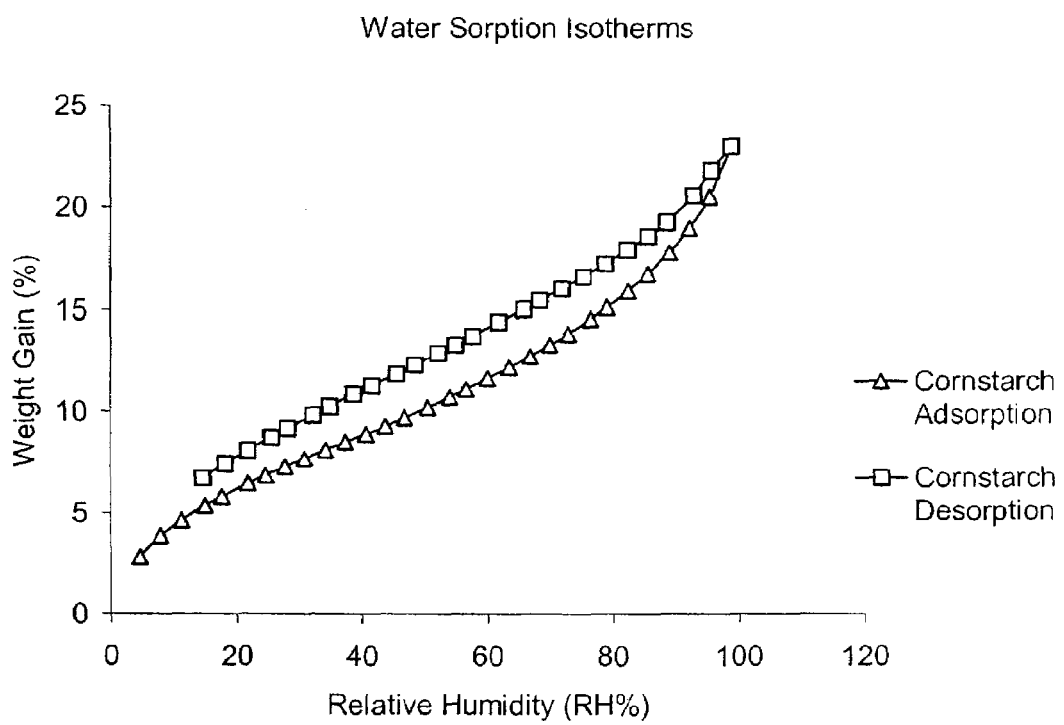
FIG. 28 is a water sorption isotherm of cornstarch.

Comparing the isotherms of the various coating used on gloves helps elucidate the distinct properties which the Nopal and Aloe vera contribute to the surface of a glove. Cornstarch, silicone and polyurethane are common glove interior surface coatings used as donning lubricants (supra). The cornstarch isotherm shown in FIG. 28 is significant because it maximally absorbs only 23% by weight of hand moisture (also adsorption isotherm shown in FIG. 25). A significantly larger quantity of cornstarch would need to be applied to a glove to absorb the same amount of sweat as using Nopal. The desorption isotherm shown in FIG. 28 also demonstrates hysteresis. Water is more easily absorbed than released very likely contributing to the negative perception of powder drying the hands out too much for some users. Should hands desiccate with a glove treated with Nopal or Aloe vera, the polysaccharides would easily release their water back to the epidermis of the skin, much as the polysaccharides function as a water reservoir within the plant. The cornstarch isotherm illustrates another problem that a significant proportion of water absorption occurs within the range of relative humidities encountered in normal storage. This increases the water content of a stored glove which is known to increase the problems with increasing bioburden over time and also causes a problem with the gloves "bricking" (the gloves stick together). The bioburden occurs in non-sterile gloves where during the manufacturing and packing process, the gloves may become contaminated with bacteria, fungi and viruses on the wear-contacting surface and on the outside surface. The cornstarch plus water provides nutrients for microbes, e.g., bacteria, fungi and viruses to multiply. The bioburden becomes a significant issue if the patient in contact with the glove is immuno-suppressed, where the microbes may produce serious health problems.

As shown in FIGS. 29 and 25, silicone maximally absorbed 16% by weight of water. Because silicone lubricant is very thin, it represents significantly less than 1% (one percent) by weight of the glove; the silicone is ineffective with water homeostasis beneath the glove. Thus, although silicone is used for donnability, it does not influence the perception of comfort caused by the water homeostasis after the glove is donned.

As shown in FIGS. 30 and 25, the commercially available polyurethane coating maximally absorbed about 45% by weight which is half of the maximum absorption of the Aloe vera extract and a quarter of the Nopal extract. Similar to silicone, polyurethane is used to improve donnability, but fails to improve the perception of comfort caused by the water homeostasis after the glove is donned.

To further explore and validate the measurable impact of water adsorption capacity, narrower sorption isotherms for gloves were measured at body temperature (35° C.) (approximating the hand moisture environment under a glove next to the wearer's skin) and at a RH range of 80% to approximately 99% RH. Sorption isotherms were measured for a vinyl (PVC) glove treated with an interior coating of the Nopal extract of the present invention and Vitamin E and for a commercially made vinyl glove (PVC) treated with an interior coating of a Aloe vera extract and Vitamin E. The sorption isotherms were measured on samples of glove fingers cut from gloves treated with the respective coating material. The isotherms were plotted as Weight Gain % versus Relative Humidity (RH %), as shown in FIG. 31. The glove treated with the Nopal and Vitamin E gained about twice the water weight maximally absorbed as the glove treated with Aloe vera and Vitamin E. The ability of the Nopal to contribute to water homeostasis between the hand and the glove as a glove coating contributes to user satisfaction and comfort.

Figure 26:
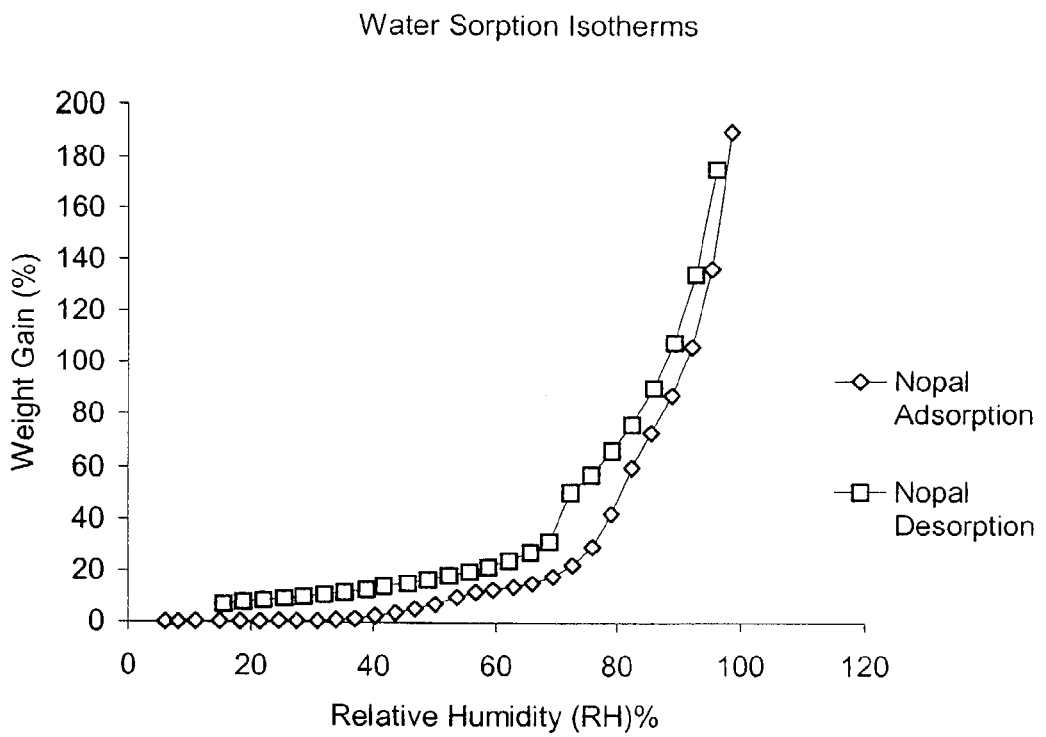
FIG. 26 is a water sorption isotherm of a Nopal extract.
Figure 27:
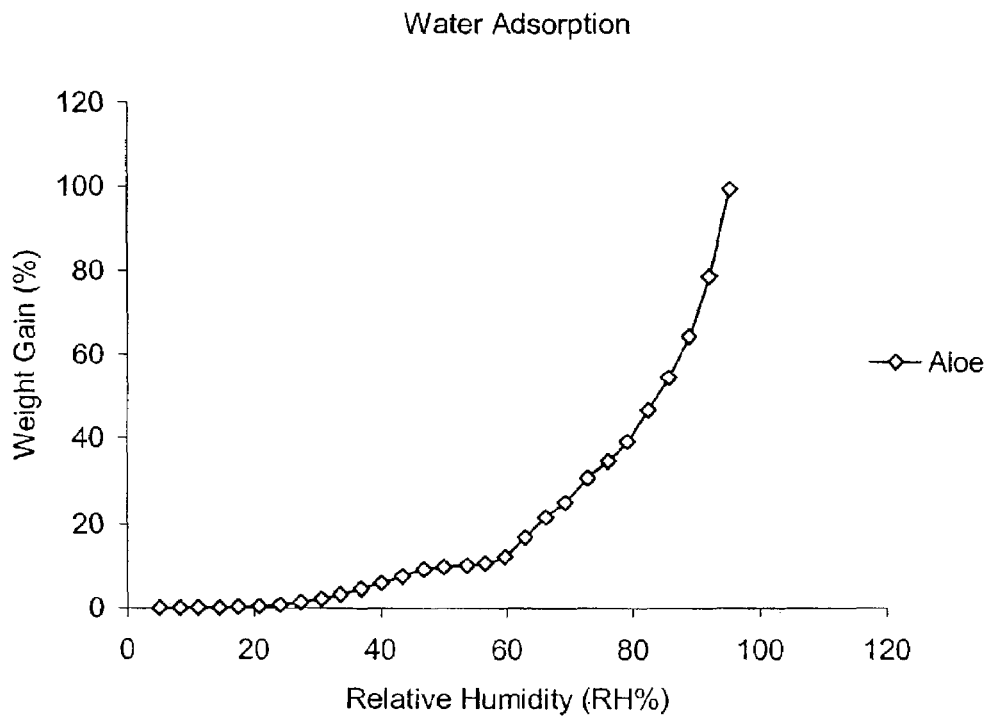
FIG. 27 is a water adsorption isotherm of an Aloe vera extract.

Furthermore, since the Nopal samples both in FIGS. 26 and 31 show little hysteresis in the isotherms; the ability to reversibly absorb perspiration without the abrasive properties of cornstarch is an advantage. If the same water homeostasis can be accomplished with half the quantity of an extract and still satisfy the customer (wearer), an economic advantage occurs.

From the data shown in FIGS. 26 and 31, the non-Aloe vera botanical extract includes polysaccharide sources with a water sorption isotherm at body temperature (about 35° C.) which exhibits at least 110% water weight gain at about 98% to 100% relative humidity. The hydrophyllic nature of the non-Aloe vera botanical extract is clearly demonstrated.

The uniform distribution of the polysaccharides provides for an optimal reservoir for water homeostasis beneath the glove keeping the skin appropriately moist during use. In addition, the uniform bioavailability of the active intrinsic compounds of the Nopal or added compounds (additives) is maximized.

The Nopal extract is used as a glove coating to replace cornstarch powder as a donning agent and/or as a releasing agent which prevents the finished articles from sticking to themselves or to the formers on which they are made. Advantageously, the stabilizing thixotropic properties of the polysaccharide biopolymer component of the Nopal extract allows for uniform application of a coating to the surface of the glove. The moisture regulating adsorption and desorption isotherms of the Nopal polysaccharide biopolymer coating advantageously optimize water homeostasis beneath the glove. Historically, Nopal has been used in folk medicine. More recently, experiments have been performed on various plant materials (for example see U.S. Patent Application No. 2002/0132021 to Raskin et al.). There is current information that the Nopal extract contains compounds with a range of therapeutically relevant physiologic activity including moisturizing, anti-microbial, wound healing, anti-inflammation, analgesia and anti-aging properties (see Ahmad, Antiviral Research 30 (1996) 75-85; Park et al., Filoterapia 72 (2001) 288-290; Loro et al., Journal of Ethnopharmacology 67 (1999) 213-218; Park et al., Filoterapia 72 (2001) 165-176; U.S. Pat. No. 6,447,820, to Niazi; Park et al., Archives of Pharmacal Research, Vol. 21, Issue 1, Feb. 1, 1998, pp. 30-34;

Budinsky et al., Prostaglandins, Leukotrienes and Essential Fatty Acids (2001), 65(1), 45-50; U.S. Pat. No. 6,099,866, to Slimak; U.S. Pat. No. 5,800,818 to Prugnaud et al.; and U.S. Patent Application Publication No. 2002/0102317, to Gutterrez et al., all of which are hereby incorporated herein by reference). In addition the Nopal extract is an optimal vehicle to fortify with vitamins and chemicals which enhance the protection of the skin of the user.

Most advantageously, data comparing the Aloe vera extract and the Nopal Extract found that no free sugar (reducing sugars or monosaccharides) exists in the Nopal extract whereas the Aloe vera extract contains several percent using a Benedict test. The extract samples were quantitatively tested for reducing sugar using Benedict solution using standard color reactions. The Aloe vera extract tested "strongly positive" for reducing sugars. The Nopal extract tested "negative" for reducing sugars. A more sensitive HPLC test was performed to measure free sugars in the Nopal extract and the Aloe vera extract. The results are shown in Table 1 below.

TABLE 1

HPLC of Sugars in Alcohol Soluble Fractions

| SAMPLE | SUGARS | 75% ethyl alcohol soluble % | % of original sample |
|---|---|---|---|
| Aloe vera extract | Sucrose | 11.54 | 1.00 |
|  | Glucose | 27.95 | 2.43 |
|  | Fructose | 14.26 | 1.24 |
| Nopal Extract | Sucrose | 7.94 | 0.24 |
|  | Glucose | 1.32 | 0.04 |
|  | Mannose | 1.62 | 0.05 |
|  | Fructose | 0.99 | 0.03 |

The Free sugar content for the Nopal extract is considerably smaller than that of the Aloe vera extract as shown in Column 4 of Table 1 supra. Existing strategies to minimize the bioburden with examination gloves include maintaining a low moisture content during transportation and storage and using biocides. These measures traditionally have been used to minimize microbial (fungi, bacterial and virus) growth. Substitution of non-Aloe vera botanical extract having non-detectable amounts of free sugars as measured by the Benedict solution test or lessened amounts as illustrated by the HPLC test supra for coating materials, preferably Nopal extract, has an unexpected benefit and advantage over Aloe vera as a coating material in providing minimization of bioburden by reducing the amounts of nutrients for microbial growth. Advantageously, this results in reducing costs in production when biocides are reduced or eliminated. Another advantageous result is an increase in shelf-life due to lessened microbial growth. Another important advantage is fewer infections in auto-immune suppressed persons due to the diminished exposure to bioburden in non-sterile articles.

A sugar analysis of the hydrolized polysaccharide chains yields the identical sugar subunits (rhamnose, arabinose, xylose, mannose, galactose, and glucose). The identical sugar subunits, as well as, the isotherm properties and free sugar properties of Nopal extract over Aloe vera extract are surprising and unexpected results providing the advantages for non-Aloe vera coating materials discussed supra.

The aforementioned botanical extracts, the aforementioned non-Aloe vera botanical extracts, including the glucomannan, the galactomannan, and the aforementioned additives are commercially available. For example, for both types of aforementioned extracts or for materials for making both types of the aforementioned extracts see NHK Laboratories; Aloe Laboratories Harlingen, Tex., U.S.A.; Voigt Global Distribution; Natunola Health, Nepean, Ontario Canada; P. L. Thomas; Xiamen Xing Da Chemicals; Konjac Foods USA, Cupertino, Calif., U.S.A.; Pangaea Sciences; purified galactomannan (Fenu-Pure from NatuR&D, the Nutraceuticals Division of Adumim Food Ingredients, Industrial Zone, Mishor Adumim, Israel. The laboratory produced polysaccharides and the non-Aloe-vera laboratory produced polysaccharides, of the present invention are manufactured by known in the art techniques, such as, but not limited to, refining, extraction, plant gene insertion into bacteria or other biotechnology processes, etc.

Figure 11:
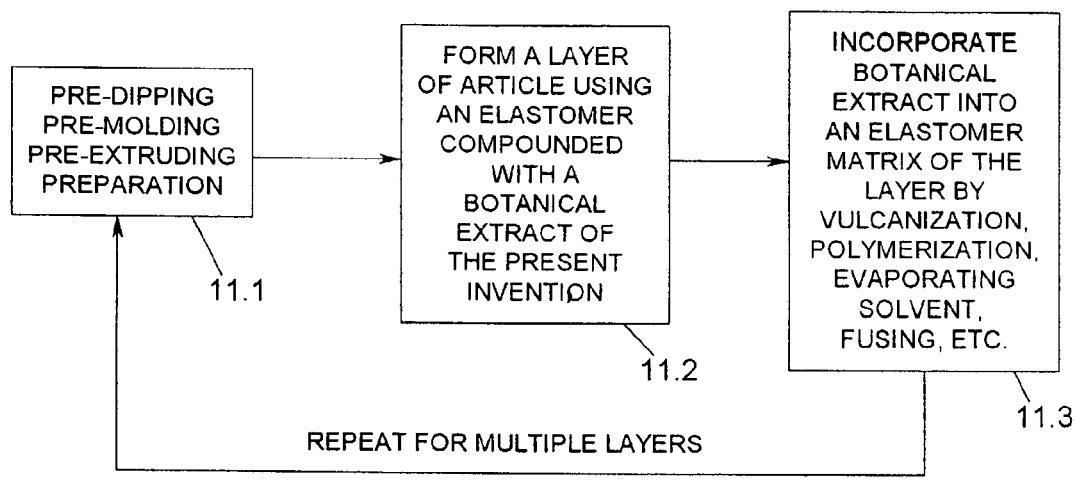
FIG. 11 is a schematic flow diagram showing a process for making a flexible elastomer article of the present invention.
Figure 12:
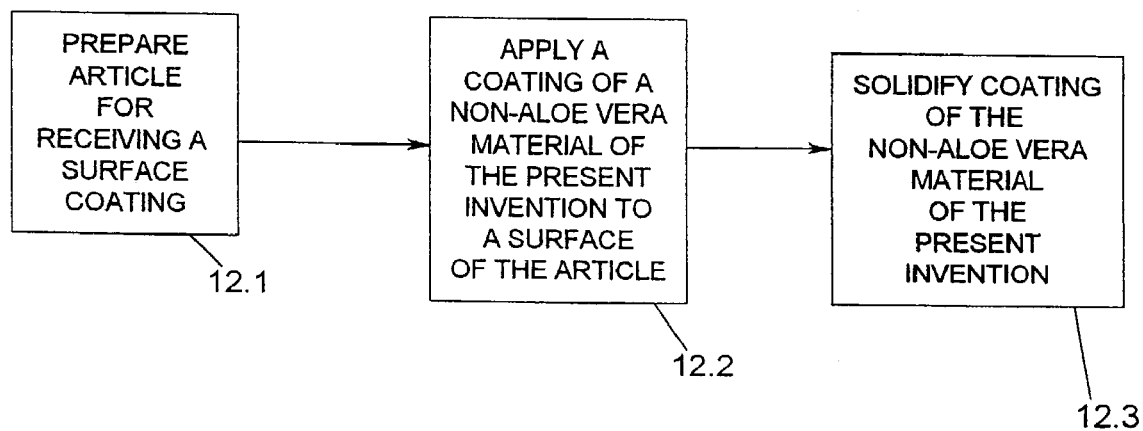
FIG. 12 is a schematic flow diagram showing a process for coating a flexible elastomer article with a non-Aloe vera coating material of the present invention.

Another aspect, a third aspect of the invention includes a botanical extract incorporated in an elastomer layer forming the flexible article and a non-Aloe vera coating material being coated preferably on at least the wearer contacting surface of the flexible article. The elastomer(s) used for the flexible article are any of the aforementioned elastomer(s); the botanical extract for incorporation into an elastomer layer forming the flexible article and the non-Aloe vera coating material used on the wearer contacting surface of the flexible article are those previously discussed supra. FIGS. 8-10 and 23 illustrate this aspect with respect to a glove. However, as one of ordinary skill in the art will appreciate, the present invention comprehends making single, bilaminar, and multi-layered flexible articles with a botanical extract incorporated into at least one layer and providing a surface non-Aloe vera coating material on preferably at least the wearer contacting surface; this is shown by the combination of FIGS. 11 and 12. The elastomers, the botanical extracts(s) and the non-Aloe vera coating materials selected for the single, bilaminar and multi-layer elastomer gloves disclosed supra and below may also preferably be used to make the single layer, bilaminar and multi-layer flexible elastomer articles of the present invention.

Referring now to the FIGS. 1-10 and 13-23 in which a glove and glove making procedure is illustrated. FIGS. 11 and 12 illustrate a process for making other flexible articles according to the present invention. The elastomer(s) disclosed for the glove may be used for the other types of flexible articles supra, as well as for the glove. The FIGs. are not drawn to scale. The shadings for the specific elastomer(s) have been omitted for simplicity in understanding the invention. It is to be understood that elastomer material(s) are used in the flexible elastomer articles of the present invention.

Referring first to FIG. 1, a medical or dental examination, procedure, disposable and/or surgical glove 100 is illustrated as having an outside surface (distal surface or outer distal surface or outermost surface) (OS) 102 and an inside or wearer contacting surface (WCS) 104. The raw material from which the glove is made includes an elastomer such as an NRL, a synthetic polyisoprene, a chloroprene, a PU, an acrylonitrile, a butadiene methylmethacrylate, an SBS, an SIS, an SEBS, a silicone, an acrylate-based hydrogel, any other elastomer that can be suspended into an emulsion, and any mixtures of any of the aforementioned elastomers. Alternatively, the raw material includes an elastomer such as an SBS, an SIS, an SEBS a silicone, a PU, a PVC, an acrylate-based hydrogel, any other elastomer that is suspendable, soluble or miscible in a solution or plastisol, and mixtures thereof, wherein the botanical extract is suspendable, soluble or miscible in the solution or plastisol, and mixtures of the aforementioned elastomers.

FIGS. 2-10 and 22 and 23 are cross sectional views of gloves which have an exterior appearance similar to glove 100 and have an OS 102 and a WCS 104. In FIGS. 2, 3, 4, 22, 8, 9, 10, 23 the quantity of botanical extract incorporated into a layer (or layers) of the elastomer (or elastomers) is approximately 0.2 to 2.5 phr (0.2 to 2.5 parts of botanical extract per 100 parts of elastomer in the dry weight of the finished article). The quantity of botanical extract is calculated as described supra and a solution (preferably water) of the botanical extract is compounded with the elastomer(s) raw material in a quantity sufficient to achieve the specified phr for the finished article.

FIGS. 2-4 and 22 illustrate a first aspect of the present invention wherein a glove has a botanical extract incorporated into the elastomer matrix of the article. The preferred elastomer, botanical extract and phr range selected for the single layer glove are also preferably used for other single layer flexible elastomer articles of the present invention.

Figure 2:
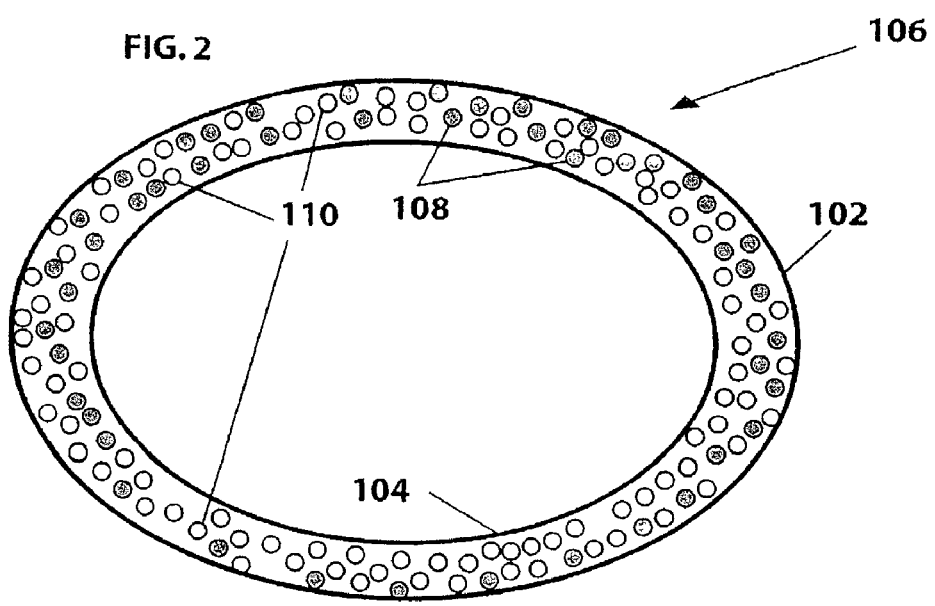
FIG. 2 is a cross sectional view of a portion of a single layer glove in which the material that the glove is made from includes at least one botanical extract.

The elastomer selected for a single layer glove and botanical extract for incorporation into the elastomer are as disclosed supra for a single layer glove. Referring next to FIG. 2, a preferred embodiment single layer glove 106 is made from preferably an elastomer emulsion, solution or a plastisol compounded with Aloe vera extract 108 and/or Nopal extract 110. The elastomer compounded with the botanical extract 108, 110 is then vulcanized, polymerized, cured, evaporated and/or fused so as to incorporate the botanical extract 108, 110 into the elastomer matrix. Preferably the elastomer(s) is prepared in the elastomer emulsion and includes an elastomer selected from a NRL, a synthetic polyisoprene, a chloroprene, a PU, an acrylonitrile, a butadiene methylmethacrylate, an SBS, an SIS, an SEBS, a silicone, an acrylate-based hydrogel, any other elastomer that can be suspended into an emulsion, or a mixture of one or more of the aforementioned elastomers. Preferably, where a solution or a plastisol of an elastomer is prepared, the elastomer includes an elastomer selected from a silicone, a PU, an acrylate-based hydrogel, an SEBS, an SIS, an SBS, a PVC, any other elastomer wherein the botanical extract is suspendable, soluble, or miscible, or a mixture of one or more of the said elastomers. The elastomer(s) used are also as described above in the general discussion. The elastomer emulsion, solution or the plastisol used for the subsequent dipping is compounded, with, apart from the usual ingredients, most preferably an Aloe vera solution such that preferably approximately 0.2 to 2.5 phr are in the dry finished glove. The concentration may be governed by applicable standards. The minimum concentration for the International Aloe Science Council certification is 15% by weight (www.iasc.org).

Figure 3:
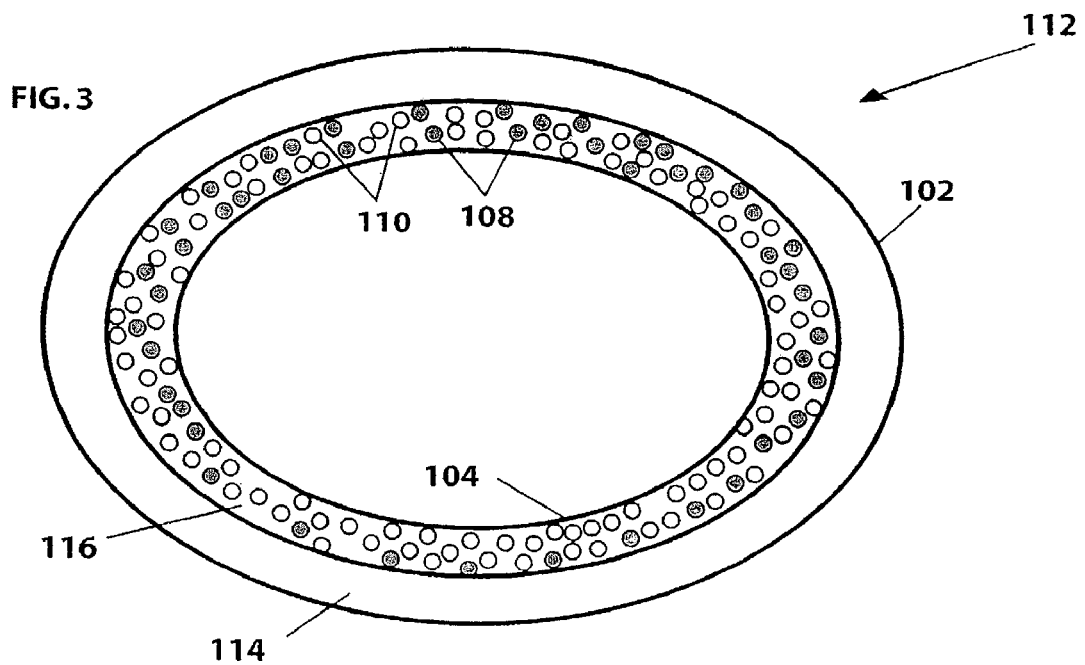
FIG. 3 is a cross sectional view of a portion of a bilaminar glove in which the material that the interior layer of the glove is made from includes at least one botanical extract.

The elastomer(s) selected for the bilaminar glove and the botanical extract for incorporation into at least one layer of the glove are as disclosed supra for a bilaminar glove. The preferred elastomer(s), botanical extract(s) and phr selected for the bilaminar glove may also be used for making a preferred bilaminar flexible elastomer article of the present invention. Referring now to FIG. 3, a preferred embodiment of a bilaminar glove 112 having a first layer 114 and a second layer 116. The elastomer selected for the first layer 114 and for the second layer 116 may be selected from the group of elastomers including preferably an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer that is suspendable, soluble or miscible into an emulsion, solution or plastisol, and mixtures thereof. The botanical extract is suspendable, soluble and/or miscible in the emulsion, solution or plastisol of the elastomer(s) for the layer of the glove into which the botanical extract is incorporated. First layer 114 has an OS 102. Second layer 116 forms an interior layer of glove 112, having a WCS 104. Preferably Aloe vera extract 108 and/or Nopal extract 110 are the botanical extracts compounded with the elastomer(s) forming the second layer 116. Aloe vera extract and/or Nopal extract is preferably used with a concentration of approximately 0.2 to 2.5 phr in the finished glove. Most preferably Aloe vera extract is used with a concentration of approximately 0.2 to 2.5 phr in the finished glove.

The elastomers disclosed for the multi-layered gloves and the botanical extract for incorporation into at least one layer of the glove are as disclosed supra for a multi-layer glove. The elastomer(s), botanical extract(s) and phr selected for the multi-layered glove may also be used for making a preferable multi-layered flexible article of the present invention.

Figure 4:
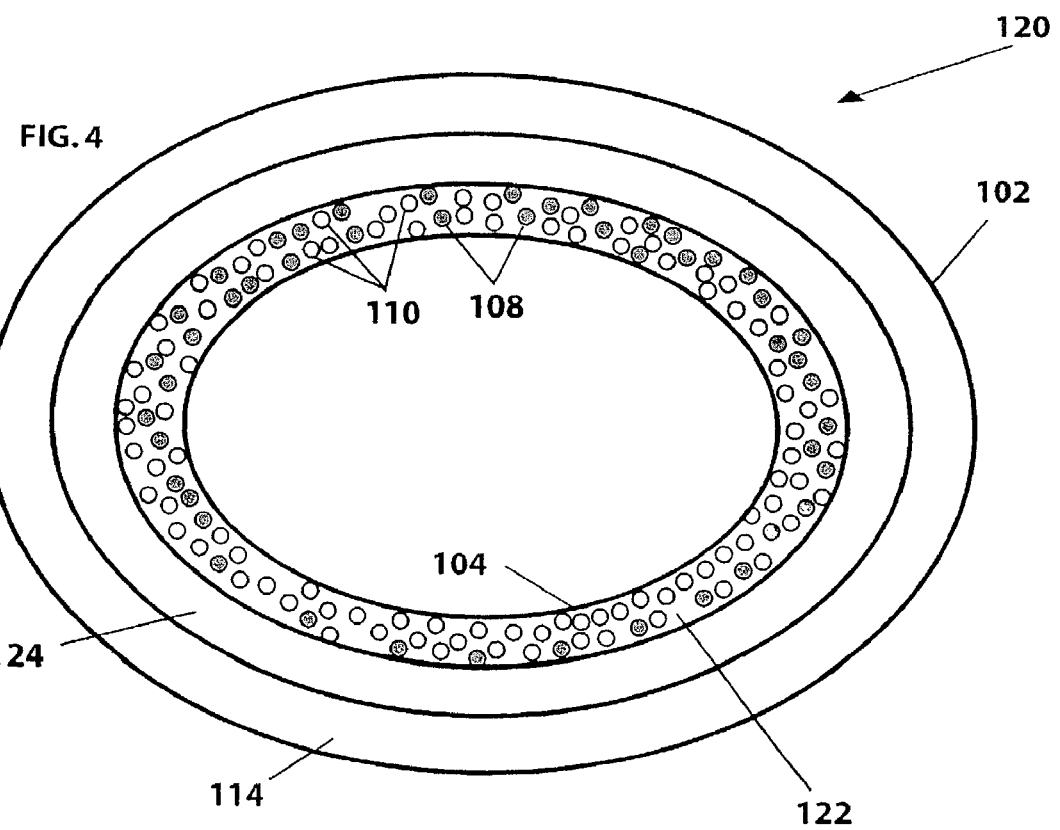
FIG. 4 is a cross sectional view of a portion of a multi-layer glove in which the material that the innermost layer of the glove is made from includes at least one botanical extract.

FIG. 4 illustrates the botanical extract(s) incorporated into the innermost layer and FIG. 22 illustrates the botanical extract(s) incorporated into a non-innermost layer of the multi-layer glove. Referring next to FIG. 4, a preferred embodiment of a multi-layer glove 120 has a first layer 114; an innermost layer 122 and a second (or more layer) 124 disposed between the first layer 114 and innermost layer 122. The elastomer(s) for each layer of the glove 114, 112, 124 may be selected from the group of elastomers including preferably an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer that is suspendable, soluble or miscible into an emulsion, solution or plastisol, and mixtures thereof. The botanical extract is suspendable, soluble and/or miscible in the emulsion, solution or plastisol of the elastomer(s) for the layer of the glove into which the botanical extract is incorporated. The botanical extracts, Aloe vera extract 108 and/or Nopal extract 110 are preferably at least compounded with the elastomer(s) of the innermost layer 122 and may be compounded with elastomer(s) of the second or more layers 124. The selected elastomer(s) used are preferably compounded with a Nopal extract and/or Aloe vera extract with a concentration of approximately 0.2 to 2.5 phr in the finished glove. Most preferably an Aloe vera extract is used, with a concentration of approximately 0.2 to 2.5 phr in the finished glove.

Referring now to FIG. 22, glove 121 an alternate embodiment of the multi-layer glove 120 of FIG. 4 is shown. Glove 121 has a first layer 114; an innermost layer 122, and a second (or more layer) 124 disposed between the first layer and the innermost layer 122. The first layer 114, the innermost layer 122 and the second/or more layer 124 are made of elastomer(s) preferably as disclosed for multi-layer glove 120 supra. Preferably the botanical extract(s), Aloe vera extract 108 and/or Nopal extract 110 are compounded with the elastomer(s) of second (or more) layer 124. The elastomer(s) are preferably compounded with Nopal extract and/or Aloe vera extract in a concentration between approximately 0.2 to 2.5 phr (botanical extract to elastomer) in the finished glove. Most preferably an Aloe vera extract is used with a concentration of approximately 0.2 to 2.5 phr in the finished glove.

The second aspect of the present invention includes applying a non-Aloe vera coating material (hereinalso "coating material") to at least a wearer contacting surface of a flexible article. The non-Aloe vera coating material contains a non-Aloe vera botanical extract having a mucinous polysaccharide. The non-Aloe vera botanical extract has moisture homeostasis capabilities, thixotropic properties of a liquid biopolymer, and serves as a lubricant, donning agent, providing moisturizing properties and contains therapeutic components that impart one or more of wound healing, anti-inflammatory, anti-microbial, analgesic, and anti-aging properties. The non-Aloe vera coating material may be selected from the group of non-Aloe vera botanical extracts including preferably non-Aloe vera botanical extracts of Nopal, okra, kelp, tamarind, psyllium, carrageenan, chia, flax, carob, guar, xanthan, konjac, cassia, tara, karaya, ghatti, tragacanth, glucomannan, galactomannan, non-Aloe vera laboratory produced polysaccharides, and mixtures thereof. Additional non-Aloe vera additives may be included in the non-Aloe vera coating material; these additives include Vitamin E, Vitamin A, Vitamin C, Vitamin $B_3$, Vitamin $B_5$, jojoba, rose hips, tea tree oil, flax seed oil, palm oil, acetylsalicylic acid, and mixtures thereof. The aforementioned non-Aloe vera botanical extracts and additives are commercially available or prepared by known in the art techniques, as discussed supra. Preferably the coating material contains a Nopal extract. Most preferably the coating material contains both Nopal and Vitamin E. The non-Aloe vera coating material is applied to the flexible article using conventional spray, dipping, tumbling, or soaking processes. Typically a 5% to 20% solution (water and/or ethanol) of the non-Aloe vera botanical extract is applied, but may range from 1% to 50% solution (based on a 100:1 powder of non-Aloe vera botanical extract).

The percentage range of coating materials selected is sufficient to accommodate existing flexible article formulas and machine configurations. For example, when using an oven to dry coating materials, a longer existing oven time would favor a more dilute concentration of the non-Aloe vera botanical extract in the coating material because of the additional time to evaporate the excess water.

Figure 5:
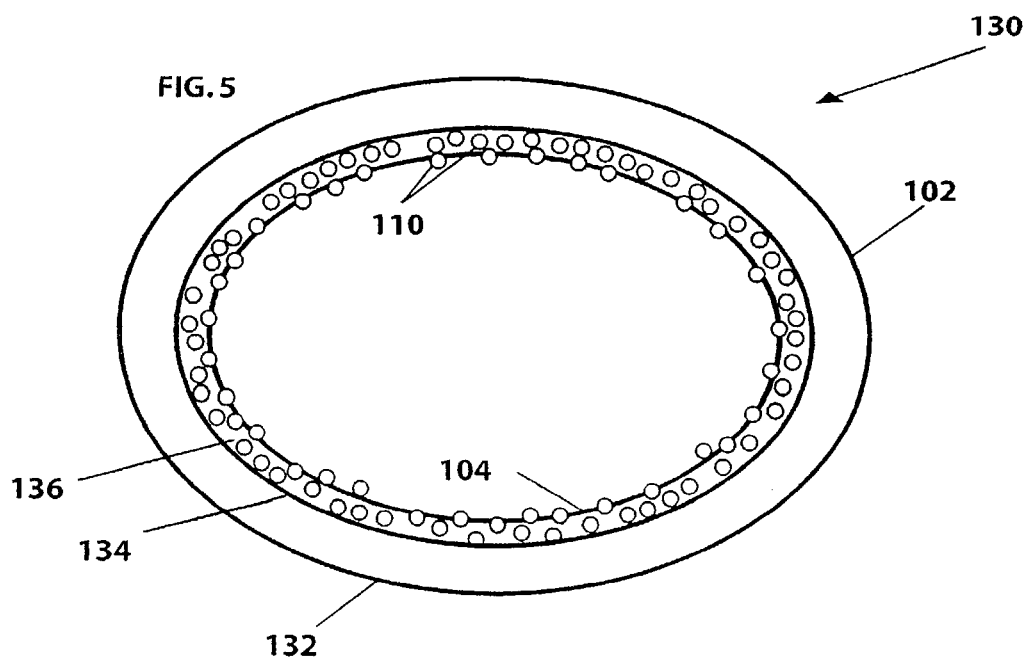
FIG. 5 is a cross sectional view of a portion of a single layer glove with an interior surface coating.
Figure 6:
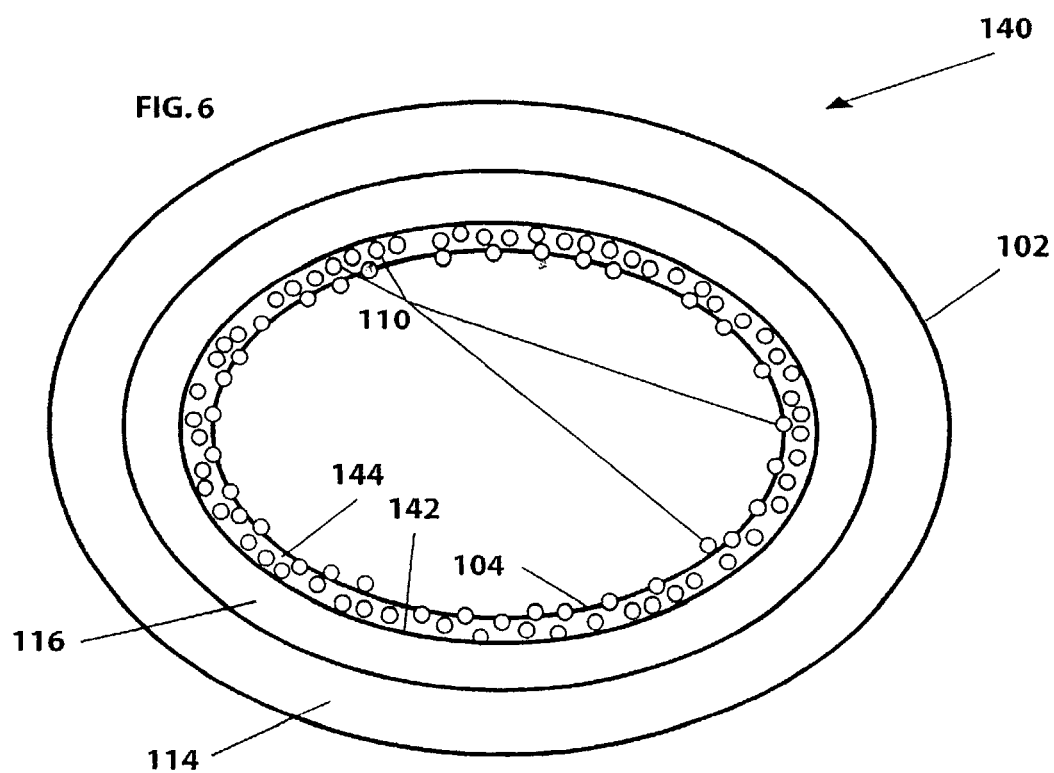
FIG. 6 is a cross sectional view of a portion of a bilaminar glove with an interior surface coating.
Figure 7:
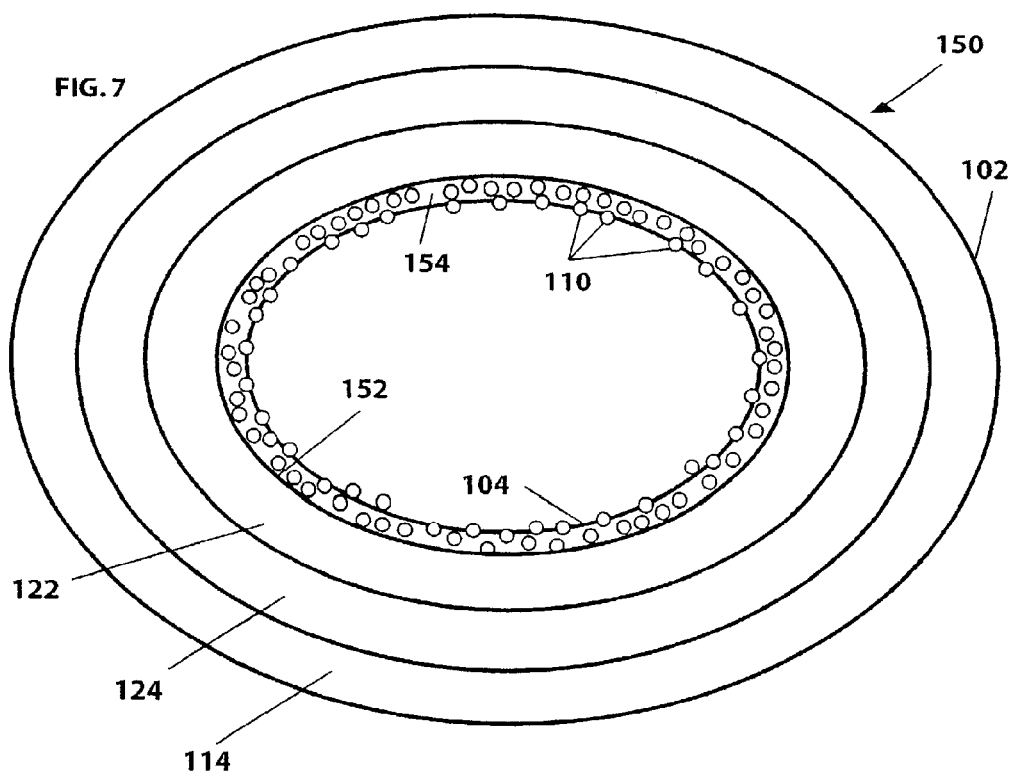
FIG. 7 is a cross sectional view of a portion of a multi-layer glove with an interior surface coating.

The following FIGS. 5-7 illustrate the surface coating is applied to single, bilaminar, and multi-layered gloves. The non-Aloe vera coating material of the present invention may also be applied to a single layer or a multi-layer or a bilaminar flexible article as included in the present invention. FIGS. 5-7 illustrate an aspect of the invention wherein the non-Aloe vera coating material is coated on the interior surface of the glove, e.g. the wearer contacting surface of the glove. Preferably a 5%-20% solution of the non-Aloe vera botanical extract is used in FIGS. 5-7. The solution is dried after application.

Referring now to FIG. 5, a single layer glove 130 having a preferred interior surface non-Aloe vera botanical coating of Nopal extract 110 is illustrated. Glove 130 has a single layer 132, made from an elastomer(s) selected from the group of elastomers including preferably an NRL, a synthetic polyisoprene, a chloroprene, a PU, a PVC, an SBS, an SIS, a silicone, a butadiene methylmethacrylate, an acrylonitrile, an SEBS, an acrylate-based hydrogel, any other elastomer that is suspendable, soluble or miscible into an emulsion, solution or plastisol, and mixtures thereof. Any other elastomer material or combination of elastomer materials suitable for forming a single layer glove may be used to make single layer glove 130. Single layer 132 has an outer surface OS 102 and an opposite coating surface 134, (e.g., the wearer contacting surface of an uncoated glove). A surface coating of Nopal extract 110 is preferably applied to coating surface 134 forming coating layer 136. Thus, a wearer contacting surface (WCS) 104 is coated with Nopal extract 110. The application of the coating is done using a spray, dipping, tumble or soaking process.

Referring next to FIG. 6, a bilaminar glove 140 having a preferred interior surface non-Aloe vera coating of Nopal extract 110 is illustrated. Bilaminar glove 140 has a first layer 114 and a second layer 116. The elastomer (or elastomers) selected for the first layer 114 and the second layer 116 are preferably an elastomer selected from the group of elastomers, including an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer that is suspendable, soluble or miscible into an emulsion, solution or plastisol, and mixtures thereof. Any other elastomer material or combination of elastomer materials suitable for forming a bilaminar glove may be used to make bilaminar glove 140. First layer 114 has an OS 102. Second layer 116 forms an interior layer of glove 112, having a WCS 104. First layer 114 has an OS 102. The second layer 116 has an interior coating surface 142 (e.g., the wearer contacting surface of an uncoated glove). Preferably a surface coating of Nopal extract 110 is applied to the coating surface 142 forming a coating layer 144. The non-Aloe vera coating is preferably applied onto the inner surface of the gloves by spraying, dipping, tumbling or soaking. Thus, a wearer contacting surface (WCS) 104 is coated with coating layer of Nopal extract 110.

Referring now to FIG. 7, a multi-layer glove 150, preferably having an interior surface non-Aloe vera coating of Nopal extract 110, is illustrated. Glove 150 is similar to glove 120 in FIG. 4 having a first layer 114, and an innermost layer 122 and a second (or more) layer 124. The innermost layer 122 is disposed toward an interior of the glove 150. First layer 114 has OS 102. Innermost layer 122 has a surface 152 for receiving a coating. Preferably a non-Aloe vera coating of Nopal extract 110 is applied to surface 152 by using a spray, dipping, tumble process, or soaking. Thus, the coating forms a coating layer 154 forming a wearer contacting surface 104 of glove 150. Preferably the elastomer(s) for each layer (114, 122, 124) of the glove includes one or more of an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer that is suspendable, soluble or miscible into an emulsion, solution or plastisol, and mixtures thereof. Any other elastomer material or combination of elastomer materials suitable for forming a multi-layer glove may be used to make multi-layer glove 150.

A third aspect of the invention includes a botanical extract incorporated in an elastomer layer forming the flexible article and a non-Aloe vera coating material being coated preferably on at least the wearer contacting surface of the flexible article. The elastomer(s) used for the flexible article are any of the aforementioned elastomer(s) discussed with reference to FIGS. 2-4; the botanical extract for incorporation into an elastomer layer forming the flexible article and the non-Aloe vera coating material used on the wearer contacting surface of the flexible article are those previously discussed supra. FIGS. 8-10 and 23 illustrate this with respect to a glove. However, as one of ordinary skill in the art will appreciate, the present invention comprehends making single, bilaminar, and multi-layered flexible articles with a botanical extract incorporated into at least one layer and providing a surface non-Aloe vera coating material on preferably at least the wearer contacting surface; this is shown by the combination of FIGS. 11 and 12. The elastomer(s) compounded with botanical extract(s), the botanical extracts(s) and the non-Aloe vera coating materials selected for the single, bilaminar and multi-layer elastomeric gloves disclosed supra and below may also preferably be used to make the single layer, bilaminar and multi-layer flexible articles of the present invention.

Figure 8:
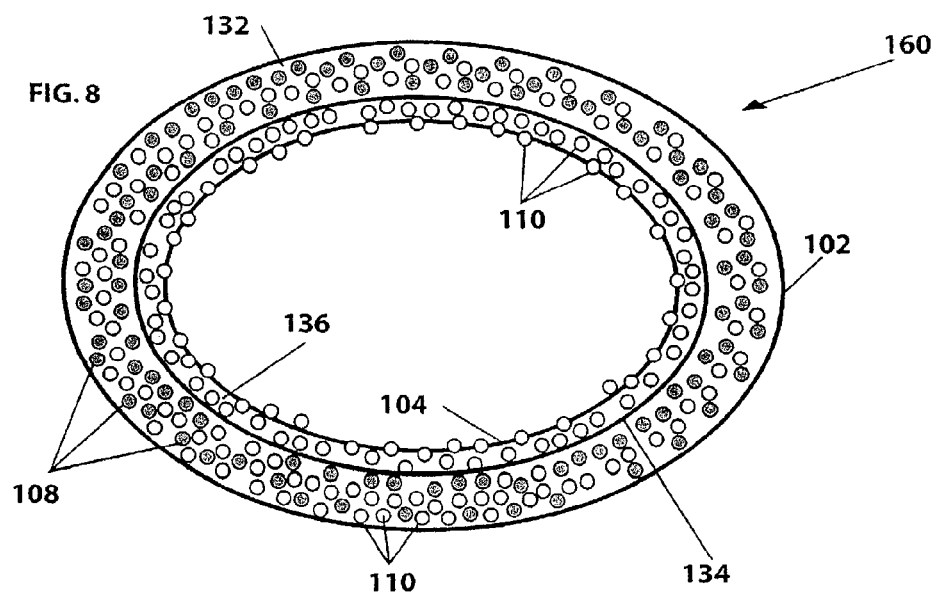
FIG. 8 is a cross sectional view of a portion of a single layer glove with an interior surface coating and in which the material that the glove is made from includes at least one botanical extract.

Referring next to FIG. 8, a single layer glove 160 preferably has a botanical extract both within the glove layer and a non-Aloe vera coating material as an interior coating. The structure of glove 160 is similar to that in association with FIG. 5, wherein like numbers refer to similar parts. Glove 160 has a single layer 132 having an OS 102 and an opposite coating layer surface 134 for depositing a surface coating layer 136 thereon. Layer 132 is made from an elastomer compounded with a botanical extract of the present invention. Preferably the elastomer may be selected from the group of elastomers including preferably an NRL, a synthetic polyisoprene, a chloroprene, a PU, an acrylonitrile, a butadiene methylmethacrylate, an SBS, an SIS, an SEBS, a silicone, and an acrylate-based hydrogel, any other elastomer that can be suspended into an emulsion, and mixtures thereof. Any other elastomer material or combination of elastomer materials suitable for forming a single layer glove and into which the botanical extract is suspendable, soluble or miscible may be used to make single layer glove 160. Preferably the botanical extract selected for compounding with the elastomer is Aloe vera extract 108 and/or Nopal extract 110, (most preferably Aloe vera extract 108 is used) in the preferred phr amounts described in association with FIG. 2. The coating layer surface 134 is coated with a non-Aloe vera coating material, most preferably a Nopal extract (preferably 5% to 20% solution) using a spray, dipping, tumble, or soaking process forming coating layer 136.

Referring now to FIG. 9, a bilaminar glove 170 is constructed similar to glove 140 in FIG. 6 where like numbers refer to similar parts. A first layer 114 and a second layer 116 are preferably made from one or more elastomers. The elastomer or elastomers for each layer 114, 116 may be selected from the group of elastomers including preferably an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer that is suspendable, soluble or miscible into an emulsion, solution or plastisol, and mixtures thereof. Any other elastomer material or combination of elastomer materials suitable for forming a bilaminar glove may be used to make a layer of glove 170 that does not contain the botanical extract. Any other elastomer material or combination of elastomer materials suitable for forming a bilaminar glove and into which the botanical extract is suspendable, soluble or miscible may be used to make the layer or layers of glove 170 into which the botanical extract is incorporated. A botanical extract of the present invention is compounded with the elastomer(s) selected for the layer(s) of the glove into which the botanical extract is to be incorporated. The botanical extract is suspendable, soluble or miscible in the emulsion, solution or plastisol of the elastomer for the selected layer 114, 116 of the glove into which the botanical extract is to be incorporated. The botanical extract is preferably an Aloe vera extract or a Nopal extract or both. Preferably Aloe vera extract 108 and/or Nopal extract 110 (and most preferably Aloe vera extract 108 is used) are added to the second layer 116. The preferred amounts (phr) of botanical extract is as disclosed in association with FIG. 3. First layer 114 has OS 102. Second layer 116 has a coating layer surface 142. The coating layer surface 142 is coated with a non-Aloe vera coating material, preferably a Nopal extract 110 (preferably in a 5% to 20% solution) using a spray, dipping, tumble, or soaking process forming coating layer 144 which provides a wearer contacting surface 104.

FIGS. 10 and 23 illustrate a multi-layer glove having a botanical extract within at least one layer and having a non-Aloe-vera coating material on the wearer contacting surface. Referring next to FIG. 10, a multi-layer glove 180 similar to glove 150 in FIG. 7 where like numbers refer to similar parts, is illustrated. A multi-layer glove has a first layer 114, an innermost layer 122 and a second (or more) layer 124, therebetween. Innermost layer 122 is disposed toward an interior of the glove 180. The elastomer(s) selected for each layer of the glove may be selected from the group of elastomers including preferably an NRL, a synthetic polyisoprene, a chloroprene, a PU, an acrylonitrile, a butadiene methylmethacrylate, an SBS, an SIS, an SEBS, a silicone, an acrylate-based hydrogel, a PVC, any other elastomer that is suspendable, soluble or Xmiscible into an emulsion, solution or plastisol, and mixtures thereof. Any other elastomer material or combination of elastomer materials suitable for forming a multi-layer glove may be used to make a layer or layers of glove 180 that do not contain the botanical extract. Any other elastomer material or combination of elastomer materials suitable for forming a multi-layer glove and into which the botanical extract is suspendable, soluble or miscible may be used to make the layer or layers of glove 180 into which the botanical extract is incorporated. A botanical extract of the present invention is compounded with the elastomer(s) selected for the layer(s) of the glove into which the botanical extract is to be incorporated. The botanical extract is suspendable, soluble or miscible in the emulsion, solution or plastisol of the elastomer selected for the layer(s) of the glove into which the botanical extract is to be incorporated. Preferably Aloe vera extract 108 and/or Nopal extract 110 (and most preferably Aloe vera extract 108) are preferably compounded with the elastomer(s) forming the innermost layer 122 and optionally the second (or more) layers 124 in the preferred amounts (phr's) disclosed in association with FIGS. 4 and 22. Innermost layer 122 has a coating contacting surface 152. The coating contacting surface 152 is coated with a coating layer 154 of a non-Aloe vera coating material, preferably Nopal extract 110 (preferably in a 5% to 20% solution) using a spray, dipping, tumble, or soaking process.

Referring now to FIG. 23, a multi-layer glove 181 is disclosed. Glove 181 is similar to glove 180 having first layer 114, innermost layer 122 and a second (or more) layer 124 with innermost layer 122 disposed toward an interior of glove 151. First layer 114 has OS 102. Innermost layer 122 has a surface 152 for receiving a coating. Preferably a non-Aloe vera coating material of Nopal extract 110 (preferably in a 5% to 20% solution) is applied to surface 152 by using a spray, dipping or tumble process. The coating forms a coating layer 154 forming a wearer contacting surface 104 of glove 181. The elastomer(s) used in each layer of the multi-layer glove includes the elastomer(s) previously listed with respect to glove 180. A botanical extract of the present invention is compounded with the elastomer(s) selected for the layer(s) of the glove into which the botanical extract is to be incorporated. Preferably Aloe vera extract 108 and/or Nopal extract 110 (most preferably Aloe vera extract 108 is used) are added to at least one layer, in this instance the second layer 124. The concentration of botanical extract to elastomer (phr) in the finished glove 181 is preferably as described in association with FIGS. 4 and 22.

The quantity of the botanical extract to incorporate into the elastomer matrix of the glove shown in FIGS. 2-4, 8-10, and 22-23 is sufficient to confer: a lower modulus of the glove similar to NRL without removal of laticifer cell content, antioxidant protection of the glove, colloidal stabilization of the elastomer emulsion of the matrix material of the glove, emulsification enhancement and thixotropic properties providing uniformity of the glove thickness. The botanical extract(s) are commercially available or can be manufactured by known in the art processes (supra).

In summary, for FIGS. 2-4, 8-10 and 22-23, the elastomer(s) (which are suspended in an emulsion or, suspendable, soluble or miscible in the solution or the plastisol) are compounded with a botanical extract, preferably an Aloe vera extract and a Nopal extract, most preferably an Aloe vera extract, in a quantity sufficient to have between approximately 0.2 to 2.5 phr of the botanical extract to elastomer in the finished glove, (or other flexible elastomer article) to produce a target finished product ratio of between approximately 0.2 to 5.0 phr. The concentration of botanical extract to parts per hundred of elastomer may range from approximately 0.2 to 2.5 phr or higher in the finished glove (or other finished flexible elastomer article). The quantity of botanical extract selected is sufficient to ensure that physical properties required by ASTM and/or ISO specifications supra (or other flexible article performance standards) are not exceeded for tensile strength, modulus, ultimate elongation and aging properties.

In summary, as illustrated in FIGS. 5-7, 8-10 and 23, and for other flexible elastomer articles, for the non-Aloe vera botanical coating (surface coating mixture), the concentration range of the non-Aloe vera botanical extract used is a 5% to 20% solution (water and/or ethanol), but may be prepared in a 1% to 50% solution. More preferably an 8% to 12% solution of non-Aloe vera botanical extract is used; most preferably a 10% solution is used. Alternatively, for the non-Aloe vera coating material, the non-Aloe vera botanical extract may also be expressed in units of phr of the non-Aloe vera botanical extract per hundred weight of elastomer in the finished product. The phr for the coating material may be determined by industry standards or guidelines for a particular non-Aloe vera botanical extract in the finished flexible elastomer article. The percentage concentration (or phr) of the non-Aloe vera botanical extract depends upon the type of application to the article and/or the drying conditions. Preferably the non-Aloe vera botanical extract selected is Nopal extract. The additive(s) may be added in usual amounts known in the industry. Preferably the additive selected to be added to the non-Aloe vera botanical extract is Vitamin E.

As best shown in FIG. 11, the present invention also comprehends the method of making a flexible article having one or more layers of an elastomer and having a botanical extract of the present invention incorporated into at least one layer of the elastomer. The method of making the flexible elastomer article include the steps of compounding the botanical extract with one or more elastomers in an elastomer emulsion, solution or plastisol. The botanical extract is suspendable, soluble or miscible in the emulsion solution or plastisol. The botanical extract when added to the emulsion is characterized by the properties of stabilizing the emulsion of the elastomer used in forming the article, lowering the modulus of the elastomer, allowing for a more uniform deposition of film when forming the article, providing anti-oxidant protection to the finished article, and modifying the rheology of the flexible article by decreasing unwanted flow of the elastomer emulsion when forming the article.

In FIG. 11, Step 11.1, the article is prepared according to standard techniques prior to elastomer dipping, molding, or extruding.

In Step 11.2 a layer of an elastomer compounded with a botanical extract of the present invention for the flexible article is formed by dipping, molding, or extruding. The elastomer solution, emulsion, or plastisol is prepared (compounded) according to standard processes in the industry. The botanical extract is incorporated into (compounded with) the emulsion, solution, or plastisol. When the article is dipped, article formers are typically used. Typically for gloves and other flexible articles, formers are dipped into a tank containing the elastomer with the emulsion, or solution, or plastisol compounded with the botanical extract. For some devices, like a cervical cap, a mold is filled with the compounded elastomer (emulsion, solution, or plastisol) with the botanical extract as appropriate. In other applications for flexible articles, the elastomer emulsion or solution or plastisol compounded with the botanical extract is extruded.

In Step 11.3, after the dipping, filling, or extruding step is performed, vulcanization, polymerization, curing, evaporating solvent/drying, and/or fusing the elastomer compounded with the botanical extract, occurs as is appropriate.

Step 11.3 incorporates the botanical extract into the elastomer. Typically for emulsions of elastomers, the incorporation of the botanical extract into the elastomer matrix occurs by vulcanization or polymerization. For elastomers that are suspendable, miscible or soluble in a solution, the incorporation of the botanical extract into the elastomer matrix usually occurs by evaporation of the solution. Typically for plastisol suspendable, soluble or miscible elastomers, the incorporation of the botanical extract into the elastomer matrix occurs by fusing the plastisol. The elastomer with the botanical extract therein is now disposed in a layer of the article (this is also referred to herein as incorporating the botanical extract into the elastomer matrix). Steps 11.1-11.3, for the flexible article are repeated for each layer of the article into which the botanical extract is to be incorporated. The botanical extract includes extracts preferably selected from the group of extracts of Aloe vera, Nopal, okra, kelp, tamarind, psyllium, carrageenan, chia, flax, carob, guar, xanthan, konjac, cassia, tara, karaya, ghatti, tragacanth, glucomannan, galactomannan, a laboratory produced polysaccharide, and mixtures (combinations) thereof. In the preferred embodiment, the botanical extract consists of Aloe vera and/or Nopal. In the most preferred embodiment Aloe vera extract is selected. The phr are as described supra for the incorporation of the botanical extract into one or more elastomer layers. As is appreciated by those skilled in the art, the method of making flexible elastomer articles may be generalized to articles other than gloves.

In addition to making the flexible elastomer articles with the botanical extract incorporated therein, the present invention also comprehends the step of applying a non-Aloe vera coating material to the wearer contacting surface of an article, as shown in FIG. 12. The non-Aloe vera coating material, of the present invention, is a non-Aloe vera botanical extract, e.g., a non-Aloe vera mucinous botanical extract or laboratory produced polysaccharide. The non-Aloe vera coating material is a non-Aloe vera botanical extract as disclosed, supra, having thixotropic properties of a liquid biopolymer, moisture regulating properties, lubricating and moisturizing properties and therapeutic components. The therapeutic components include one or more of wound healing properties, anti-inflammatory properties, anti-microbial properties, analgesic properties, and anti-aging properties. The non-Aloe vera coating material is prepared as described above by preferably selecting a non-Aloe vera botanical extract(s), e.g., preferably from the group of extracts of Nopal, okra, kelp, tamarind, psyllium, carrageenan, chia, flax, carob, guar, xanthan, konjac, cassia, tara, karaya, ghatti, tragacanth, glucomannan, galactomannan, a non-Aloe vera laboratory produced polysaccharide and mixtures thereof, having the aforementioned properties. In addition to the non-Aloe vera botanical extract, the non-Aloe vera coating material may contain one or more non-Aloe vera additives (also "additives") selected from Vitamin A, Vitamin E, Vitamin C, Vitamin $B_3$, Vitamin $B_5$, jojoba, rose hips, tea tree oil, flax seed oil, palm oil, acetylsalicylic acid, and mixtures thereof. The additives are selected in customary concentrations. The non-Aloe vera coating material (also "coating material") is applied by spraying, dipping, spray tumbling, or soaking and in the percent composition and/or phr for coating material as described supra. The coating material is solidified preferably by drying to the wearer contacting surface of the article. The coating material is mechanically and non-covalently linked to the elastomer material with the non-Aloe vera botanical extract disposed thereon.

As described previously herein, the non-Aloe vera coating material of the present invention may be applied to any flexible article (see FIGS. 5-7 and 21 for gloves) (not necessarily just the flexible article of the present invention) having at least one elastomer layer and having a wearer contacting surface and a distal surface disposed distal to the wearer contacting surface. The flexible elastomer article has at least one layer of elastomer between the wearer contacting surface and the distal surface. The non-Aloe vera coating material containing the non-Aloe vera botanical extract is applied to the wearer contacting surface or to the distal surface or to both. Preferably the coating material is applied to the wearer contacting surface. For certain articles such as condoms, the coating material may be applied to both surfaces. The coating material has the aforementioned properties and contains the aforementioned non-Aloe vera botanical extract(s); and the aforementioned additives (supra) may be added.

The flexible articles to which the non-Aloe vera coating material may be applied include a glove, a catheter, a stent, an incontinence device having a sheath or sheath-type construction, a condom, a cervical cap, a diaphragm, an elastomer sheet, a finger cot, a sheath for use with a medical device or a balloon for use with a balloon catheter, a urinary catheter, a rectal catheter, a feeding tube, an endotracheal tube, or a cardiac catheter.

The method of applying the non-Aloe vera coating material includes a Step 12.1 of preparing a flexible article after vulcanizing, polymerizing, evaporating solvent, and/or fusing, etc., to receive a coating material applied to the wearer contacting surface or to the distal surface, or to both. Then, in Step 12.2, the non-Aloe vera coating material of the present invention is applied by having the article dipped, sprayed, tumble sprayed, or soaked so the non-Aloe vera coating material is disposed on a selected surface (wearer contacting surface or distal surface or both) of the flexible article. In Step 12.3, the coating material is solidified preferably by drying on to the selected surface of the flexible article.

To prepare flexible elastomer articles of the present invention having both a botanical extract incorporated into one or more layer(s) and a non-Aloe vera coating material applied to a surface, the methods described in FIGS. 11 and 12 are used.

As will be described now, preferred methods of making gloves of the present invention will be disclosed in FIGS. 13-21. The general method of making gloves of the present invention is disclosed in FIG. 13. The methods of coating the flexible articles and making flexible articles according to the present invention can be understood from the specific examples of the gloves herein, and generalized to other flexible articles.

Figure 13:
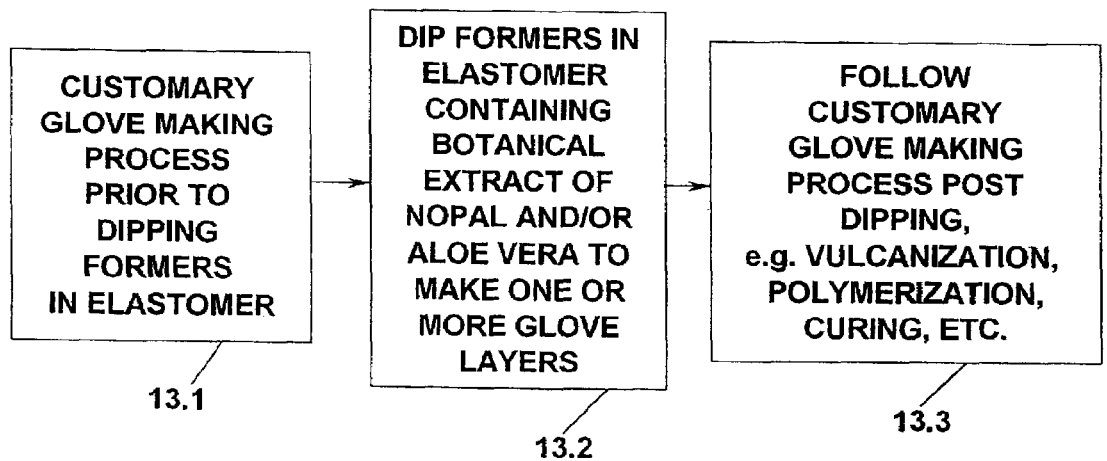
FIG. 13 is a schematic flow diagram showing a dipping process for making a glove of the present invention.

The process of making gloves of the present invention may be more generalized, as shown in FIG. 13. FIG. 13 corresponds to the discussion regarding gloves shown in FIGS. 2-4, 8-10, 20 and 22-23. Referring to FIG. 13, in Step 13.1 the process of glove making of the present invention utilizes customary glove making procedures prior to dipping the formers into an elastomer compounded with the botanical extract. In Step 13.2, the botanical extract (preferably Aloe vera 108 and/or Nopal 110) is compounded with elastomer(s) and the formers are dipped into the compounded elastomer. The composition of the Aloe vera 108 and/or the Nopal extract 110 are as disclosed supra, preferably about 0.2 to 2.5 phr in the finished product.

In Step 13.3, the gloves are processed according to usual techniques, e.g. vulcanization, polymerization, curing, fusing, solvent evaporation, etc. to form a glove having Aloe vera and/or Nopal or within the matrix of the elastomer material of the glove. The general process of FIG. 13, may be used for making single layer gloves, bilaminar gloves and multi-layer gloves.

The methods of making gloves of FIGS. 2-4, 8-10, and 22-23 of the present invention utilize the general prior art glove making methods, but add a new material, the botanical extract e.g., preferably the botanical extract of Aloe vera 108 and/or Nopal 110, to be incorporated into the elastomer matrix of the glove. This is best seen on FIGS. 14, 16, 17, and 19 for most preferably using an NRL dip with Aloe vera incorporated in a glove elastomer layer.

FIGS. 14-20 disclose the methods of making disposable gloves containing both a botanical extract in the elastomer matrix of the glove and a non-Aloe vera botanical extract (non-Aloe vera coating material) coated on an interior surface of the glove. In FIGS. 14-19, for a preferred embodiment, the glove is made from NRL and the botanical extract incorporated into the NRL matrix is an Aloe vera extract preferably in a concentration to achieve approximately 0.2 to 2.5 phr in the finished glove as previously discussed herein.

Alternatively, in lieu of NRL, any other elastomer which is suspendable into an emulsion, or any elastomer that is suspendable, soluble or miscible in a solvent or plastisol and wherein the botanical extract is suspendable, soluble or miscible, and mixtures thereof, may be used as discussed herein.

Referring generally to FIGS. 14-19, the four most likely manufacturing methods are depicted. These methods demonstrate as closely as possible all the likely steps to be taken should any of them be adopted for use. They will be summarized into simple steps for presentation in the following descriptions.

In FIGS. 15, 16, 18, 19, 20, and 21, the non-Aloe vera coating material is a non-Aloe vera botanical extract as disclosed supra, by itself, or with one or more added compounds (non-Aloe vera additives), including, but not limited to, Vitamin E, Vitamin A, Vitamin C, Vitamin $B_3$, Vitamin $B_5$, jojoba, rose hip, tea tree oil, flax seed oil, palm oil, and/or acetylsalicylic acid. The non-Aloe vera botanical extract is prepared preferably as a 5% to 20% solution in a water and/or ethanol mixture. The non-Aloe vera additives are used in concentrations known in the art. For a batch of 8,000 to 10,000 gloves, 2 kg of a non-Aloe vera botanical extract is made into a solution. Such a non-Aloe vera botanical extract coating material solution is preferably applied by spraying in a rotary tumbler in the case of an off-line application, or as a dipping solution in the case of an on-line application mode. For the latter case, depleted solution is continually topped up with fresh input. Preferably, a 5% to 20% solution (water and/or ethanol) of Nopal extract is used. Yet, alternatively, a 5% to 20% solution (water and/or ethanol) of one or more of the following extracts may be used: okra extract, kelp extract, Nopal extract, tamarind extract, psyllium extract, carrageenan extract, chia extract, flax extract, carob extract, guar extract, xanthan extract, konjac extract, cassia extract, tara extract, karaya extract ghatti extract, tragacanth extract, galactomannan, glucomannan, or a non-Aloe vera laboratory produced polysaccharide. Alternatively, the amount of non-Aloe vera botanical extract, used for coating may be also expressed in phr of coating material based on dry weight of the finished article. The phr of coating material may be governed by applicable standards. Most preferably Nopal extract and Vitamin E are used for the non-Aloe vera coating material.

In FIGS. 14-19, "START" denotes the start of the Dipping Operation and "END" denotes the end of the Dipping Operations.

Figure 14:
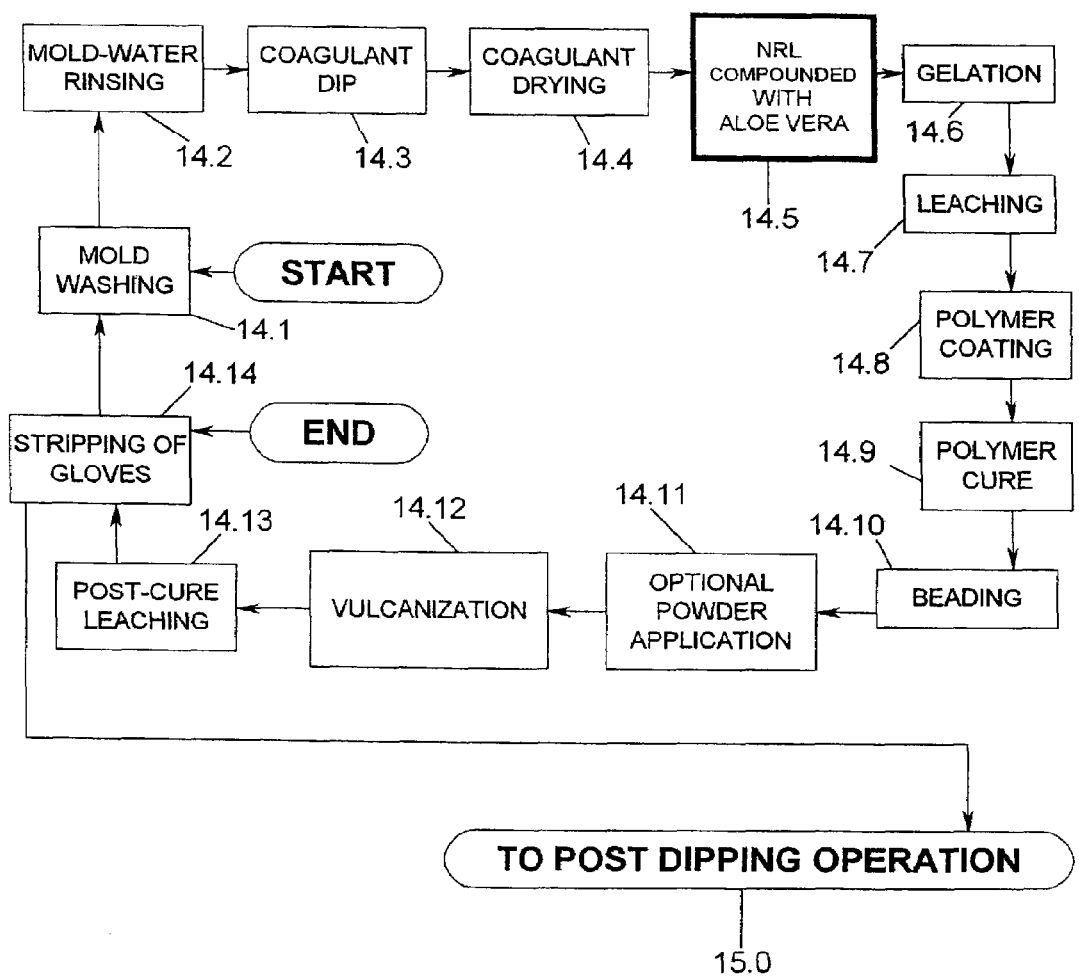
FIG. 14 is a schematic flow diagram showing a dipping process for on-line polymer coating of gloves followed by off line washing/chlorination.
Figure 15:
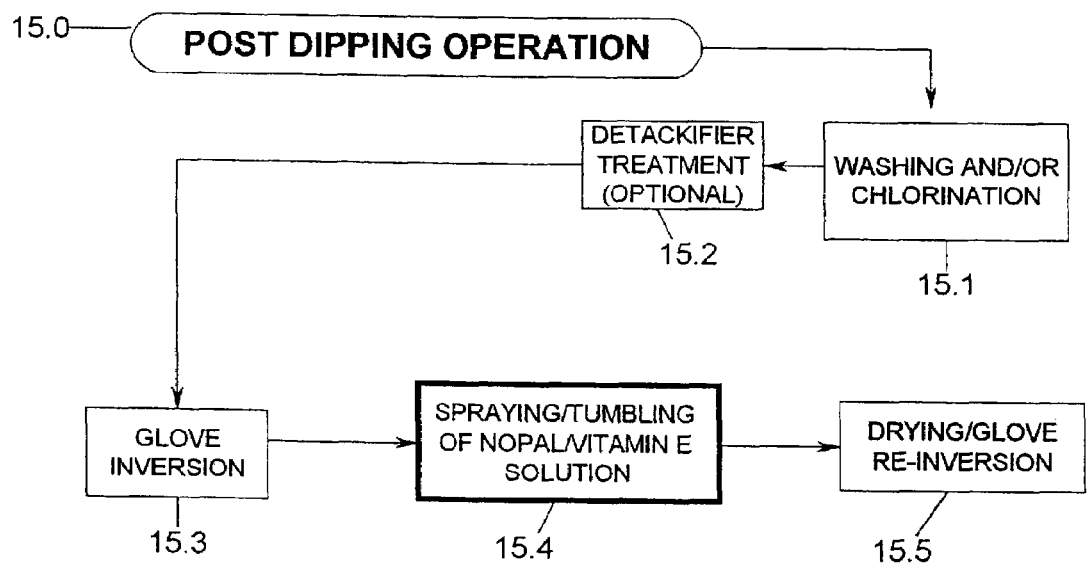
FIG. 15 is a schematic flow diagram showing a process following the dipping operation of FIG. 14.

Referring now to FIGS. 14 and 15, this method of making gloves of the present invention and applying the coating involves on-line polymer coating followed by washing and/or chlorination off-line. After drying, the gloves are inverted inside out, sprayed with the aforementioned prepared preferred Nopal extract/Vitamin E solution, tumble dried, and re-inverted back. The dipping operation is illustrated in FIG. 14, and the post-dipping operation is illustrated in FIG. 15. The term "Operations" also means "process" or "method".

FIG. 14 discloses a glove manufacturing method (process) of the present invention providing a single layer glove having a botanical extract incorporated into the elastomer matrix of the glove. Specifically, FIG. 14 discloses a preferred dipping operation using a preferable NRL elastomer having preferably Aloe vera extract incorporated into the elastomer matrix. However, other elastomers may be used.

In Step 14.1, the glove formers or molds are washed. In Step 14.2, the molds are water rinsed. In Step 14.3, the molds are dipped in a standard coagulant mix. In Step 14.4, the coagulant is dried using standard conditions. In Step 14.5, the molds having dried coagulant thereon, are dipped in an NRL emulsion compounded with an amount of Aloe vera extract therein to make a finished product having approximately 0.2 to 2.5 phr of Aloe vera to NRL. In Step 14.6, gelation occurs. A film is deposited on the formers. The film contains the Aloe vera and the NRL. In Step 14.7, leaching is done. In Step 14.8, a polymer coating is applied, preferably silicone is either sprayed or dipped onto the film. In Step 14.9, the polymer coating is cured. In Step 14.10, the materials are beaded to form a cuff. In Step 14.11, if silicone is not used, a powder, such as cornstarch, may be applied. In Step 14.12, the materials on the molds are vulcanized thereby incorporating the Aloe vera extract into the matrix of the NRL. In Step 14.13, post-cure (post-vulcanization) leaching is done. In Step 14.14, the gloves are stripped from the molds. Steps 14.1-14.4, and 14.6-14.14 use known in the art techniques.

At this point, the gloves of the present invention may be processed according to standard known in the art, off-line or post-stripping operations.

However, in the most preferred embodiment of the present invention, the gloves are also coated on the interior wearer contacting surface with a non-Aloe vera coating material, preferably a non-Aloe vera botanical extract. The said extract is used by itself or with the addition of an added compound (additive) using an off-line process of the present invention. FIG. 15 illustrates a preferred off-line process (post dipping operation) using a preferred mixture of Nopal extract and Vitamin E (hereinthroughout also, Nopal/Vitamin E).

Alternatively, gloves made according to standard dipping procedures may use the method of applying a coating disclosed in FIG. 15 to apply a non-Aloe vera coating material, preferably a non-Aloe vera botanical extract to the inside wearer contacting surface of the glove.

Referring now to FIG. 15 in Step 15.1, the gloves undergo washing and/or chlorination. In Step 15.2, an optional detackifier may be applied. In Step 15.3, the gloves are inverted. In Step 15.4, the aforementioned preferred Nopal/Vitamin E solution is spray-tumbled on the gloves. In Step 15.5, the gloves are tumble dried and re-inverted back.

Figure 16:
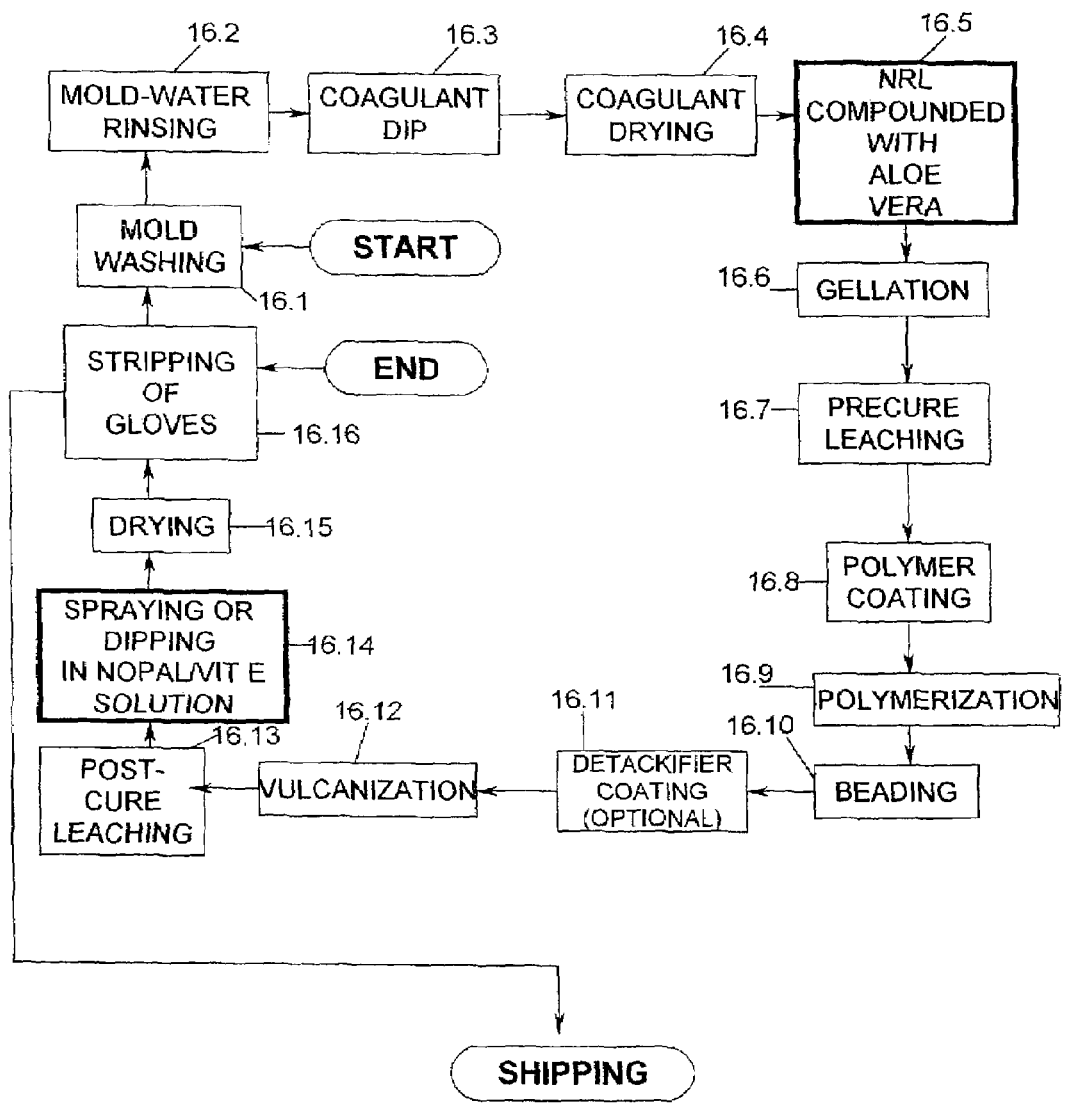
FIG. 16 is a schematic flow diagram showing a dipping process for a powder free coagulant system coupled with on-line polymer coating of gloves.

FIG. 16 discloses the use of powder free coagulant system coupled with on-line polymer coating of gloves. On-line coating of the preferred prepared Nopal/Vitamin E mixture is carried out after the post cure leaching operation. The dipping operation is illustrated in FIG. 16.

FIG. 16 discloses a glove manufacturing method of the present invention of providing a single layer glove of the present invention having a botanical extract in the elastomer matrix of the glove and having a non-Aloe vera coating material, preferably a non-Aloe vera extract applied to the interior wearer contacting surface of the glove. More specifically, FIG. 16 discloses a preferred dipping operation using a preferred NRL elastomer emulsion compounded with a preferred Aloe vera extract, and having a preferred Nopal/Vitamin E solution applied to the interior wearer contacting surface of the glove of the present invention. However, other elastomers may be used.

In Step 16.1, the glove formers or molds are washed. In Step 16.2, the molds are water rinsed. In Step 16.3, the molds are dipped in a standard coagulant mix. In Step 16.4, the coagulant is dried using standard conditions. In Step 16.5, the molds having dried coagulant thereon are dipped into an NRL emulsion having a sufficient quantity of Aloe vera extract therein to produce a finished glove having approximately 0.2 to 2.5 parts of Aloe vera per hundred weight of NRL. In Step 16.6, gelation occurs. A film of the compounded NRL and Aloe vera is deposited on the molds. In Step 16.7, extensive pre-cure leaching is performed. In Step 16.8, a polymer coating is applied to the materials on the molds. In Step 16.9, the polymer coating is polymerized. In Step 16.10, the materials on the mold are beaded to form a cuff. In Step 16.11, an optional detackifier coating is applied. In Step 16.12, the materials on the molds are vulcanized thereby incorporating the Aloe vera into the matrix of the NRL. In Step 16.13, post-cure leaching is done. In Step 16.14, the molds with the gloves thereon are dipped or sprayed in the aforementioned preferred non-Aloe vera coating material, e.g., solution of Nopal/Vitamin E. In Step 16.15, the gloves are dried, and the preferred Nopal/Vitamin E coating is disposed within the interior of the glove on the wearer contacting surface. In Step 16.16, the stripping of the gloves from the molds is the end of the dipping operation. The gloves are then prepared for shipment.

Figure 17:
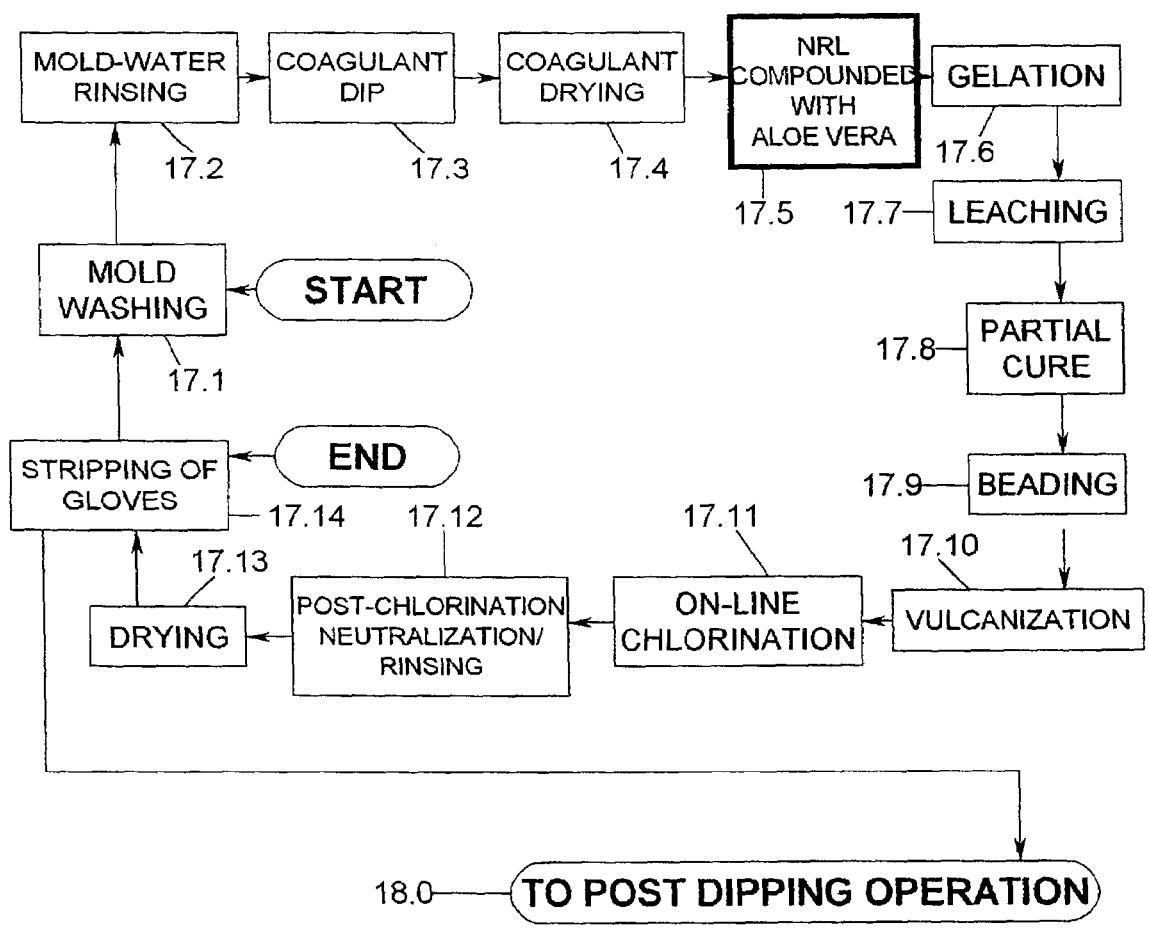
FIG. 17 is a schematic flow diagram showing a dipping process for on-line chlorination of gloves followed by off-line washing/chlorination.
Figure 18:
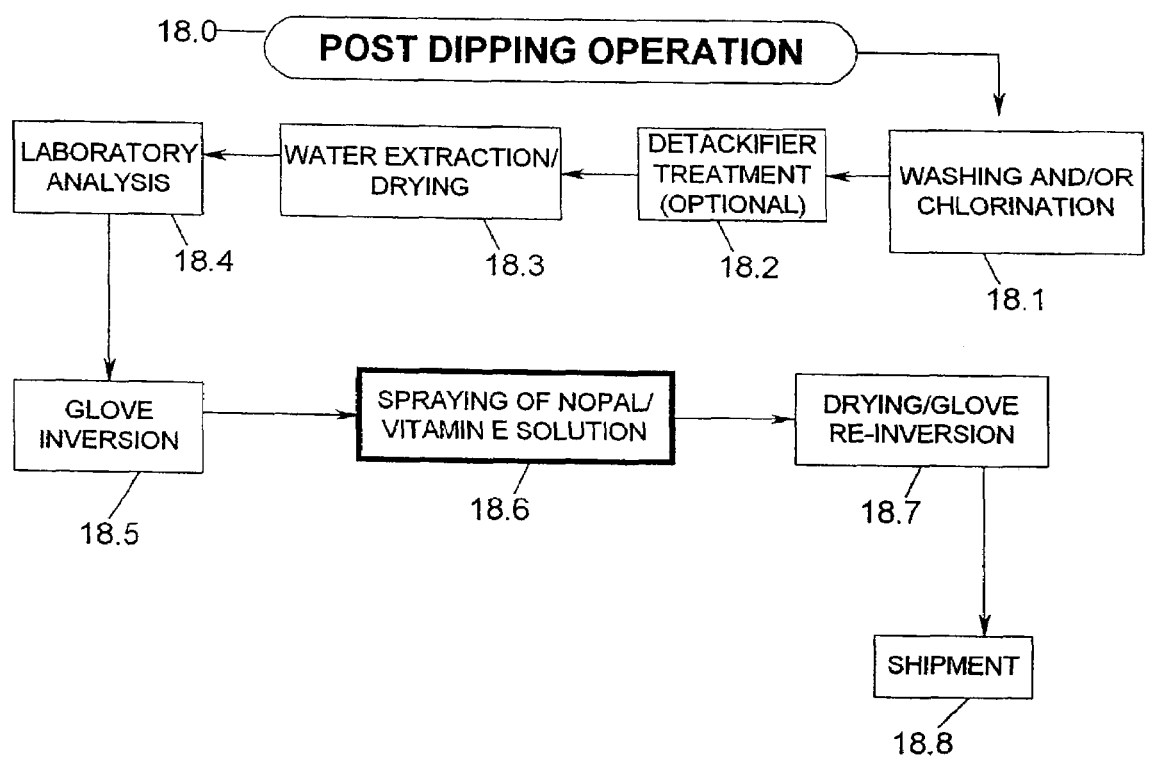
FIG. 18 is a schematic flow diagram showing a process following the dipping operation of FIG. 17.

FIGS. 17 and 18, disclose on-line chlorination of gloves followed by washing/chlorination off-line. After drying, the gloves are inverted inside out, sprayed with the preferred prepared Nopal/Vitamin E solution, tumble dried, and re-inverted back right side out. The dipping operation is illustrated in FIG. 17, and the post-dipping operation is illustrated in FIG. 18.

FIG. 17 discloses a glove manufacturing method of the present invention of providing a single layer glove of the present invention having a botanical extract in the matrix of the elastomer from which the glove is made. More specifically, FIG. 17 discloses a preferred dipping operation using a preferred NRL having a preferred Aloe vera extract incorporated therein. However, other elastomers may be used.

In Step 17.1, the glove molds are washed using an acidic or a basic solution to remove residual NRL. In Step 17.2, the molds are water rinsed. In Step 17.3, the molds are dipped in coagulant. In Step 17.4, the coagulant is dried on the molds. In Step 17.5, the molds having the dried coagulant thereon are dipped in an NRL emulsion compounded with an amount of Aloe vera therein to make a finished glove having between 0.2 to 2.5 parts of Aloe vera per hundred weight of NRL. In Step 17.6, gelation occurs. A deposited film of Aloe vera and elastomer are on the molds. In Step 17.7, leaching is done. In Step 17.8, the materials on the molds are partially cured. In Step 17.9, the materials are beaded to form a cuff. In Step 17.10, the materials on the molds are partially vulcanized thereby incorporating the Aloe vera into the NRL matrix. In Step 17.11, on-line chlorination is done. Chlorination changes the surface of the glove making it easier for a surface coating to adhere to the surface. In Step, 17.12, the gloves on the molds are treated to a post-chlorination neutralization and rinsing step. In Step 17.13, the gloves on the molds are dried.

At this point, the gloves may be stripped off the molds in Step 17.14 ending the dipping operation or may be processed according to standard, known in the art, post dipping operations where the gloves are stripped off the molds.

However, in the most preferred embodiment of the present invention, the gloves are also coated on the interior wearer contacting surface with a non-Aloe vera coating material, preferably a non-Aloe vera botanical extract. The said extract is used by itself or with the addition of an added compound (additive) using the post dipping operation of the present invention.

FIG. 18 illustrates a preferred post dipping operation using a preferred mixture of Nopal extract and Vitamin E. Alternatively, gloves made according to standard glove making procedures may use the procedure used in FIG. 18 to apply a preferred a non-Aloe vera coating material, preferably a non-Aloe vera botanical extract to the inside of the wearer contacting surface of the glove.

The stripping of the gloves from the molds of Step 17.14 occurs in the post dipping operation of FIG. 18.

In Step 18.1, the gloves on the molds undergo washing and/or chlorination. In Step 18.2, the gloves may be treated with a detackifier; typically silicone is used. In Step 18.3, water is extracted from the gloves and/or the gloves are dried. In Step 18.4, a laboratory analysis is performed when chlorination has occurred to ensure appropriate product and effluent neutralization. In Step 18.5, the gloves are inverted. In Step 18.6, the aforementioned preferred non-Aloe vera coating material, preferably a Nopal/Vitamin E solution is sprayed on the inverted gloves. In Step 18.7, the gloves are dried and then re-inverted. In Step 18.8, the gloves are prepared for shipment.

Figure 19:
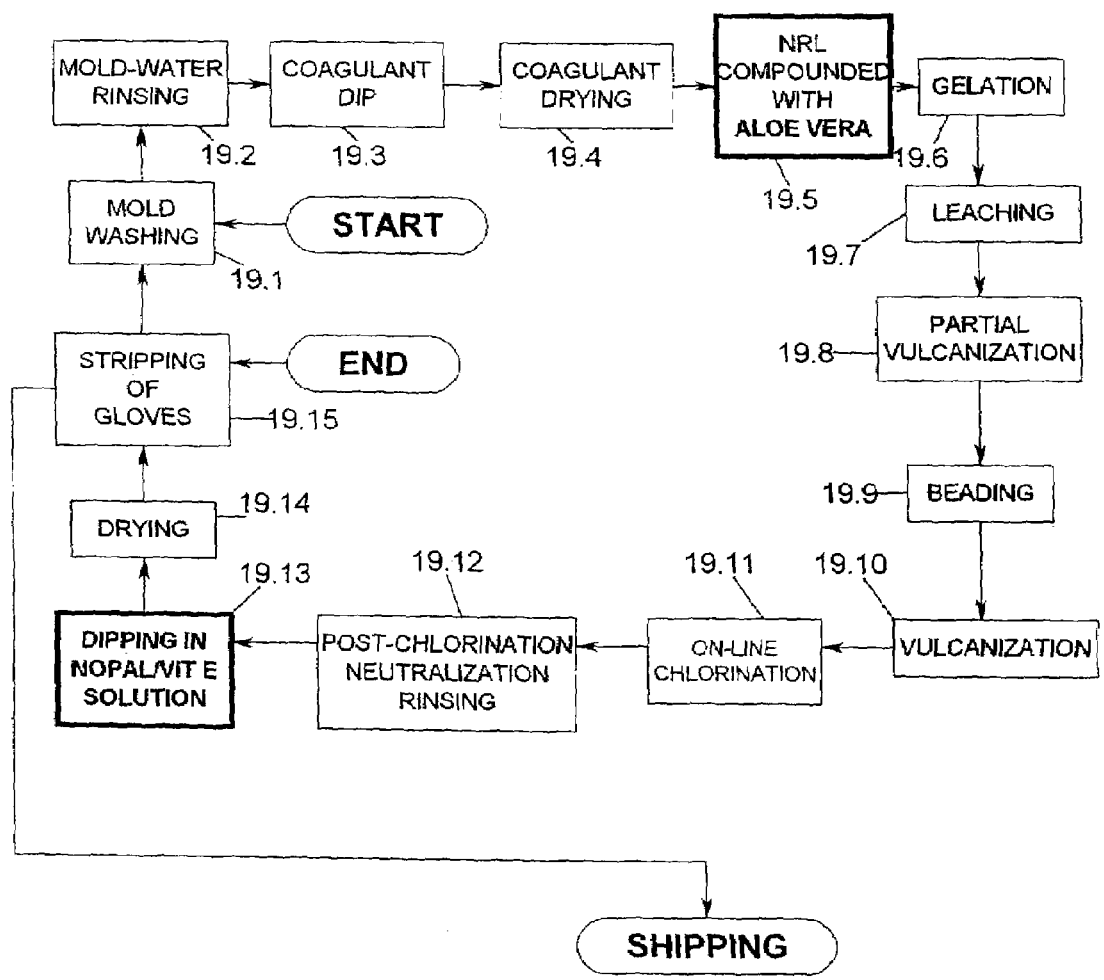
FIG. 19 is a schematic flow diagram showing a dipping process for a powder free coagulant system coupled with on-line chlorination of gloves.

FIG. 19 discloses the use of powder free coagulant system coupled with on-line chlorination of the gloves. On-line coating of the prepared preferred Nopal/Vitamin E mixture is carried out after the post chlorination rinsing operation. The dipping operation is illustrated in FIG. 19.

FIG. 19 discloses a glove manufacturing method of the present invention providing a single layer glove of the present invention having a botanical extract in the elastomer matrix of the glove and having a non-Aloe vera coating material, preferably a non-Aloe vera extract applied to the interior surface of the glove. More specifically, FIG. 19 discloses a preferred dipping operation using a preferred NRL elastomer having a preferred Aloe vera botanical extract incorporated therein, and having a non-Aloe vera botanical coating material, preferably a Nopal/Vitamin E solution, applied to the interior wearer contacting surface of the glove. However, other elastomers may be used.

In Step 19.1, the glove molds are washed. In Step 19.2, the molds are rinsed with water. In Step 19.3, the molds are dipped in a coagulant. In Step 19.4, the coagulant is dried onto the mold. In Step 19.5, the molds having dried coagulant thereon are dipped into an NRL emulsion having an amount of Aloe vera extract therein sufficient to make a finished product having approximately 0.2 to 2.5 parts of Aloe vera per 100 weight NRL. In Step 19.6, a gelation occurs and a film of Aloe vera and NRL is deposited on the mold. In Step 19.7, leaching is done. In Step 19.8, the materials on the molds are partially vulcanized. In Step 19.9, the materials are beaded to form a cuff. In Step 19.10, the materials on the molds are vulcanized thereby incorporating Aloe vera into the NRL matrix. In Step 19.11, an on-line chlorination procedure is performed. In Step 19.12, the gloves are treated to a post-chlorination neutralization rinsing. In Step 19.13, the gloves are dipped in the aforementioned preferred non-Aloe vera coating material of a Nopal/Vitamin E solution. In Step 19.14, the gloves are dried; and in Step 19.15, the gloves are stripped off the molds. The gloves are then readied for shipment.

Figure 20:
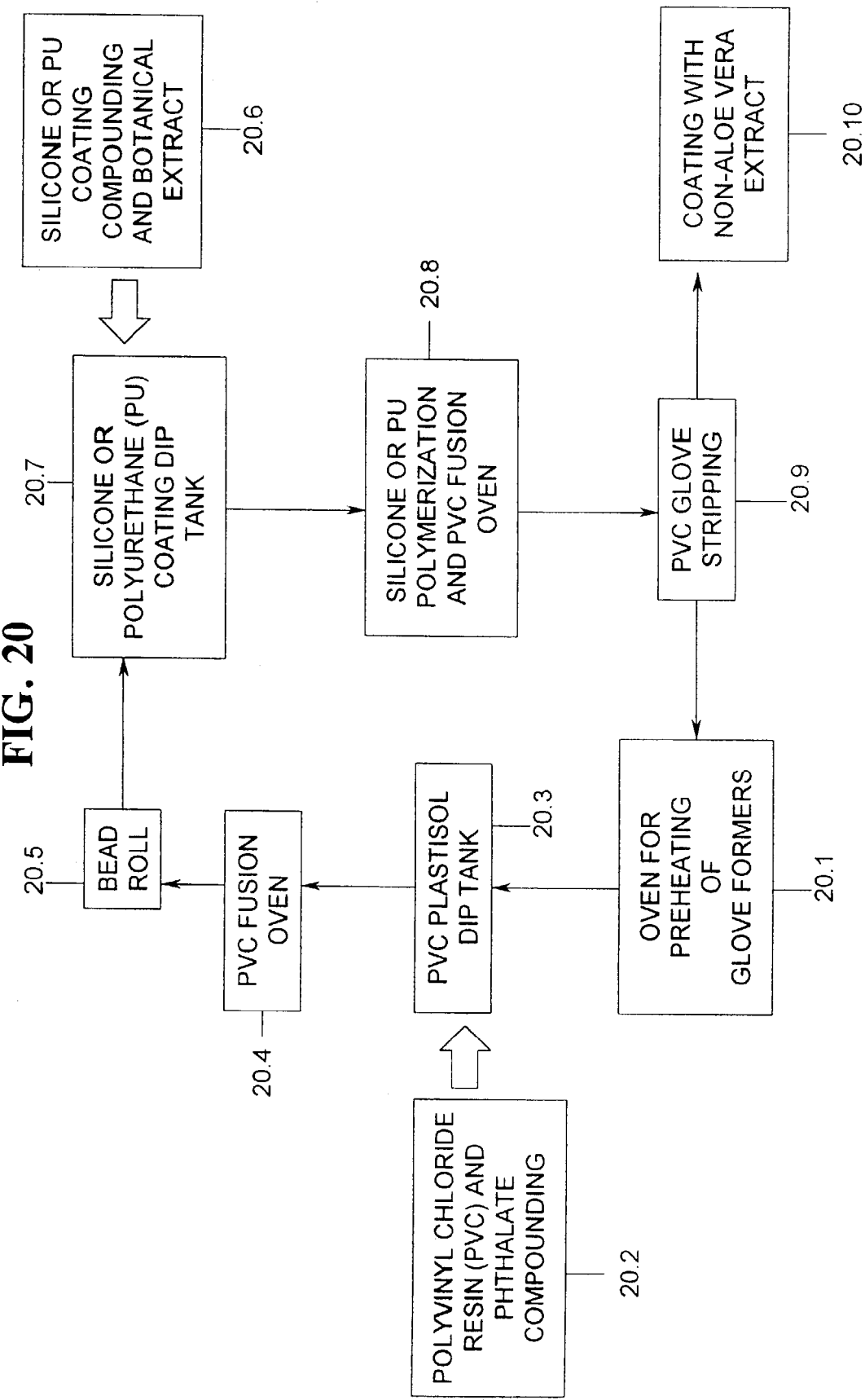
FIG. 20 is a schematic flow diagram showing a method of making a glove of the present invention.

In another embodiment of the present invention, the powder free process of manufacturing PVC gloves of the present invention uses polyester with good water solubility for polyurethane epoxy, and a mixture of methyl-ethyl-ketone, isobutyl-ketene and isopropyl alcohol may be used to prevent the surface of PVC gloves from deterioration due to corrosion, so to avoid affecting the appearance and performance of the gloves. Alternatively, a water based silicone oil (silicone) and a catalyst form a film coating of a PVC substrate. FIG. 20 discloses a glove manufacturing method of the present invention providing a bilaminar glove having a botanical extract in the elastomer matrix of the glove. Specifically, FIG. 20 discloses a preferred dipping operation using a PVC and silicone or PU elastomer. The silicone or PU preferably has an Aloe vera extract incorporated in the elastomer matrix.

In Step 20.1, an oven is prepared for pre-heating glove formers. In Step 20.2, the polyvinyl chloride (PVC) resin and the phthalate are compounded and poured into a dip tank (PVC plastisol dip tank). In Step 20.3, the PVC plastisol dip tank accepts the glove formers and the glove formers are coated with a coating of a PVC plastisol. In Step 20.4, the glove formers, with the coating of the PVC plastisol, enter a PVC fusion oven. In Step 20.5, a bead roll cuff is applied to the fused PVC. In Step 20.6, the silicone or polyurethane coating is compounded with a botanical extract of the present invention. Preferably the botanical extract is Aloe vera extract in a quantity sufficient to produce a concentration of approximately 0.2 to 2.5 parts of Aloe vera to one hundred weight of silicone or polyurethane. In Step 20.7, the glove formers are dipped into the silicone or polyurethane dip tank which contains the botanical extract. In Step 20.8, silicone or PU are polymerized on the surface of the PVC concurrently with the PVC fusion. The botanical extract is incorporated into the silicone matrix or the PU matrix. After fusion, in Step 20.9 the gloves having the botanical extract, Aloe vera, incorporated into one layer thereof are stripped from the glove formers. Alternatively, in Step 20.10, the gloves are then coated with a non-Aloe vera coating material, preferably a non-Aloe vera botanical extract, most preferably a 5% to 20% solution of Nopal extract to which Vitamin E (in amounts customary in the art) is added, according to the previously discussed methods of coating gloves.

Figure 21:
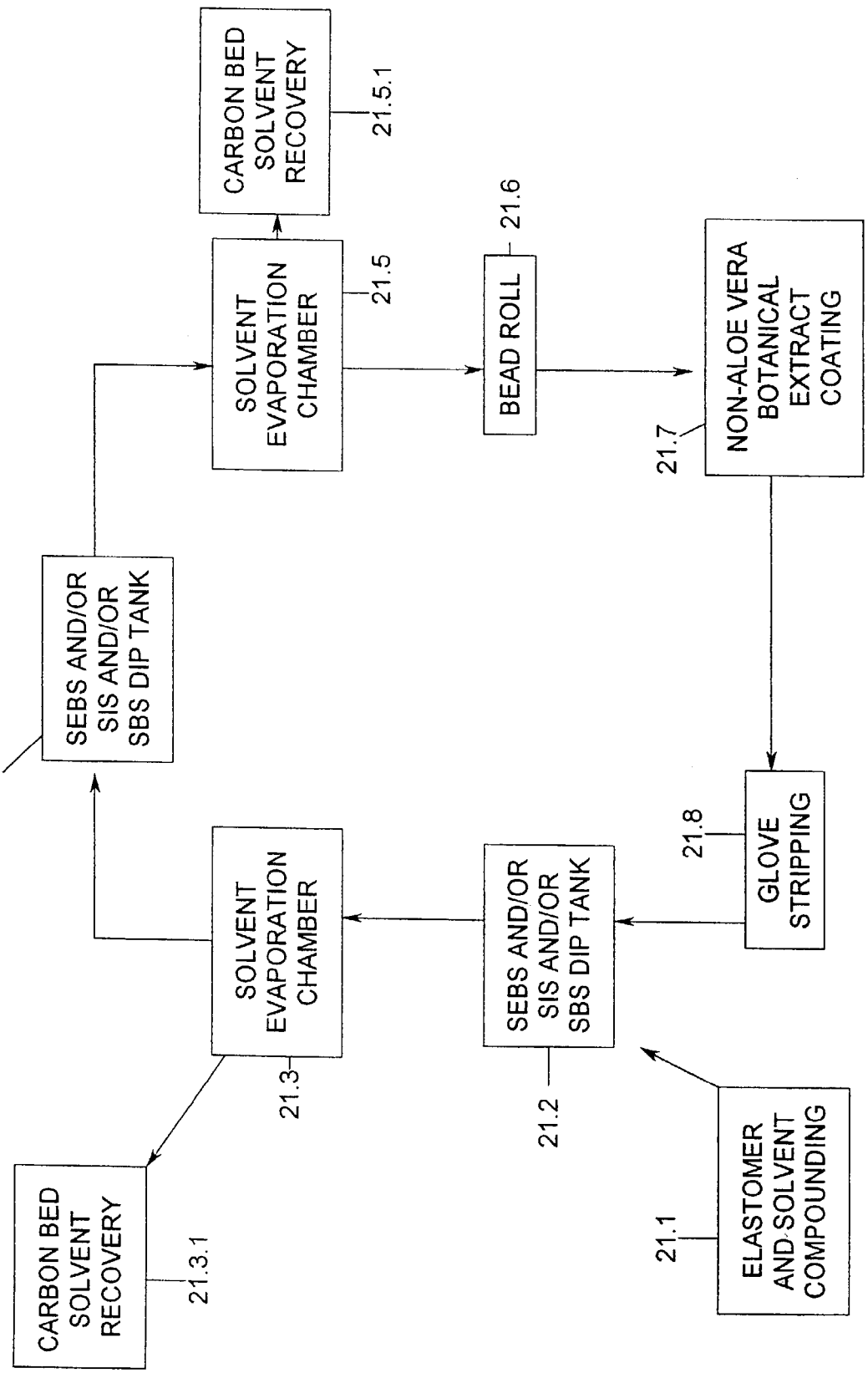
FIG. 21 is a schematic flow diagram showing a method of coating a glove of the present invention.

FIG. 21 shows a coating method of the present invention, of applying a non-Aloe vera botanical extract (non-Aloe vera coating material) onto a wearer contacting surface of a glove wherein the gloves are made of SIS and/or SBS and/or SEBS. The preferred non-Aloe vera coating material is preferably a Nopal extract in the preferred concentration or phr of coating material to which a Vitamin E is added, as disclosed supra. Referring now to FIG. 21, the selected elastomer, e.g., SEBS and/or SIS and/or SBS, and suitable solvent (solution) are compounded in Step 21.1. Glove formers are dipped into a tank of SEBS and/or SIS and/or SBS in Step 21.2. In Step 21.3, the solvent is evaporated from the elastomer in a solvent evaporation chamber. The solvent preferably goes to a carbon bed solvent recovery system in Step 21.3.1. The glove formers then proceed to a dip tank having SEBS and/or SIS and/or SBS for dipping either another layer of different elastomer thereon or dipping the same layer of elastomer thereon. In Step 21.5, the solvent is evaporated in a solvent evaporation chamber. The evaporated solvent preferably goes to a carbon bed for solvent recovery in Step 21.5.1. The formers with the selected elastomers therein are moved to a bead roll in Step 21.6 wherein the cuff of the glove is rolled. In Step 21.7, a non-Aloe vera coating material, preferably a non-Aloe vera botanical extract of the present invention, is coated onto the surface of the glove. Preferably a 5% to 20% solution of Nopal extract is sprayed or dipped on the glove and the gloves are dried. Most preferably the Nopal solution contains Vitamin E. The Nopal coating is disposed on the glove layer having the wearer contacting surface. In Step 21.8, the gloves are stripped from the mold and the glove making process is completed.

The dry donning lubricity of gloves of FIGS. 15, 16, 18, 19, 20, and 21 coated with the preferred non-Aloe vera botanical extract Nopal and non-Aloe vera additive/Vitamin E mixture is unaffected and even slightly improved as gauged by the subjective, known in the industry, donning tests. With a rating of 1 to 5, where 1 is worst and 5 is best, the gloves so coated have a dry donning lubricity rating of 5. Doubling and tripling the dosage of Nopal/Vitamin E on the gloves does not materially affect such a rating.

Figure 24:
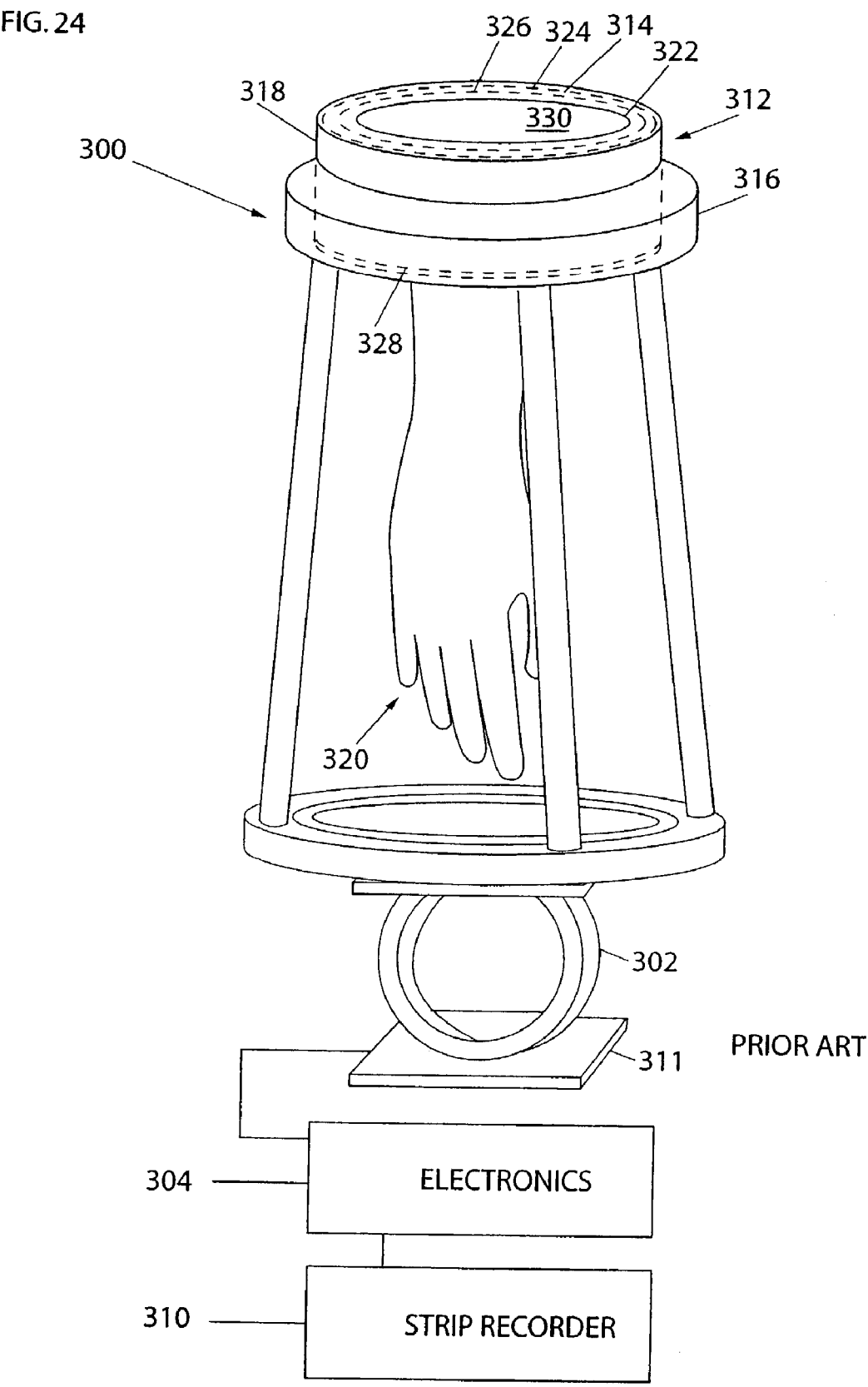
FIG. 24 is a view of a prior art load tester for measuring donning-force of a glove.

Alternatively, the quantity of non-Aloe vera botanical extract used in the aforementioned gloves is sufficient to overcome the rubber or plastic blocking and provide adequate lubriciousness when dry donning is used in the present invention. This is accomplished by using a quantity of non-Aloe vera botanical extract as a non-Aloe vera coating material such that the gloves so coated have not greater than 2500 g frictional donning forces. Donning forces may be measured using a prior art load tester, such as shown in FIG. 24 and testing procedures disclosed in Cote et al., 1998 Journal of Biomedical Materials Research, 43:331-337, page 333 and; Fisher et al., 1996 Appl. Biomater. 33:291-295, page 292, all the disclosures of which are hereby incorporated by reference) is used in the present invention.

As best shown in FIG. 24, one prior art way of measuring donning force is to use a load tester 300. The load tester 300 is not drawn to scale. The load tester 300 is attached to a calibrated scale 302 which is connected via electronics 304 to a strip recorder 310. The scale 302 is calibrated preferably every half hour using various gram and kilogram weights. Scale 302 is fastened to a rigid base 311. The load tester 300 has a ring assembly 312 having two tapered interfitting rings 314, 316 (preferably 125 mm diameter). A cuff 318 of a glove 320 made of elastomer(s) is stretched over and around tapered ring 314 and engaged between rings 314, 316 of the load tester 300. Tapered ring 314 is shown in hidden line. A cuff 318 of the medium hand-sized glove 320 is secured between rings 314, 316. The glove 320 is sized to fit a hand of a subject. Securing the glove 320 between the two rings 314, 316 makes an opening 322 into which the hand of the subject may be inserted. Tapered ring 314 has edges 324, 326 which are shown in hidden line. Edge 328 of cuff 318 is also shown in hidden line. Shading for the elastomer material used for the glove 320 is not shown to simplify the drawing, but it is to be understood that the glove 320 is made of elastomer materials. The opening 322 exposes a wearer contacting surface 330 to the hand of the subject for donnability testing.

The subject inserts his right hand into the opening 322 of the glove 320 repeatedly under repeatable speed, donning angle and distance conditions engaging the wearer contacting surface 330. Maximum force is measured by the scale 302 and recorded on the strip recorder 310. The force readings are expressed in g(grams) as the maximum force needed to don the glove, e.g, "g frictional donning force." The gloves of the present invention are coated with a quantity of non-Aloe vera botanical extract such that the gloves so coated have not greater than 2500 g frictional donning forces using the aforementioned or equivalent load tester.

As is known in the art, for the other flexible articles disclosed herein, methods similar to the methods of making and coating the gloves are used. Other flexible articles may be made having one or more elastomer layers having therein a botanical extract of the present invention, disclosed supra, preferably Aloe vera extract and/or Nopal extract; and the flexible articles may also have the non-Aloe vera coating material applied to either the wearer contacting surface of the article or to the distal most surface of the article or to both surfaces of the article. For example, where the flexible article is one of the following: a catheter, a stent, an incontinence device having a sheath or a sheath-type construction, a condom, a cervical cap, a diaphragm, an elastomer sheet, a finger cot, a sheath for use with a medical device, or a balloon for use with a balloon catheter, a urinary catheter, a rectal catheter, feeding tube, an endotracheal tube, or a cardiac catheter, the coating material is applied onto the wearer contacting surface of the flexible article.

Typically, a standard manufacturing process is followed to prepare the flexible article to receive the non-Aloe vera coating material of the present invention onto a selected surface of the article. The non-Aloe vera coating material is the non-Aloe vera botanical extract of the present invention disclosed supra with or with the non-Aloe vera additives, disclosed supra. Preferably, Nopal extract is used as the non-Aloe vera botanical extract. Preferably, Vitamin E is the additive added to the Nopal extract. The non-Aloe vera coating material is applied to the selected surface of the article, preferably corresponding to the wearer contacting surface, by spraying, dipping, spray tumbling, or soaking, or in other ways known in the art. The non-Aloe vera coating material is dried onto the selected surface, preferably the wearer contacting surface of the article. The article may have the non-Aloe vera coating applied to the distal surface in a similar manner or it may be applied to both surfaces. For such articles as condoms, having a wearer contacting surface and an outer distal surface with one or more elastomers there between, the non-Aloe vera coating material is applied to the wearer contacting surface or to the outer distal surface or to both surfaces. For such articles as condoms, the condom may also be made having one or more layers of elastomer there between and having one of the layers of elastomer having a botanical extract of the present invention incorporated therein.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention and that the scope of the present invention be limited solely by the broadest interpretation that lawfully can be accorded the appended claims.

What is claimed is:

1. A flexible glove comprising at least two layers of an elastomer and the glove having a wearer contacting surface, wherein a botanical extract having a polysaccharide therein is incorporated into at least one of the layers of the elastomer of the glove, wherein the botanical extract is free of Aloe vera and comprising Nopal extract.

2. The glove as defined in claim 1, wherein the elastomer is an elastomer that can be suspended into an emulsion and wherein the botanical extract is suspendable, soluble or miscrible in the emulsion.

3. The glove as defined in claim 2, wherein the elastomer is selected from the group consisting of a natural rubber latex, a synthetic polyisoprene, a chloroprene, a polyurethane, an acrylonitrile, a butadiene methylmethacrylate, a styrene butadiene styrene, a styrene isoprene styrene, a styrene ethylene butylene styrene, a silicone, and an acrylate-based hydrogel, any other elastomer that can be suspended into an emulsion, and mixtures thereof.

4. The glove as defined in claim 1, wherein the elastomer is an elastomer that is suspendable, soluble or miscible in a solution or a plastisol and wherein the botanical extract is suspendable, soluble, or miscible in the solution or plastisol, and mixtures thereof.

5. The glove as defined in claim 4, wherein the elastomer is selected from the group consisting of a polyvinyl chloride, a polyurethane, an acrylate-based hydrogel, a styrene butadiene styrene, a styrene isoprene styrene, a styrene ethylene butylene styrene, any other elastomer that is suspendable, soluble or miscible into the solution, or the plastisol, wherein the botanical extract is suspendable, soluble or miscible in the solution or the plastisol, and mixtures thereof.

6. The glove as defined in claim 1, wherein the glove is a disposable glove or a reusable glove.

7. The glove as defined in claim 1, wherein the glove includes an examination glove, a surgical glove, an industrial glove, a protective glove or a household glove.

8. The glove as defined in claim 1, wherein the glove is a bilaminar glove having a first layer having an outer surface, and a second layer having the wearer contacting surface, wherein the first layer and the second layer are of a similar or a different elastomer and wherein the botanical extract is incorporated into at least one layer of the glove; wherein for the layer of the glove into which the botanical extract is incorporated, the elastomer selected is any elastomer that is suspendable, soluble or miscible into an emulsion, a solution or a plastisol, wherein the botanical extract is suspendable, soluble or miscible in the emulsion, solution or plastisol, and mixtures thereof.

9. The glove as defined in claim 8, wherein the elastomer for the layer of the glove into which the botanical extract is incorporated is an elastomer selected from the group consisting of a natural rubber latex, a synthetic polyisoprene, a chloroprene, a polyurethane, an acrylonitrile, a butadiene methylmethacrylate, a styrene butadiene styrene, a styrene isoprene styrene, a styrene ethylene butylene styrene, a silicone, an acrylate-based hydrogel, a polyvinyl chloride, any elastomer that is suspendable, soluble or miscible into an emulsion, a solution or a plastisol wherein the botanical extract is suspendable, soluble or miscible in the emulsion, solution or plastisol, and mixtures thereof.

10. The glove as defined in claim 9, wherein the elastomer for the first layer is polyvinyl chloride and the elastomer for the second layer is polyurethane or silicone; and wherein the botanical extract is incorporated into the second layer of the glove.

11. The glove as defined in claim 1, wherein the glove is a multi-layer glove having a first layer having an outer surface, a layer having the wearer contacting surface and one or more glove layers disposed between the first layer and the layer having the wearer contacting surface; wherein the botanical extract is incorporated in at least one layer of the glove.

12. The glove as defined in claim 11, wherein the elastomer for the layer of the glove into which the botanical extract is incorporated is an elastomer selected from the group consisting of a natural rubber latex, a synthetic polyisoprene, a chloroprene, a polyurethane, an acrylonitrile, a butadiene methylmethacrylate, a styrene butadiene styrene, a styrene isoprene styrene, a styrene ethylene butylene styrene, a silicone, an acrylate-based hydrogel, a polyvinyl chloride, any elastomer that is suspendable, soluble or miscible into an emulsion, a solution or a plastisol wherein the botanical extract is suspendable, soluble or miscible in the emulsion, solution or plastisol; and mixtures thereof.

* * * * *